US007897373B2

(12) United States Patent
Monsan et al.

(10) Patent No.: US 7,897,373 B2
(45) Date of Patent: Mar. 1, 2011

(54) CONSTRUCTION OF NEW VARIANTS OF DEXTRANSUCRASE DSR-S BY GENETIC ENGINEERING

(75) Inventors: Pierre F. Monsan, Modonville (FR); Magali Remaud-Simeon, Ramonville (FR); Gabrielle Potocki-Veronese, Lautignac (FR); Claire Moulis, Garidech (FR)

(73) Assignees: Centre National de la Recherche Scientifique, Paris (FR); Institut National de Recherche Agronomique, Paris (FR); Institut National des Sciences Appliquees de Toulouse, Toulouse (FR)

( * ) Notice: Subject to any disclaimer, the term of this patent is extended or adjusted under 35 U.S.C. 154(b) by 8 days.

(21) Appl. No.: 12/223,744

(22) PCT Filed: Feb. 8, 2007

(86) PCT No.: PCT/IB2007/000951

§ 371 (c)(1), (2), (4) Date: Nov. 11, 2008

(87) PCT Pub. No.: WO2007/091178

PCT Pub. Date: Aug. 16, 2007

(65) Prior Publication Data

US 2009/0258389 A1 Oct. 15, 2009

(30) Foreign Application Priority Data

Feb. 8, 2006 (FR) .................................. 06 01117

(51) Int. Cl.
*C12N 9/24* (2006.01)
*C07H 21/04* (2006.01)

(52) U.S. Cl. ...................... 435/200; 536/23.2; 536/23.4

(58) Field of Classification Search ................. 435/200; 536/23.2, 23.4
See application file for complete search history.

(56) References Cited

U.S. PATENT DOCUMENTS

| | | | | |
|---|---|---|---|---|
| 4,861,381 A | | 8/1989 | Paul et al. | 127/41 |
| 5,646,016 A | * | 7/1997 | McCoy et al. | 435/69.7 |

FOREIGN PATENT DOCUMENTS

| | | |
|---|---|---|
| DE | 102 25 380 | 12/2003 |
| EP | 1 201 131 | 5/2002 |
| WO | WO 89/12386 | 12/1989 |
| WO | WO 2006/063862 | 6/2006 |

OTHER PUBLICATIONS

Broun et al., Catalytic plasticity of fatty acid modification enzymes underlying chemical diversity of plant lipids. Science, 1998, vol. 282: 1315-1317.*

Devos et al., Practical limits of function prediction. Proteins: Structure, Function, and Genetics. 2000, vol. 41: 98-107.*

Seffernick et al., Melamine deaminase and Atrazine chlorohydrolase: 98 percent identical but functionally different. J. Bacteriol.,2001, vol. 183 (8): 2405-2410.*

Whisstock et al., Prediction of protein function from protein sequence. Q. Rev. Biophysics., 2003, vol. 36 (3): 307-340.*

Witkowski et al., Conversion of b-ketoacyl synthase to a Malonyl Decarboxylase by replacement of the active cysteine with glutamine. Biochemistry, 1999, vol. 38: 11643-11650.*

International Search Report and Written Opinion for International App. No. PCT/IB2007/000951, Oct. 31, 2007.

Argüello-Morales et al., "Proteolytic modification of *Leuconostoc mesenteroides* B-512F dextransucrase," Antonie van Leeuwenhoek, 2005, vol. 87, pp. 131-141.

Database, UniProt, The Universal Protein Knowledgebase, From *Leuconostoc mesenteroides*, Bhatnagar R.: "Dextransucrase," retrieved from EBI Database accession No. Q9ZAR4, Abstract, Oct. 17, 2006.

Monchois et al., "Effect of *Leuconostoc mesenteroides* NRRL B-512F Dextransucrase Carboxy-Terminal Deletions on Dextran and Oligosaccharide Synthesis," Applied and Environmental Microbiology, May 1998, vol. 64, No. 5, pp. 1644-1649.

Monchois et al., "Glucansucrases: mechanism of action and structure-function relationships," FEMS Microbiology Reviews, 1999, vol. 23, pp. 131-151.

(Continued)

*Primary Examiner*—Ganapathirama Raghu
(74) *Attorney, Agent, or Firm*—Kusner & Jaffe

(57) ABSTRACT

The present invention relates to a recombinant process for the production of truncated or mutated dextransucrases while conserving the enzymatic activity or their specificity in the synthesis of the α-1,6 bonds. The present invention relates to nucleic acid sequences of truncated or mutated dextransucrases, vectors containing the nucleic acid sequences and host cells transformed by sequences encoding truncated or mutated dextransucrases. In another aspect, the invention concerns a method for producing, in a recombinant manner, truncated or mutated dextransucrases which conserve their enzymatic activity or which conserve their specificity in the synthesis of α-1,6 bonds and can produce, from saccharose, dextrans with high molar mass and modified rheological properties compared with the properties of dextran obtained with the native enzyme and isomalto-oligosaccharides with a controlled molar mass and dextrans. The dextrans and isomalto-oligosaccharides of the invention can be used namely as texturing agents or as prebiotics.

10 Claims, 33 Drawing Sheets

OTHER PUBLICATIONS

Monchois et al., "Cloning and sequencing of a gene coding for an extracellular dextransucrase (DSRB) from *Leuconostoc mesenteroides* NRRL B-1299 synthesizing only a alpha (1-6) glucan," FEMS Microbiology Letters, 1998, vol. 159, pp. 307-315.

Monchois et al., "Characterization of *Leuconostoc mesenteroides* NRRL B-512F dextransucrase (DSRS) and identification of amino-acid residues playing a key role in enzyme activity," Applied Microbiology and Biotechnology, 1997, vol. 48, pp. 465-472.

Ryu et al., "Cloning of a dextransucrase gene (*fmcmds*) from a constitutive dextransucrase hyper-producing *Leuconostoc mesenteroides* B-512FMCM developed using VUV," Biotechnology Letters, 2000, vol. 22, pp. 421-425.

Funane et al., "Changes in linkage pattern of glucan products induced by substitution of Lys residues in the dextramsucrase," FEBS Letters, 2005, vol. 579, pp. 4739-4745.

Endo et al., "On-Line Monitoring of the Viscosity in Dextran Fermentation Using Piezoelectric Quartz Crystal," Biotechnology and Bioengineering, 1990, vol. 36, pp. 636-641.

Veljkovic et al., "Studies on dextran fermentation broth rheology," Enzyme and Microbial Technology, Nov. 1998, vol. 10, pp. 686-688.

Kubik et al., "Immobilization of dextransucrase and its use with soluble dextranase for glucooligosaccharides synthesis," Enzyme and Microbial Technology, 2004, vol. 34, pp. 555-560.

Robyt et al., "Relative Quantitative Effects of Acceptors in the Reaction of *Leuconostoc mesenteroides* B-512F Dextransucrase," Carbohydrate Research, Elseview Scientific Publishing Company, Amsterdam, NL, 1983, vol. 121, pp. 279-286.

Moulis et al., "High-level production and purification of a fully active recombinant dextransucrase from *Leuconostoc mesenteroides* NRRL B-512F," FEMS Microbiology Letters, 2006, vol. 261, pp. 203-210.

* cited by examiner

DSR-S vardel Δ4N sequence

M G : thioredoxin tag

H H : 6xHis tag H H

T Q : protein of interest

M G S D K I I H L T D D S F D T D V 18
ATG GGA TCT GAT AAA ATT ATT CAT CTG ACT GAT GAT TCT TTT GAT ACT GAT GTA 54

L K A D G A I L V D F W A H W C G P 36
CTT AAG GCA GAT GGT GCA ATC CTG GTT GAT TTC TGG GCA CAC TGG TGC GGT CCG 108

C K M I A P I L D E I A D E Y Q G K 54
TGC AAA ATG ATC GCT CCG ATT CTG GAT GAA ATC GCT GAC GAA TAT CAG GGC AAA 162

L T V A K L N I D H N P G T A P K Y 72
CTG ACC GTT GCA AAA CTG AAC ATC GAT CAC AAC CCG GGC ACT GCG CCG AAA TAT 216

G I R G I P T L L L F K N G E V A A 90
GGC ATC CGT GGT ATC CCG ACT CTG CTG CTG TTC AAA AAC GGT GAA GTG GCG GCA 270

T K V G A L S K G Q L K E F L D A N 108
ACC AAA GTG GGT GCA CTG TCT AAA GGT CAG TTG AAA GAG TTC CTC GAC GCT AAC 324

L A G S G S G D D D D K L A L M T Q 126
CTG GCC GGC TCT GGA TCC GGT GAT GAC GAT GAC AAG CTC GCC CTT ATG ACA CAA 378

Q V S G K Y V E K D G S W Y Y Y F D 144
CAA GTT AGC GGC AAG TAC GTT GAA AAA GAC GGT AGT TGG TAT TAT TAT TTT GAT 432

D G K N A K G L S T I D N N I Q Y F 162
GAT GGC AAA AAT GCT AAA GGT TTA TCA ACG ATA GAC AAC AAT ATT CAA TAT TTT 486

Y E S G K Q A K G Q Y V T I D N Q T 180
TAC GAG AGT GGT AAA CAA GCC AAA GGA CAG TAT GTC ACA ATT GAT AAT CAA ACA 540

Y Y F D K G S G D E L T G L Q S I D 198
TAT TAT TTT GAT AAG GGC TCA GGT GAT GAG TTA ACT GGT CTG CAA AGC ATT GAT 594

G N I V A F N D E G Q Q I F N Q Y Y 216
GGG AAC ATA GTT GCT TTT AAC GAT GAA GGG CAA CAA ATT TTT AAT CAA TAT TAC 648

Q S E N G T T Y Y F D D K G H A A T 234
CAA TCT GAA AAT GGT ACA ACA TAC TAC TTT GAT GAT AAA GGA CAC GCT GCT ACC 702

G I K N I E G K N Y Y F D N L G Q L 252
GGT ATT AAG AAT ATC GAG GGC AAA AAT TAT TAT TTT GAT AAT CTT GGG CAA CTA 756

K K G F S G V I D G Q I M T F D Q E 270
AAA AAA GGC TTC TCT GGT GTG ATT GAT GGT CAA ATA ATG ACA TTT GAT CAG GAA 810

T G Q E V S N T T S E I K E G L T T 288
ACA GGG CAA GAA GTT TCT AAC ACA ACT TCT GAA ATA AAA GAA GGT TTG ACG ACT 864

Q N T D Y S E H N A A H G T D A E D 306
CAA AAC ACG GAT TAT AGC GAA CAT AAT GCA GCC CAC GGT ACG GAT GCT GAG GAC 918

F E N I D G Y L T A S S W Y R P T G 324
TTT GAA AAT ATT GAC GGC TAT TTA ACA GCT AGT TCA TGG TAT CGT CCA ACA GGT 972

I L R N G T D W E P S T D T D F R P 342
ATT TTA CGT AAC GGA ACA GAC TGG GAA CCT TCT ACA GAT ACA GAT TTC AGA CCA 1026

I L S V W W P D K N T Q V N Y L N Y 360
ATA TTG TCA GTG TGG TGG CCA GAT AAG AAC ACC CAG GTC AAT TAT TTA AAT TAC 1080

M A D L G F I S N A D S F E T G D S 378
ATG GCT GAT TTA GGG TTT ATC AGT AAT GCG GAC AGT TTT GAA ACT GGG GAT AGC 1134

CAA AGC TTA TTA AAT GAA GCA AGT AAC TAT GTT CAA AAA TCA ATT GAA ATG AAA 1188

I S A Q Q S T E W L K D A M A A F I 414

ATT AGT GCG CAA CAA AGT ACA GAG TGG TTA AAG GAT GCA ATG GCG GCC TTC ATT 1242

V A Q P Q W N E T S E D M S N D H L 432

GTC GCG CAA CCA CAG TGG AAT GAA ACT AGT GAA GAT ATG AGC AAT GAC CAT TTA 1296

Q N G A L T Y V N S P L T P D A N S 450

CAA AAT GGC GCA TTA ACT TAT GTC AAC AGT CCA CTG ACA CCT GAC GCT AAT TCA 1350

N F R L L N R T P T N Q T G E Q A Y 468

AAC TTT AGA CTA CTT AAT CGG ACA CCA ACA AAC CAG ACT GGT GAA CAA GCG TAT 1404

N L D N S K G G F E L L L A N D V D 486

AAT TTA GAT AAT TCA AAA GGT GGT TTT GAA TTG TTG TTA GCC AAT GAC GTT GAT 1458

N S N P V V Q A E Q L N W L Y Y L M 504

AAT TCA AAC CCT GTA GTA CAA GCA GAA CAA TTG AAT TGG TTA TAT TAT TTA ATG 1512

N F G T I T A N D A D A N F D G I R 522

AAT TTT GGT ACG ATT ACG GCC AAC GAC GCG GAT GCT AAT TTT GAT GGT ATT CGT 1566

V D A V D N V D A D L L Q I A A D Y 540

GTA GAT GCA GTC GAC AAT GTG GAT GCT GAT TTG TTA CAA ATT GCT GCC GAT TAT 1620

F K L A Y G V D Q N D A T A N Q H L 558

TTC AAA CTA GCT TAC GGT GTT GAT CAA AAT GAT GCT ACT GCT AAT CAG CAT CTT 1674

S I L E D W S H N D P L Y V T D Q G 576

TCA ATT TTG GAA GAT TGG AGT CAC AAT GAT CCT TTG TAT GTA ACA GAT CAA GGA 1728

S N Q L T M D D Y V H T Q L I W S L 594

AGC AAT CAA TTA ACC ATG GAT GAT TAT GTG CAC ACA CAA TTA ATC TGG TCT CTA 1782

T K S S D I R G T M Q R F V D Y Y M 612

ACA AAA TCA TCT GAC ATA CGA GGT ACA ATG CAG CGC TTC GTG GAT TAT TAT ATG 1836

V D R S N D S T E N E A I P N Y S F 630

GTG GAT CGA TCT AAT GAT AGT ACA GAA AAC GAA GCC ATT CCT AAT TAC AGC TTT 1890

V R A H D S E V Q T V I A Q I V S D 648

GTA CGT GCA CAC GAC AGC GAA GTG CAA ACG GTT ATT GCC CAA ATT GTT TCC GAT 1944

L Y P D V E N S L A P T T E Q L A A 666

TTG TAT CCT GAT GTT GAA AAT AGT TTA GCA CCA ACA ACA GAA CAA TTG GCA GCT 1998

A F K V Y N E D E K L A D K K Y T Q 684

GCT TTC AAA GTA TAC AAT GAA GAT GAA AAA TTA GCA GAC AAA AAG TAC ACA CAA 2052

Y N M A S A Y A M L L T N K D T V P 702

TAT AAT ATG GCT AGT GCT TAT GCG ATG TTG CTA ACC AAT AAG GAT ACT GTT CCT 2106

R V Y Y G D L Y T D D G Q Y M A T K 720

CGT GTC TAT TAT GGC GAT TTA TAT ACA GAT GAT GGT CAA TAT ATG GCA ACA AAG 2160

S P Y Y D A I N T L L K A R V Q Y V 738

TCA CCA TAC TAT GAT GCG ATT AAC ACT TTG CTA AAG GCT AGA GTT CAG TAT GTT 2214

A G G Q S M S V D S N D V L T S V R 756

GCT GGT GGC CAA TCG ATG TCC GTT GAT AGT AAT GAC GTG TTA ACA AGT GTT CGC 2268

Y G K D A M T A S D T G T S E T R T 774

TAT GGT AAA GAT GCC ATG ACA GCT TCT GAC ACT GGA ACA TCT GAG ACG CGT ACT 2322

E G I G V I V S N N A E L Q L E D G 792

GAA GGT ATT GGA GTC ATC GTC AGC AAT AAC GCG GAG CTA CAA TTA GAG GAT GGG 2376

H T V T L H M G A A H K N Q A Y R A 810

CAT ACT GTC ACA TTG CAT ATG GGG GCA GCT CAT AAG AAC CAA GCT TAT CGT GCT 2430

FIGURE 1 (continued)

```
L   L   S   T   T   A   D   G   L   A   Y   Y   D   T   D   E   N   A    828
TTG TTA TCA ACA ACT GCA GAT GGA TTA GCT TAT TAT GAT ACT GAT GAA AAT GCA 2484

P   V   A   Y   T   D   A   N   G   D   L   I   F   T   N   E   S   I    846
CCT GTG GCG TAC ACA GAT GCT AAC GGC GAT TTG ATT TTT ACG AAT GAA TCA ATT 2538

Y   G   V   Q   N   P   Q   V   S   G   Y   L   A   V   W   V   P   V    864
TAT GGT GTA CAA AAT CCA CAA GTT TCT GGT TAC TTG GCA GTT TGG GTT CCG GTA 2592

G   A   Q   Q   D   Q   D   A   R   T   A   S   D   T   T   T   N   T    882
GGT GCG CAA CAA GAT CAA GAT GCA CGA ACG GCC TCT GAT ACA ACA ACA AAC ACG 2646

S   D   K   V   F   H   S   N   A   A   L   D   S   Q   V   I   Y   E    900
AGT GAT AAA GTG TTC CAT TCA AAC GCT GCT CTT GAT TCT CAA GTC ATC TAC GAA 2700

G   F   S   N   F   Q   A   F   A   T   D   S   S   E   Y   T   N   V    918
GGT TTC TCA AAC TTC CAA GCA TTT GCT ACA GAC AGC AGT GAA TAT ACA AAC GTA 2754

V   I   A   Q   N   A   D   Q   F   K   Q   W   G   V   T   S   F   Q    936
GTC ATC GCT CAG AAT GCG GAC CAA TTT AAG CAA TGG GGT GTG ACA AGC TTC CAA 2808

L   A   P   Q   Y   R   S   S   T   D   T   S   F   L   D   S   I   I    954
TTG GCA CCA CAA TAT CGT TCA AGT ACA GAT ACA AGT TTC TTG GAT TCA ATT ATT 2862

Q   N   G   Y   A   F   T   D   R   Y   D   L   G   Y   G   T   P   T    972
CAA AAC GGG TAT GCA TTC ACG GAT CGT TAT GAC TTA GGT TAT GGC ACA CCG ACA 2916

K   Y   G   T   A   D   Q   L   R   D   A   I   K   A   L   H   A   S    990
AAA TAT GGA ACT GCT GAT CAG TTG CGC GAT GCT ATT AAA GCC TTA CAT GCT AGC 2970

G   I   Q   A   I   A   D   W   V   P   D   Q   I   Y   N   L   P   E   1008
GGT ATT CAA GCC ATT GCC GAT TGG GTG CCG GAC CAA ATT TAT AAT TTG CCA GAG 3024

Q   E   L   A   T   V   T   R   T   N   S   F   G   D   D   D   T   D   1026
CAA GAA TTA GCT ACT GTC ACA AGA ACA AAT TCA TTT GGA GAT GAC GAT ACA GAT 3078

S   D   I   D   N   A   L   Y   V   V   Q   S   R   G   G   G   Q   Y   1044
TCT GAT ATT GAC AAT GCC TTA TAT GTT GTA CAA AGT CGT GGG GGT GGT CAA TAT 3132

Q   E   M   Y   G   G   A   F   L   E   E   L   Q   A   L   Y   P   S   1062
CAA GAG ATG TAT GGT GGT GCC TTC TTA GAA GAG TTA CAG GCA CTC TAT CCA TCC 3186

L   F   K   V   N   Q   I   S   T   G   V   P   I   D   G   S   V   K   1080
CTA TTT AAA GTG AAT CAA ATC TCA ACT GGC GTT CCA ATT GAT GGC AGT GTA AAG 3240

I   T   E   W   A   A   K   Y   F   N   G   S   N   I   Q   G   K   G   1098
ATT ACT GAG TGG GCG GCT AAG TAC TTC AAT GGC TCT AAC ATC CAA GGT AAA GGT 3294

A   G   Y   V   L   K   D   M   G   S   N   K   Y   F   K   V   V   S   1116
GCT GGA TAC GTA TTG AAA GAT ATG GGT TCT AAT AAG TAC TTT AAG GTC GTT TCG 3348

N   T   E   D   G   D   Y   L   P   K   Q   L   T   N   D   L   S   E   1134
AAC ACT GAG GAT GGT GAC TAC TTA CCA AAA CAG TTA ACT AAT GAT CTG TCA GAA 3402

T   G   F   T   H   D   D   K   G   I   I   Y   Y   T   L   S   G   Y   1152
ACT GGC TTT ACA CAC GAT GAT AAA GGA ATC ATC TAT TAT ACA TTA AGT GGT TAT 3456

R   A   Q   N   A   F   I   Q   D   D   D   N   N   Y   Y   Y   F   D   1170
CGT GCC CAA AAT GCA TTT ATT CAA GAT GAT GAT AAT AAC TAT TAC TAT TTT GAT 3510

K   T   G   H   L   V   T   G   L   Q   K   I   N   N   H   T   Y   F   1188
AAA ACA GGT CAT TTA GTA ACA GGT TTG CAA AAG ATT AAT AAC CAT ACC TAC TTC 3564

F   L   P   N   G   I   E   L   V   K   S   F   L   Q   N   E   D   G   1206
TTC TTA CCT AAT GGT ATC GAA CTG GTC AAG AGC TTC TTA CAA AAC GAA GAT GGT 3618

T   I   V   Y   F   D   K   K   G   H   Q   V   F   D   Q   Y   I   T   1224
ACA ATT GTT TAT TTC GAT AAG AAA GGT CAT CAA GTT TTT GAT CAA TAT ATA ACT 3672
```

FIGURE 1 (continued)

D Q N G N A Y Y F D D A G V M L K S 1242
GAT CAA AAT GGA AAT GCG TAT TAC TTT GAT GAT GCT GGT GTA ATG CTT AAA TCA 3726

G L A T I D G H Q Q Y F D Q N G V Q 1260
GGG CTT GCA ACG ATT GAT GGA CAT CAA CAG TAT TTT GAT CAA AAT GGT GTG CAG 3780

V K D K F V I G T D G Y K Y Y F E P 1278
GTT AAG GAT AAG TTT GTG ATT GGC ACT GAT GGT TAT AAG TAT TAC TTT GAA CCA 3834

G S G N L A I L R Y V Q N S K N Q W 1296
GGT AGT GGT AAC TTA GCT ATC CTA CGT TAT GTG CAA AAT AGT AAG AAT CAA TGG 3888

F Y F D G N G H A V T G F Q T I N G 1314
TTC TAT TTT GAT GGT AAT GGC CAT GCT GTC ACT GGT TTC CAA ACA ATT AAT GGT 3942

K K Q Y F Y N D G H Q S K G E F I D 1332
AAA AAA CAA TAT TTC TAT AAT GAT GGT CAT CAA AGT AAA GGT GAA TTC ATT GAT 3996

A D G D T F Y T S A T D G R L V T G 1350
GCA GAC GGG GAT ACT TTC TAT ACG AGT GCC ACT GAT GGT CGC CTA GTA ACT GGT 4050

V Q K I N G I T Y A F D N T G N L I 1368
GTT CAG AAG ATT AAT GGT ATT ACC TAT GCT TTT GAT AAC ACA GGA AAT TTG ATC 4104

T N Q Y Y Q L A D G K Y M L L D D S 1386
ACA AAT CAG TAT TAT CAA TTA GCA GAT GGT AAA TAT ATG TTG TTA GAT GAT AGT 4158

G R A K T G F V L Q D G V L R Y F D 1404
GGT CGT GCG AAA ACA GGG TTT GTA TTG CAA GAT GGT GTA CTA AGA TAC TTC GAT 4212

Q N G E Q V K D A I I V D P D T N L 1422
CAA AAC GGT GAG CAA GTG AAA GAT GCT ATC ATT GTG GAT CCA GAT ACT AAC TTG 4266

*S Y K G E L E G K P I P N P L L G L* 1440
AGT TAC AAG GGC GAG CTT GAA GGT AAG CCT ATC CCT AAC CCT CTC CTC GGT CTC 4320

*D S T R T G* H H H H H H 1452
GAT TCT ACG CGT ACC GGT CAT CAT CAC CAT CAC CAT 4356

FIGURE 1 (end)

DSR-S vardel Δ3 sequence

M G : thioredoxin tag

H H : 6xHis tag H H

T Q : protein of interest

M G S D K I I H L T D D S F D T D V 18
ATG GGA TCT GAT AAA ATT ATT CAT CTG ACT GAT GAT TCT TTT GAT ACT GAT GTA 54

L K A D G A I L V D F W A H W C G P 36
CTT AAG GCA GAT GGT GCA ATC CTG GTT GAT TTC TGG GCA CAC TGG TGC GGT CCG 108

C K M I A P I L D E I A D E Y Q G K 54
TGC AAA ATG ATC GCT CCG ATT CTG GAT GAA ATC GCT GAC GAA TAT CAG GGC AAA 162

L T V A K L N I D H N P G T A P K Y 72
CTG ACC GTT GCA AAA CTG AAC ATC GAT CAC AAC CCG GGC ACT GCG CCG AAA TAT 216

G I R G I P T L L L F K N G E V A A 90
GGC ATC CGT GGT ATC CCG ACT CTG CTG CTG TTC AAA AAC GGT GAA GTG GCG GCA 270

T K V G A L S K G Q L K E F L D A N 108
ACC AAA GTG GGT GCA CTG TCT AAA GGT CAG TTG AAA GAG TTC CTC GAC GCT AAC 324

L A G S G S G D D D D K L A L M T Q 126
CTG GCC GGC TCT GGA TCC GGT GAT GAC GAT GAC AAG CTC GCC CTT ATG ACA CAA 378

Q V S G K Y V E K D G S W Y Y Y F D 144
CAA GTT AGC GGC AAG TAC GTT GAA AAA GAC GGT AGT TGG TAT TAT TAT TTT GAT 432

D G K N A K G L S T I D N N I Q Y F 162
GAT GGC AAA AAT GCT AAA GGT TTA TCA ACG ATA GAC AAC AAT ATT CAA TAT TTT 486

Y E S G K Q A K G Q Y V T I D N Q T 180
TAC GAG AGT GGT AAA CAA GCC AAA GGA CAG TAT GTC ACA ATT GAT AAT CAA ACA 540

Y Y F D K G S G D E L T G L Q S I D 198
TAT TAT TTT GAT AAG GGC TCA GGT GAT GAG TTA ACT GGT CTG CAA AGC ATT GAT 594

G N I V A F N D E G Q Q I F N Q Y Y 216
GGG AAC ATA GTT GCT TTT AAC GAT GAA GGG CAA CAA ATT TTT AAT CAA TAT TAC 648

Q S E N G T T Y Y F D D K G H A A T 234
CAA TCT GAA AAT GGT ACA ACA TAC TAC TTT GAT GAT AAA GGA CAC GCT GCT ACC 702

G I K N I E G K N Y Y F D N L G Q L 252
GGT ATT AAG AAT ATC GAG GGC AAA AAT TAT TAT TTT GAT AAT CTT GGG CAA CTA 756

K K G F S G V I D G Q I M T F D Q E 270
AAA AAA GGC TTC TCT GGT GTG ATT GAT GGT CAA ATA ATG ACA TTT GAT CAG GAA 810

T G Q E V S N T T S E I K E G L T T 288
ACA GGG CAA GAA GTT TCT AAC ACA ACT TCT GAA ATA AAA GAA GGT TTG ACG ACT 864

Q N T D Y S E H N A A H G T D A E D 306
CAA AAC ACG GAT TAT AGC GAA CAT AAT GCA GCC CAC GGT ACG GAT GCT GAG GAC 918

F E N I D G Y L T A S S W Y R P T G 324
TTT GAA AAT ATT GAC GGC TAT TTA ACA GCT AGT TCA TGG TAT CGT CCA ACA GGT 972

I L R N G T D W E P S T D T D F R P 342
ATT TTA CGT AAC GGA ACA GAC TGG GAA CCT TCT ACA GAT ACA GAT TTC AGA CCA 1026

I L S V W W P D K N T Q V N Y L N Y 360
ATA TTG TCA GTG TGG TGG CCA GAT AAG AAC ACC CAG GTC AAT TAT TTA AAT TAC 1080

FIGURE 2

```
 M   A   D   L   G   F   I   S   N   A   D   S   F   E   T   G   D   S     378
ATG GCT GAT TTA GGG TTT ATC AGT AAT GCG GAC AGT TTT GAA ACT GGG GAT AGC   1134

 Q   S   L   L   N   E   A   S   N   Y   V   Q   K   S   I   E   M   K     396
CAA AGC TTA TTA AAT GAA GCA AGT AAC TAT GTT CAA AAA TCA ATT GAA ATG AAA   1188

 I   S   A   Q   Q   S   T   E   W   L   K   D   A   M   A   A   F   I     414
ATT AGT GCG CAA CAA AGT ACA GAG TGG TTA AAG GAT GCA ATG GCG GCC TTC ATT   1242

 V   A   Q   P   Q   W   N   E   T   S   E   D   M   S   N   D   H   L     432
GTC GCG CAA CCA CAG TGG AAT GAA ACT AGT GAA GAT ATG AGC AAT GAC CAT TTA   1296

 Q   N   G   A   L   T   Y   V   N   S   P   L   T   P   D   A   N   S     450
CAA AAT GGC GCA TTA ACT TAT GTC AAC AGT CCA CTG ACA CCT GAC GCT AAT TCA   1350

 N   F   R   L   L   N   R   T   P   T   N   Q   T   G   E   Q   A   Y     468
AAC TTT AGA CTA CTT AAT CGG ACA CCA ACA AAC CAG ACT GGT GAA CAA GCG TAT   1404

 N   L   D   N   S   K   G   G   F   E   L   L   L   A   N   D   V   D     486
AAT TTA GAT AAT TCA AAA GGT GGT TTT GAA TTG TTG TTA GCC AAT GAC GTT GAT   1458

 N   S   N   P   V   V   Q   A   E   Q   L   N   W   L   Y   Y   L   M     504
AAT TCA AAC CCT GTA GTA CAA GCA GAA CAA TTG AAT TGG TTA TAT TAT TTA ATG   1512

 N   F   G   T   I   T   A   N   D   A   D   A   N   F   D   G   I   R     522
AAT TTT GGT ACG ATT ACG GCC AAC GAC GCG GAT GCT AAT TTT GAT GGT ATT CGT   1566

 V   D   A   V   D   N   V   D   A   D   L   L   Q   I   A   A   D   Y     540
GTA GAT GCA GTC GAC AAT GTG GAT GCT GAT TTG TTA CAA ATT GCT GCC GAT TAT   1620

 F   K   L   A   Y   G   V   D   Q   N   D   A   T   A   N   Q   H   L     558
TTC AAA CTA GCT TAC GGT GTT GAT CAA AAT GAT GCT ACT GCT AAT CAG CAT CTT   1674

 S   I   L   E   D   W   S   H   N   D   P   L   Y   V   T   D   Q   G     576
TCA ATT TTG GAA GAT TGG AGT CAC AAT GAT CCT TTG TAT GTA ACA GAT CAA GGA   1728

 S   N   Q   L   T   M   D   D   Y   V   H   T   Q   L   I   W   S   L     594
AGC AAT CAA TTA ACC ATG GAT GAT TAT GTG CAC ACA CAA TTA ATC TGG TCT CTA   1782

 T   K   S   S   D   I   R   G   T   M   Q   R   F   V   D   Y   Y   M     612
ACA AAA TCA TCT GAC ATA CGA GGT ACA ATG CAG CGC TTC GTG GAT TAT TAT ATG   1836

 V   D   R   S   N   D   S   T   E   N   E   A   I   P   N   Y   S   F     630
GTG GAT CGA TCT AAT GAT AGT ACA GAA AAC GAA GCC ATT CCT AAT TAC AGC TTT   1890

 V   R   A   H   D   S   E   V   Q   T   V   I   A   Q   I   V   S   D     648
GTA CGT GCA CAC GAC AGC GAA GTG CAA ACG GTT ATT GCC CAA ATT GTT TCC GAT   1944

 L   Y   P   D   V   E   N   S   L   A   P   T   T   E   Q   L   A   A     666
TTG TAT CCT GAT GTT GAA AAT AGT TTA GCA CCA ACA ACA GAA CAA TTG GCA GCT   1998

 A   F   K   V   Y   N   E   D   E   K   L   A   D   K   K   Y   T   Q     684
GCT TTC AAA GTA TAC AAT GAA GAT GAA AAA TTA GCA GAC AAA AAG TAC ACA CAA   2052

 Y   N   M   A   S   A   Y   A   M   L   L   T   N   K   D   T   V   P     702
TAT AAT ATG GCT AGT GCT TAT GCG ATG TTG CTA ACC AAT AAG GAT ACT GTT CCT   2106

 R   V   Y   Y   G   D   L   Y   T   D   D   G   Q   Y   M   A   T   K     720
CGT GTC TAT TAT GGC GAT TTA TAT ACA GAT GAT GGT CAA TAT ATG GCA ACA AAG   2160

 S   P   Y   Y   D   A   I   N   T   L   L   K   A   R   V   Q   Y   V     738
TCA CCA TAC TAT GAT GCG ATT AAC ACT TTG CTA AAG GCT AGA GTT CAG TAT GTT   2214

 A   G   G   Q   S   M   S   V   D   S   N   D   V   L   T   S   V   R     756
GCT GGT GGC CAA TCG ATG TCC GTT GAT AGT AAT GAC GTG TTA ACA AGT GTT CGC   2268

 Y   G   K   D   A   M   T   A   S   D   T   G   T   S   E   T   R   T     774
TAT GGT AAA GAT GCC ATG ACA GCT TCT GAC ACT GGA ACA TCT GAG ACG CGT ACT   2322

 E   G   I   G   V   I   V   S   N   N   A   E   L   Q   L   E   D   G     792
GAA GGT ATT GGA GTC ATC GTC AGC AAT AAC GCG GAG CTA CAA TTA GAG GAT GGG   2376
```

FIGURE 2 (continued)

```
H   T   V   T   L   H   M   G   A   A   H   K   N   Q   A   Y   R   A     810
CAT ACT GTC ACA TTG CAT ATG GGG GCA GCT CAT AAG AAC CAA GCT TAT CGT GCT   2430

L   L   S   T   T   A   D   G   L   A   Y   Y   D   T   D   E   N   A     828
TTG TTA TCA ACA ACT GCA GAT GGA TTA GCT TAT TAT GAT ACT GAT GAA AAT GCA   2484

P   V   A   Y   T   D   A   N   G   D   L   I   F   T   N   E   S   I     846
CCT GTG GCG TAC ACA GAT GCT AAC GGC GAT TTG ATT TTT ACG AAT GAA TCA ATT   2538

Y   G   V   Q   N   P   Q   V   S   G   Y   L   A   V   W   V   P   V     864
TAT GGT GTA CAA AAT CCA CAA GTT TCT GGT TAC TTG GCA GTT TGG GTT CCG GTA   2592

G   A   Q   Q   D   Q   D   A   R   T   A   S   D   T   T   T   N   T     882
GGT GCG CAA CAA GAT CAA GAT GCA CGA ACG GCC TCT GAT ACA ACA ACA AAC ACG   2646

S   D   K   V   F   H   S   N   A   A   L   D   S   Q   V   I   Y   E     900
AGT GAT AAA GTG TTC CAT TCA AAC GCT GCT CTT GAT TCT CAA GTC ATC TAC GAA   2700

G   F   S   N   F   Q   A   F   A   T   D   S   S   E   Y   T   N   V     918
GGT TTC TCA AAC TTC CAA GCA TTT GCT ACA GAC AGC AGT GAA TAT ACA AAC GTA   2754

V   I   A   Q   N   A   D   Q   F   K   Q   W   G   V   T   S   F   Q     936
GTC ATC GCT CAG AAT GCG GAC CAA TTT AAG CAA TGG GGT GTG ACA AGC TTC CAA   2808

L   A   P   Q   Y   R   S   S   T   D   T   S   F   L   D   S   I   I     954
TTG GCA CCA CAA TAT CGT TCA AGT ACA GAT ACA AGT TTC TTG GAT TCA ATT ATT   2862

Q   N   G   Y   A   F   T   D   R   Y   D   L   G   Y   G   T   P   T     972
CAA AAC GGG TAT GCA TTC ACG GAT CGT TAT GAC TTA GGT TAT GGC ACA CCG ACA   2916

K   Y   G   T   A   D   Q   L   R   D   A   I   K   A   L   H   A   S     990
AAA TAT GGA ACT GCT GAT CAG TTG CGC GAT GCT ATT AAA GCC TTA CAT GCT AGC   2970

G   I   Q   A   I   A   D   W   V   P   D   Q   I   Y   N   L   P   E     1008
GGT ATT CAA GCC ATT GCC GAT TGG GTG CCG GAC CAA ATT TAT AAT TTG CCA GAG   3024

Q   E   L   A   T   V   T   R   T   N   S   F   G   D   D   D   T   D     1026
CAA GAA TTA GCT ACT GTC ACA AGA ACA AAT TCA TTT GGA GAT GAC GAT ACA GAT   3078

S   D   I   D   N   A   L   Y   V   V   Q   S   R   G   G   G   Q   Y     1044
TCT GAT ATT GAC AAT GCC TTA TAT GTT GTA CAA AGT CGT GGG GGT GGT CAA TAT   3132

Q   E   M   Y   G   G   A   F   L   E   E   L   Q   A   L   Y   P   S     1062
CAA GAG ATG TAT GGT GGT GCC TTC TTA GAA GAG TTA CAG GCA CTC TAT CCA TCC   3186

L   F   K   V   N   Q   I   S   T   G   V   P   I   D   G   S   V   K     1080
CTA TTT AAA GTG AAT CAA ATC TCA ACT GGC GTT CCA ATT GAT GGC AGT GTA AAG   3240

I   T   E   W   A   A   K   Y   F   N   G   S   N   I   Q   G   K   G     1098
ATT ACT GAG TGG GCG GCT AAG TAC TTC AAT GGC TCT AAC ATC CAA GGT AAA GGT   3294

A   G   Y   V   L   K   D   M   G   S   N   K   Y   F   K   V   V   S     1116
GCT GGA TAC GTA TTG AAA GAT ATG GGT TCT AAT AAG TAC TTT AAG GTC GTT TCG   3348

N   T   E   D   G   D   Y   L   P   K   Q   L   T   N   D   L   S   E     1134
AAC ACT GAG GAT GGT GAC TAC TTA CCA AAA CAG TTA ACT AAT GAT CTG TCA GAA   3402

T   G   F   T   H   D   D   K   G   I   I   Y   Y   T   L   S   G   Y     1152
ACT GGC TTT ACA CAC GAT GAT AAA GGA ATC ATC TAT TAT ACA TTA AGT GGT TAT   3456

R   A   Q   N   A   F   I   Q   D   D   D   N   N   Y   Y   Y   F   D     1170
CGT GCC CAA AAT GCA TTT ATT CAA GAT GAT GAT AAT AAC TAT TAC TAT TTT GAT   3510

K   T   G   H   L   V   T   G   L   Q   K   I   N   N   H   T   Y   F     1188
AAA ACA GGT CAT TTA GTA ACA GGT TTG CAA AAG ATT AAT AAC CAT ACC TAC TTC   3564

F   L   P   N   G   I   E   L   V   K   S   F   L   Q   N   E   D   G     1206
TTC TTA CCT AAT GGT ATC GAA CTG GTC AAG AGC TTC TTA CAA AAC GAA GAT GGT   3618

T   I   V   Y   F   D   K   K   G   H   Q   V   F   D   Q   Y   I   T     1224
ACA ATT GTT TAT TTC GAT AAG AAA GGT CAT CAA GTT TTT GAT CAA TAT ATA ACT   3672
```

FIGURE 2 (continued)

D Q N G N A Y Y F D D A G V M L K S 1242
GAT CAA AAT GGA AAT GCG TAT TAC TTT GAT GAT GCT GGT GTA ATG CTT AAA TCA 3726

G L A T I D G H Q Q Y F D Q N G V Q 1260
GGG CTT GCA ACG ATT GAT GGA CAT CAA CAG TAT TTT GAT CAA AAT GGT GTG CAG 3780

V K D K F V I G T D G Y K Y Y F E P 1278
GTT AAG GAT AAG TTT GTG ATT GGC ACT GAT GGT TAT AAG TAT TAC TTT GAA CCA 3834

G S G N L A I L R Y V Q N S K N Q W 1296
GGT AGT GGT AAC TTA GCT ATC CTA CGT TAT GTG CAA AAT AGT AAG AAT CAA TGG 3888

F Y F D G N G H A V T G F Q T I N G 1314
TTC TAT TTT GAT GGT AAT GGC CAT GCT GTC ACT GGT TTC CAA ACA ATT AAT GGT 3942

K K Q Y F Y N D G H Q S K G E F I D 1332
AAA AAA CAA TAT TTC TAT AAT GAT GGT CAT CAA AGT AAA GGT GAA TTC ATT GAT 3996

A D G Y K G E L E G K P I P N P L L 1350
GCA GAC GGG TAC AAG GGC GAG CTT GAA GGT AAG CCT ATC CCT AAC CCT CTC CTC 4050

G L D S T R T G H H H H H H 1364
GGT CTC GAT TCT ACG CGT ACC GGT CAT CAT CAC CAT CAC CAT 4092

FIGURE 2 (end)

DSR-S vardel Core sequence

M G : thioredoxin tag

H H : 6xHis tag H H

T Q : protein of interest

M G S D K I I H L T D D S F D T D V 18
ATG GGA TCT GAT AAA ATT ATT CAT CTG ACT GAT GAT TCT TTT GAT ACT GAT GTA 54

L K A D G A I L V D F W A H W C G P 36
CTT AAG GCA GAT GGT GCA ATC CTG GTT GAT TTC TGG GCA CAC TGG TGC GGT CCG 108

C K M I A P I L D E I A D E Y Q G K 54
TGC AAA ATG ATC GCT CCG ATT CTG GAT GAA ATC GCT GAC GAA TAT CAG GGC AAA 162

L T V A K L N I D H N P G T A P K Y 72
CTG ACC GTT GCA AAA CTG AAC ATC GAT CAC AAC CCG GGC ACT GCG CCG AAA TAT 216

G I R G I P T L L L F K N G E V A A 90
GGC ATC CGT GGT ATC CCG ACT CTG CTG CTG TTC AAA AAC GGT GAA GTG GCG GCA 270

T K V G A L S K G Q L K E F L D A N 108
ACC AAA GTG GGT GCA CTG TCT AAA GGT CAG TTG AAA GAG TTC CTC GAC GCT AAC 324

L A G S G S G D D D D K L A L M T Q 126
CTG GCC GGC TCT GGA TCC GGT GAT GAC GAT GAC AAG CTC GCC CTT ATG ACA CAA 378

Q V S G K Y V E K D G S W Y Y Y F D 144
CAA GTT AGC GGC AAG TAC GTT GAA AAA GAC GGT AGT TGG TAT TAT TAT TTT GAT 432

D G K N A K G L S T I D N N I Q Y F 162
GAT GGC AAA AAT GCT AAA GGT TTA TCA ACG ATA GAC AAC AAT ATT CAA TAT TTT 486

Y E S G K Q A K G Q Y V T I D N Q T 180
TAC GAG AGT GGT AAA CAA GCC AAA GGA CAG TAT GTC ACA ATT GAT AAT CAA ACA 540

Y Y F D K G S G D E L T G L Q S I D 198
TAT TAT TTT GAT AAG GGC TCA GGT GAT GAG TTA ACT GGT CTG CAA AGC ATT GAT 594

G N I V A F N D E G Q Q I F N Q Y Y 216
GGG AAC ATA GTT GCT TTT AAC GAT GAA GGG CAA CAA ATT TTT AAT CAA TAT TAC 648

Q S E N G T T Y Y F D D K G H A A T 234
CAA TCT GAA AAT GGT ACA ACA TAC TAC TTT GAT GAT AAA GGA CAC GCT GCT ACC 702

G I K N I E G K N Y Y F D N L G Q L 252
GGT ATT AAG AAT ATC GAG GGC AAA AAT TAT TAT TTT GAT AAT CTT GGG CAA CTA 756

K K G F S G V I D G Q I M T F D Q E 270
AAA AAA GGC TTC TCT GGT GTG ATT GAT GGT CAA ATA ATG ACA TTT GAT CAG GAA 810

T G Q E V S N T T S E I K E G L T T 288
ACA GGG CAA GAA GTT TCT AAC ACA ACT TCT GAA ATA AAA GAA GGT TTG ACG ACT 864

Q N T D Y S E H N A A H G T D A E D 306
CAA AAC ACG GAT TAT AGC GAA CAT AAT GCA GCC CAC GGT ACG GAT GCT GAG GAC 918

F E N I D G Y L T A S S W Y R P T G 324
TTT GAA AAT ATT GAC GGC TAT TTA ACA GCT AGT TCA TGG TAT CGT CCA ACA GGT 972

I L R N G T D W E P S T D T D F R P 342
ATT TTA CGT AAC GGA ACA GAC TGG GAA CCT TCT ACA GAT ACA GAT TTC AGA CCA 1026

I L S V W W P D K N T Q V N Y L N Y 360
ATA TTG TCA GTG TGG TGG CCA GAT AAG AAC ACC CAG GTC AAT TAT TTA AAT TAC 1080

M A D L G F I S N A D S F E T G D S 378
ATG GCT GAT TTA GGG TTT ATC AGT AAT GCG GAC AGT TTT GAA ACT GGG GAT AGC 1134

FIGURE 3

Q S L L N E A S N Y V Q K S I E M K 396
CAA AGC TTA TTA AAT GAA GCA AGT AAC TAT GTT CAA AAA TCA ATT GAA ATG AAA 1188

I S A Q Q S T E W L K D A M A A F I 414
ATT AGT GCG CAA CAA AGT ACA GAG TGG TTA AAG GAT GCA ATG GCG GCC TTC ATT 1242

V A Q P Q W N E T S E D M S N D H L 432
GTC GCG CAA CCA CAG TGG AAT GAA ACT AGT GAA GAT ATG AGC AAT GAC CAT TTA 1296

Q N G A L T Y V N S P L T P D A N S 450
CAA AAT GGC GCA TTA ACT TAT GTC AAC AGT CCA CTG ACA CCT GAC GCT AAT TCA 1350

N F R L L N R T P T N Q T G E Q A Y 468
AAC TTT AGA CTA CTT AAT CGG ACA CCA ACA AAC CAG ACT GGT GAA CAA GCG TAT 1404

N L D N S K G G F E L L L A N D V D 486
AAT TTA GAT AAT TCA AAA GGT GGT TTT GAA TTG TTG TTA GCC AAT GAC GTT GAT 1458

N S N P V V Q A E Q L N W L Y Y L M 504
AAT TCA AAC CCT GTA GTA CAA GCA GAA CAA TTG AAT TGG TTA TAT TAT TTA ATG 1512

N F G T I T A N D A D A N F D G I R 522
AAT TTT GGT ACG ATT ACG GCC AAC GAC GCG GAT GCT AAT TTT GAT GGT ATT CGT 1566

V D A V D N V D A D L L Q I A A D Y 540
GTA GAT GCA GTC GAC AAT GTG GAT GCT GAT TTG TTA CAA ATT GCT GCC GAT TAT 1620

F K L A Y G V D Q N D A T A N Q H L 558
TTC AAA CTA GCT TAC GGT GTT GAT CAA AAT GAT GCT ACT GCT AAT CAG CAT CTT 1674

S I L E D W S H N D P L Y V T D Q G 576
TCA ATT TTG GAA GAT TGG AGT CAC AAT GAT CCT TTG TAT GTA ACA GAT CAA GGA 1728

S N Q L T M D D Y V H T Q L I W S L 594
AGC AAT CAA TTA ACC ATG GAT GAT TAT GTG CAC ACA CAA TTA ATC TGG TCT CTA 1782

T K S S D I R G T M Q R F V D Y Y M 612
ACA AAA TCA TCT GAC ATA CGA GGT ACA ATG CAG CGC TTC GTG GAT TAT TAT ATG 1836

V D R S N D S T E N E A I P N Y S F 630
GTG GAT CGA TCT AAT GAT AGT ACA GAA AAC GAA GCC ATT CCT AAT TAC AGC TTT 1890

V R A H D S E V Q T V I A Q I V S D 648
GTA CGT GCA CAC GAC AGC GAA GTG CAA ACG GTT ATT GCC CAA ATT GTT TCC GAT 1944

L Y P D V E N S L A P T T E Q L A A 666
TTG TAT CCT GAT GTT GAA AAT AGT TTA GCA CCA ACA ACA GAA CAA TTG GCA GCT 1998

A F K V Y N E D E K L A D K K Y T Q 684
GCT TTC AAA GTA TAC AAT GAA GAT GAA AAA TTA GCA GAC AAA AAG TAC ACA CAA 2052

Y N M A S A Y A M L L T N K D T V P 702
TAT AAT ATG GCT AGT GCT TAT GCG ATG TTG CTA ACC AAT AAG GAT ACT GTT CCT 2106

R V Y Y G D L Y T D D G Q Y M A T K 720
CGT GTC TAT TAT GGC GAT TTA TAT ACA GAT GAT GGT CAA TAT ATG GCA ACA AAG 2160

S P Y Y D A I N T L L K A R V Q Y V 738
TCA CCA TAC TAT GAT GCG ATT AAC ACT TTG CTA AAG GCT AGA GTT CAG TAT GTT 2214

A G G Q S M S V D S N D V L T S V R 756
GCT GGT GGC CAA TCG ATG TCC GTT GAT AGT AAT GAC GTG TTA ACA AGT GTT CGC 2268

Y G K D A M T A S D T G T S E T R T 774
TAT GGT AAA GAT GCC ATG ACA GCT TCT GAC ACT GGA ACA TCT GAG ACG CGT ACT 2322

E G I G V I V S N N A E L Q L E D G 792
GAA GGT ATT GGA GTC ATC GTC AGC AAT AAC GCG GAG CTA CAA TTA GAG GAT GGG 2376

H T V T L H M G A A H K N Q A Y R A 810
CAT ACT GTC ACA TTG CAT ATG GGG GCA GCT CAT AAG AAC CAA GCT TAT CGT GCT 2430

FIGURE 3 (continued)

```
 L   L   S   T   T   A   D   G   L   A   Y   Y   D   T   D   E   N   A     828
TTG TTA TCA ACA ACT GCA GAT GGA TTA GCT TAT TAT GAT ACT GAT GAA AAT GCA   2484

 P   V   A   Y   T   D   A   N   G   D   L   I   F   T   N   E   S   I     846
CCT GTG GCG TAC ACA GAT GCT AAC GGC GAT TTG ATT TTT ACG AAT GAA TCA ATT   2538

 Y   G   V   Q   N   P   Q   V   S   G   Y   L   A   V   W   V   P   V     864
TAT GGT GTA CAA AAT CCA CAA GTT TCT GGT TAC TTG GCA GTT TGG GTT CCG GTA   2592

 G   A   Q   Q   D   Q   D   A   R   T   A   S   D   T   T   T   N   T     882
GGT GCG CAA CAA GAT CAA GAT GCA CGA ACG GCC TCT GAT ACA ACA ACA AAC ACG   2646

 S   D   K   V   F   H   S   N   A   A   L   D   S   Q   V   I   Y   E     900
AGT GAT AAA GTG TTC CAT TCA AAC GCT GCT CTT GAT TCT CAA GTC ATC TAC GAA   2700

 G   F   S   N   F   Q   A   F   A   T   D   S   S   E   Y   T   N   V     918
GGT TTC TCA AAC TTC CAA GCA TTT GCT ACA GAC AGC AGT GAA TAT ACA AAC GTA   2754

 V   I   A   Q   N   A   D   Q   F   K   Q   W   G   V   T   S   F   Q     936
GTC ATC GCT CAG AAT GCG GAC CAA TTT AAG CAA TGG GGT GTG ACA AGC TTC CAA   2808

 L   A   P   Q   Y   R   S   S   T   D   T   S   F   L   D   S   I   I     954
TTG GCA CCA CAA TAT CGT TCA AGT ACA GAT ACA AGT TTC TTG GAT TCA ATT ATT   2862

 Q   N   G   Y   A   F   T   D   R   Y   D   L   G   Y   G   T   P   T     972
CAA AAC GGG TAT GCA TTC ACG GAT CGT TAT GAC TTA GGT TAT GGC ACA CCG ACA   2916

 K   Y   G   T   A   D   Q   L   R   D   A   I   K   A   L   H   A   S     990
AAA TAT GGA ACT GCT GAT CAG TTG CGC GAT GCT ATT AAA GCC TTA CAT GCT AGC   2970

 G   I   Q   A   I   A   D   W   V   P   D   Q   I   Y   N   L   P   E    1008
GGT ATT CAA GCC ATT GCC GAT TGG GTG CCG GAC CAA ATT TAT AAT TTG CCA GAG   3024

 Q   E   L   A   T   V   T   R   T   N   S   F   G   D   D   D   T   D    1026
CAA GAA TTA GCT ACT GTC ACA AGA ACA AAT TCA TTT GGA GAT GAC GAT ACA GAT   3078

 S   D   I   D   N   A   L   Y   V   V   Q   S   R   G   G   G   Q   Y    1044
TCT GAT ATT GAC AAT GCC TTA TAT GTT GTA CAA AGT CGT GGG GGT GGT CAA TAT   3132

 Q   E   M   Y   G   G   A   F   L   E   E   L   Q   A   L   Y   P   S    1062
CAA GAG ATG TAT GGT GGT GCC TTC TTA GAA GAG TTA CAG GCA CTC TAT CCA TCC   3186

 L   F   K   V   N   Q   I   S   T   G   V   P   I   D   G   S   V   K    1080
CTA TTT AAA GTG AAT CAA ATC TCA ACT GGC GTT CCA ATT GAT GGC AGT GTA AAG   3240

 I   T   E   W   A   A   K   Y   F   N   G   S   N   I   Q   G   K   G    1098
ATT ACT GAG TGG GCG GCT AAG TAC TTC AAT GGC TCT AAC ATC CAA GGT AAA GGT   3294

 A   G   Y   V   L   K   D   M   G   S   N   K   Y   F   K   V   V   S    1116
GCT GGA TAC GTA TTG AAA GAT ATG GGT TCT AAT AAG TAC TTT AAG GTC GTT TCG   3348

 N   T   E   D   G   D   Y   L   P   K   Q   L   T   N   D   L   S   E    1134
AAC ACT GAG GAT GGT GAC TAC TTA CCA AAA CAG TTA ACT AAT GAT CTG TCA GAA   3402

 T   G   Y   K   G   E   L   E   G   K   P   I   P   N   P   L   L   G    1152
ACT GGC TAC AAG GGC GAG CTT GAA GGT AAG CCT ATC CCT AAC CCT CTC CTC GGT   3456

 L   D   S   T   R   T   G   H   H   H   H   H   H                        1165
CTC GAT TCT ACG CGT ACC GGT CAT CAT CAC CAT CAC CAT                       3495
```

FIGURE 3 (end)

DSR-S Core ΔA sequence

M G : thioredoxin tag
H H : 6xHis tag H H
T Q : protein of interest

```
M   G   S   D   K   I   I   H   L   T   D   D   S   F   D   T   D   V      18
ATG GGA TCT GAT AAA ATT ATT CAT CTG ACT GAT GAT TCT TTT GAT ACT GAT GTA    54

L   K   A   D   G   A   I   L   V   D   F   W   A   H   N   C   G   P      36
CTT AAG GCA GAT GGT GCA ATC CTG GTT GAT TTC TGG GCA CAC TGG TGC GGT CCG   108

C   K   M   I   A   P   I   L   D   E   I   A   D   E   Y   Q   G   K      54
TGC AAA ATG ATC GCT CCG ATT CTG GAT GAA ATC GCT GAC GAA TAT CAG GGC AAA   162

L   T   V   A   K   L   N   I   D   H   N   P   G   T   A   P   K   Y      72
CTG ACC GTT GCA AAA CTG AAC ATC GAT CAC AAC CCG GGC ACT GCG CCG AAA TAT   216

G   I   R   G   I   P   T   L   L   L   F   K   N   G   E   V   A   A      90
GGC ATC CGT GGT ATC CCG ACT CTG CTG CTG TTC AAA AAC GGT GAA GTG GCG GCA   270

T   K   V   G   A   L   S   K   G   Q   L   K   E   F   L   D   A   N     108
ACC AAA GTG GGT GCA CTG TCT AAA GGT CAG TTG AAA GAG TTC CTC GAC GCT AAC   324

L   A   G   S   G   S   G   D   D   D   D   K   L   A   L   M   G   F     126
CTG GCC GGC TCT GGA TCC GGT GAT GAC GAT GAC AAG CTC GCC CTT ATG GGC TTC   378

S   G   V   I   D   G   Q   I   M   T   F   D   Q   E   T   G   Q   E     144
TCT GGT GTG ATT GAT GGT CAA ATA ATG ACA TTT GAT CAG GAA ACA GGG CAA GAA   432

V   S   N   T   T   S   E   I   K   E   G   L   T   T   Q   N   T   D     162
GTT TCT AAC ACA ACT TCT GAA ATA AAA GAA GGT TTG ACG ACT CAA AAC ACG GAT   486

Y   S   E   H   N   A   A   H   G   T   D   A   E   D   F   E   N   I     180
TAT AGC GAA CAT AAT GCA GCC CAC GGT ACG GAT GCT GAG GAC TTT GAA AAT ATT   540

D   G   Y   L   T   A   S   S   W   Y   R   P   T   G   I   L   R   N     198
GAC GGC TAT TTA ACA GCT AGT TCA TGG TAT CGT CCA ACA GGT ATT TTA CGT AAC   594

G   T   D   W   E   P   S   T   D   T   D   F   R   P   I   L   S   V     216
GGA ACA GAC TGG GAA CCT TCT ACA GAT ACA GAT TTC AGA CCA ATA TTG TCA GTG   648

W   W   P   D   K   N   T   Q   V   N   Y   L   N   Y   M   A   D   L     234
TGG TGG CCA GAT AAG AAC ACC CAG GTC AAT TAT TTA AAT TAC ATG GCT GAT TTA   702

G   F   I   S   N   A   D   S   F   E   T   G   D   S   Q   S   L   L     252
GGG TTT ATC AGT AAT GCG GAC AGT TTT GAA ACT GGG GAT AGC CAA AGC TTA TTA   756

N   E   A   S   N   Y   V   Q   K   S   I   E   M   K   I   S   A   Q     270
AAT GAA GCA AGT AAC TAT GTT CAA AAA TCA ATT GAA ATG AAA ATT AGT GCG CAA   810

Q   S   T   E   W   L   K   D   A   M   A   A   F   I   V   A   Q   P     288
CAA AGT ACA GAG TGG TTA AAG GAT GCA ATG GCG GCC TTC ATT GTC GCG CAA CCA   864

Q   W   N   E   T   S   E   D   M   S   N   D   H   L   Q   N   G   A     306
CAG TGG AAT GAA ACT AGT GAA GAT ATG AGC AAT GAC CAT TTA CAA AAT GGC GCA   918

L   T   Y   V   N   S   P   L   T   P   D   A   N   S   N   F   R   L     324
TTA ACT TAT GTC AAC AGT CCA CTG ACA CCT GAC GCT AAT TCA AAC TTT AGA CTA   972

L   N   R   T   P   T   N   Q   T   G   E   Q   A   Y   N   L   D   N     342
CTT AAT CGG ACA CCA ACA AAC CAG ACT GGT GAA CAA GCG TAT AAT TTA GAT AAT  1026

S   K   G   G   F   E   L   L   L   A   N   D   V   D   N   S   N   P     360
TCA AAA GGT GGT TTT GAA TTG TTG TTA GCC AAT GAC GTT GAT AAT TCA AAC CCT  1080
```

FIGURE 4

```
V   V   Q   A   E   Q   L   N   W   L   Y   Y   L   M   N   F   G   T     378
GTA GTA CAA GCA GAA CAA TTG AAT TGG TTA TAT TAT TTA ATG AAT TTT GGT ACG  1134

I   T   A   N   D   A   D   A   N   F   D   G   I   R   V   D   A   V     396
ATT ACG GCC AAC GAC GCG GAT GCT AAT TTT GAT GGT ATT CGT GTA GAT GCA GTC  1188

D   N   V   D   A   D   L   L   Q   I   A   A   D   Y   F   K   L   A     414
GAC AAT GTG GAT GCT GAT TTG TTA CAA ATT GCT GCC GAT TAT TTC AAA CTA GCT  1242

Y   G   V   D   Q   N   D   A   T   A   N   Q   H   L   S   I   L   E     432
TAC GGT GTT GAT CAA AAT GAT GCT ACT GCT AAT CAG CAT CTT TCA ATT TTG GAA  1296

D   W   S   H   N   D   P   L   Y   V   T   D   Q   G   S   N   Q   L     450
GAT TGG AGT CAC AAT GAT CCT TTG TAT GTA ACA GAT CAA GGA AGC AAT CAA TTA  1350

T   M   D   D   Y   V   H   T   Q   L   I   W   S   L   T   K   S   S     468
ACC ATG GAT GAT TAT GTG CAC ACA CAA TTA ATC TGG TCT CTA ACA AAA TCA TCT  1404

D   I   R   G   T   M   Q   R   F   V   D   Y   Y   M   V   D   R   S     486
GAC ATA CGA GGT ACA ATG CAG CGC TTC GTG GAT TAT TAT ATG GTG GAT CGA TCT  1458

N   D   S   T   E   N   E   A   I   P   N   Y   S   F   V   R   A   H     504
AAT GAT AGT ACA GAA AAC GAA GCC ATT CCT AAT TAC AGC TTT GTA CGT GCA CAC  1512

D   S   E   V   Q   T   V   I   A   Q   I   V   S   D   L   Y   P   D     522
GAC AGC GAA GTG CAA ACG GTT ATT GCC CAA ATT GTT TCC GAT TTG TAT CCT GAT  1566

V   E   N   S   L   A   P   T   T   E   Q   L   A   A   A   F   K   V     540
GTT GAA AAT AGT TTA GCA CCA ACA ACA GAA CAA TTG GCA GCT GCT TTC AAA GTA  1620

Y   N   E   D   E   K   L   A   D   K   K   Y   T   Q   Y   N   M   A     558
TAC AAT GAA GAT GAA AAA TTA GCA GAC AAA AAG TAC ACA CAA TAT AAT ATG GCT  1674

S   A   Y   A   M   L   L   T   N   K   D   T   V   P   R   V   Y   Y     576
AGT GCT TAT GCG ATG TTG CTA ACC AAT AAG GAT ACT GTT CCT CGT GTC TAT TAT  1728

G   D   L   Y   T   D   D   G   Q   Y   M   A   T   K   S   P   Y   Y     594
GGC GAT TTA TAT ACA GAT GAT GGT CAA TAT ATG GCA ACA AAG TCA CCA TAC TAT  1782

D   A   I   N   T   L   L   K   A   R   V   Q   Y   V   A   G   G   Q     612
GAT GCG ATT AAC ACT TTG CTA AAG GCT AGA GTT CAG TAT GTT GCT GGT GGC CAA  1836

S   M   S   V   D   S   N   D   V   L   T   S   V   R   Y   G   K   D     630
TCG ATG TCC GTT GAT AGT AAT GAC GTG TTA ACA AGT GTT CGC TAT GGT AAA GAT  1890

A   M   T   A   S   D   T   G   T   S   E   T   R   T   E   G   I   G     648
GCC ATG ACA GCT TCT GAC ACT GGA ACA TCT GAG ACG CGT ACT GAA GGT ATT GGA  1944

V   I   V   S   N   N   A   E   L   Q   L   E   D   G   H   T   V   T     666
GTC ATC GTC AGC AAT AAC GCG GAG CTA CAA TTA GAG GAT GGG CAT ACT GTC ACA  1998

L   H   M   G   A   A   H   K   N   Q   A   Y   R   A   L   L   S   T     684
TTG CAT ATG GGG GCA GCT CAT AAG AAC CAA GCT TAT CGT GCT TTG TTA TCA ACA  2052

T   A   D   G   L   A   Y   Y   D   T   D   E   N   A   P   V   A   Y     702
ACT GCA GAT GGA TTA GCT TAT TAT GAT ACT GAT GAA AAT GCA CCT GTG GCG TAC  2106

T   D   A   N   G   D   L   I   F   T   N   E   S   I   Y   G   V   Q     720
ACA GAT GCT AAC GGC GAT TTG ATT TTT ACG AAT GAA TCA ATT TAT GGT GTA CAA  2160

N   P   Q   V   S   G   Y   L   A   V   W   V   P   V   G   A   Q   Q     738
AAT CCA CAA GTT TCT GGT TAC TTG GCA GTT TGG GTT CCG GTA GGT GCG CAA CAA  2214

D   Q   D   A   R   T   A   S   D   T   T   T   N   T   S   D   K   V     756
GAT CAA GAT GCA CGA ACG GCC TCT GAT ACA ACA ACA AAC ACG AGT GAT AAA GTG  2268

F   H   S   N   A   A   L   D   S   Q   V   I   Y   E   G   F   S   N     774
TTC CAT TCA AAC GCT GCT CTT GAT TCT CAA GTC ATC TAC GAA GGT TTC TCA AAC  2322

F   Q   A   F   A   T   D   S   S   E   Y   T   N   V   V   I   A   Q     792
TTC CAA GCA TTT GCT ACA GAC AGC AGT GAA TAT ACA AAC GTA GTC ATC GCT CAG  2376
```

FIGURE 4 (continued)

```
 N   A   D   Q   F   K   Q   W   G   V   T   S   F   Q   L   A   P   Q     810
AAT GCG GAC CAA TTT AAG CAA TGG GGT GTG ACA AGC TTC CAA TTG GCA CCA CAA   2430

 Y   R   S   S   T   D   T   S   F   L   D   S   I   I   Q   N   G   Y     828
TAT CGT TCA AGT ACA GAT ACA AGT TTC TTG GAT TCA ATT ATT CAA AAC GGG TAT   2484

 A   F   T   D   R   Y   D   L   G   Y   G   T   P   T   K   Y   G   T     846
GCA TTC ACG GAT CGT TAT GAC TTA GGT TAT GGC ACA CCG ACA AAA TAT GGA ACT   2538

 A   D   Q   L   R   D   A   I   K   A   L   H   A   S   G   I   Q   A     864
GCT GAT CAG TTG CGC GAT GCT ATT AAA GCC TTA CAT GCT AGC GGT ATT CAA GCC   2592

 I   A   D   W   V   P   D   Q   I   Y   N   L   P   E   Q   E   L   A     882
ATT GCC GAT TGG GTG CCG GAC CAA ATT TAT AAT TTG CCA GAG CAA GAA TTA GCT   2646

 T   V   T   R   T   N   S   F   G   D   D   D   T   D   S   D   I   D     900
ACT GTC ACA AGA ACA AAT TCA TTT GGA GAT GAC GAT ACA GAT TCT GAT ATT GAC   2700

 N   A   L   Y   V   V   Q   S   R   G   G   G   Q   Y   Q   E   M   Y     918
AAT GCC TTA TAT GTT GTA CAA AGT CGT GGG GGT GGT CAA TAT CAA GAG ATG TAT   2754

 G   G   A   F   L   E   E   L   Q   A   L   Y   P   S   L   F   K   V     936
GGT GGT GCC TTC TTA GAA GAG TTA CAG GCA CTC TAT CCA TCC CTA TTT AAA GTG   2808

 N   Q   I   S   T   G   V   P   I   D   G   S   V   K   I   T   E   W     954
AAT CAA ATC TCA ACT GGC GTT CCA ATT GAT GGC AGT GTA AAG ATT ACT GAG TGG   2862

 A   A   K   Y   F   N   G   S   N   I   Q   G   K   G   A   G   Y   V     972
GCG GCT AAG TAC TTC AAT GGC TCT AAC ATC CAA GGT AAA GGT GCT GGA TAC GTA   2916

 L   K   D   M   G   S   N   K   Y   F   K   V   V   S   N   T   E   D     990
TTG AAA GAT ATG GGT TCT AAT AAG TAC TTT AAG GTC GTT TCG AAC ACT GAG GAT   2970

 G   D   Y   L   P   K   Q   L   T   N   D   L   S   E   T   G   Y   K    1008
GGT GAC TAC TTA CCA AAA CAG TTA ACT AAT GAT CTG TCA GAA ACT GGC TAC AAG   3024

 G   E   L   E   G   K   P   I   P   N   P   L   L   G   L   D   S   T    1026
GGC GAG CTT GAA GGT AAG CCT ATC CCT AAC CCT CTC CTC GGT CTC GAT TCT ACG   3078

 R   T   G   H___H___H___H___H___H                                        1035
CGT ACC GGT CAT CAT CAC CAT CAC CAT                                       3105
```

FIGURE 4 (end)

DSR-S vardel Δ4N SEV663YDA mutant sequence

| | | | |
|---|---|---|---|
| M | G | : thioredoxin tag | ______ |
| H | H | : 6xHis tag | H H H |
| T | Q | : protein of interest | |
| D | | : catalytic amino acid | D |
| E | | | E |
| YDA | | : modified amino acids | YDA<br>- - - - |
| TC | | : modified bases | TC |

M G S D K I I H L T D D S F D T D V 18
ATG GGA TCT GAT AAA ATT ATT CAT CTG ACT GAT GAT TCT TTT GAT ACT GAT GTA 54

L K A D G A I L V D F W A H W C G P 36
CTT AAG GCA GAT GGT GCA ATC CTG GTT GAT TTC TGG GCA CAC TGG TGC GGT CCG 108

C K M I A P I L D E I A D E Y Q G K 54
TGC AAA ATG ATC GCT CCG ATT CTG GAT GAA ATC GCT GAC GAA TAT CAG GGC AAA 162

L T V A K L N I D H N P G T A P K Y 72
CTG ACC GTT GCA AAA CTG AAC ATC GAT CAC AAC CCG GGC ACT GCG CCG AAA TAT 216

G I R G I P T L L L F K N G E V A A 90
GGC ATC CGT GGT ATC CCG ACT CTG CTG CTG TTC AAA AAC GGT GAA GTG GCG GCA 270

T K V G A L S K G Q L K E F L D A N 108
ACC AAA GTG GGT GCA CTG TCT AAA GGT CAG TTG AAA GAG TTC CTC GAC GCT AAC 324

L A G S G S G D D D D K L A L M T Q 126
CTG GCC GGC TCT GGA TCC GGT GAT GAC GAT GAC AAG CTC GCC CTT ATG ACA CAA 378

Q V S G K Y V E K D G S W Y Y Y F D 144
CAA GTT AGC GGC AAG TAC GTT GAA AAA GAC GGT AGT TGG TAT TAT TAT TTT GAT 432

D G K N A K G L S T I D N N I Q Y F 162
GAT GGC AAA AAT GCT AAA GGT TTA TCA ACG ATA GAC AAC AAT ATT CAA TAT TTT 486

Y E S G K Q A K G Q Y V T I D N Q T 180
TAC GAG AGT GGT AAA CAA GCC AAA GGA CAG TAT GTC ACA ATT GAT AAT CAA ACA 540

Y Y F D K G S G D E L T G L Q S I D 198
TAT TAT TTT GAT AAG GGC TCA GGT GAT GAG TTA ACT GGT CTG CAA AGC ATT GAT 594

G N I V A F N D E G Q Q I F N Q Y Y 216
GGG AAC ATA GTT GCT TTT AAC GAT GAA GGG CAA CAA ATT TTT AAT CAA TAT TAC 648

Q S E N G T T Y Y F D D K G H A A T 234
CAA TCT GAA AAT GGT ACA ACA TAC TAC TTT GAT GAT AAA GGA CAC GCT GCT ACC 702

G I K N I E G K N Y Y F D N L G Q L 252
GGT ATT AAG AAT ATC GAG GGC AAA AAT TAT TAT TTT GAT AAT CTT GGG CAA CTA 756

K K G F S G V I D G Q I M T F D Q E 270
AAA AAA GGC TTC TCT GGT GTG ATT GAT GGT CAA ATA ATG ACA TTT GAT CAG GAA 810

T G Q E V S N T T S E I K E G L T T 288
ACA GGG CAA GAA GTT TCT AAC ACA ACT TCT GAA ATA AAA GAA GGT TTG ACG ACT 864

Q N T D Y S E H N A A H G T D A E D 306
CAA AAC ACG GAT TAT AGC GAA CAT AAT GCA GCC CAC GGT ACG GAT GCT GAG GAC 918

F E N I D G Y L T A S S W Y R P T G 324
TTT GAA AAT ATT GAC GGC TAT TTA ACA GCT AGT TCA TGG TAT CGT CCA ACA GGT 972

I L R N G T D W E P S T D T D F R P 342
ATT TTA CGT AAC GGA ACA GAC TGG GAA CCT TCT ACA GAT ACA GAT TTC AGA CCA 1026

FIGURE 5

```
I   L   S   V   W   W   P   D   K   N   T   Q   V   N   Y   L   N   Y     360
ATA TTG TCA GTG TGG TGG CCA GAT AAG AAC ACC CAG GTC AAT TAT TTA AAT TAC  1080

M   A   D   L   G   F   I   S   N   A   D   S   F   E   T   G   D   S     378
ATG GCT GAT TTA GGG TTT ATC AGT AAT GCG GAC AGT TTT GAA ACT GGG GAT AGC  1134

Q   S   L   L   N   E   A   S   N   Y   V   Q   K   S   I   E   M   K     396
CAA AGC TTA TTA AAT GAA GCA AGT AAC TAT GTT CAA AAA TCA ATT GAA ATG AAA  1188

I   S   A   Q   Q   S   T   E   W   L   K   D   A   M   A   A   F   I     414
ATT AGT GCG CAA CAA AGT ACA GAG TGG TTA AAG GAT GCA ATG GCG GCC TTC ATT  1242

V   A   Q   P   Q   W   N   E   T   S   E   D   M   S   N   D   H   L     432
GTC GCG CAA CCA CAG TGG AAT GAA ACT AGT GAA GAT ATG AGC AAT GAC CAT TTA  1296

Q   N   G   A   L   T   Y   V   N   S   P   L   T   P   D   A   N   S     450
CAA AAT GGC GCA TTA ACT TAT GTC AAC AGT CCA CTG ACA CCT GAC GCT AAT TCA  1350

N   F   R   L   L   N   R   T   P   T   N   Q   T   G   E   Q   A   Y     468
AAC TTT AGA CTA CTT AAT CGG ACA CCA ACA AAC CAG ACT GGT GAA CAA GCG TAT  1404

N   L   D   N   S   K   G   G   F   E   L   L   L   A   N   D   V   D     486
AAT TTA GAT AAT TCA AAA GGT GGT TTT GAA TTG TTG TTA GCC AAT GAC GTT GAT  1458

N   S   N   P   V   V   Q   A   E   Q   L   N   W   L   Y   Y   L   M     504
AAT TCA AAC CCT GTA GTA CAA GCA GAA CAA TTG AAT TGG TTA TAT TAT TTA ATG  1512

N   F   G   T   I   T   A   N   D   A   D   A   N   F   D   G   I   R     522
AAT TTT GGT ACG ATT ACG GCC AAC GAC GCG GAT GCT AAT TTT GAT GGT ATT CGT  1566

V   D   A   V   D   N   V   D   A   D   L   L   Q   I   A   A   D   Y     540
GTA GAT GCA GTC GAC AAT GTG GAT GCT GAT TTG TTA CAA ATT GCT GCC GAT TAT  1620

F   K   L   A   Y   G   V   D   Q   N   D   A   T   A   N   Q   H   L     558
TTC AAA CTA GCT TAC GGT GTT GAT CAA AAT GAT GCT ACT GCT AAT CAG CAT CTT  1674

S   I   L   E   D   W   S   H   N   D   P   L   Y   V   T   D   Q   G     576
TCA ATT TTG GAA GAT TGG AGT CAC AAT GAT CCT TTG TAT GTA ACA GAT CAA GGA  1728

S   N   Q   L   T   M   D   D   Y   V   H   T   Q   L   I   W   S   L     594
AGC AAT CAA TTA ACC ATG GAT GAT TAT GTG CAC ACA CAA TTA ATC TGG TCT CTA  1782

T   K   S   S   D   I   R   G   T   M   Q   R   F   V   D   Y   Y   M     612
ACA AAA TCA TCT GAC ATA CGA GGT ACA ATG CAG CGC TTC GTG GAT TAT TAT ATG  1836

V   D   R   S   N   D   S   T   E   N   E   A   I   P   N   Y   S   F     630
GTG GAT CGA TCT AAT GAT AGT ACA GAA AAC GAA GCC ATT CCT AAT TAC AGC TTT  1890

V   R   A   H   D   Y   D   A   Q   T   V   I   A   Q   I   V   S   D     648
GTA CGA GCT CAC GAC TAC GAC GCG CAA ACG GTT ATT GCC CAA ATT GTT TCC GAT  1944

L   Y   P   D   V   E   N   S   L   A   P   T   T   E   Q   L   A   A     666
TTG TAT CCT GAT GTT GAA AAT AGT TTA GCA CCA ACA ACA GAA CAA TTG GCA GCT  1998

A   F   K   V   Y   N   E   D   E   K   L   A   D   K   K   Y   T   Q     684
GCT TTC AAA GTA TAC AAT GAA GAT GAA AAA TTA GCA GAC AAA AAG TAC ACA CAA  2052

Y   N   M   A   S   A   Y   A   M   L   L   T   N   K   D   T   V   P     702
TAT AAT ATG GCT AGT GCT TAT GCG ATG TTG CTA ACC AAT AAG GAT ACT GTT CCT  2106

R   V   Y   Y   G   D   L   Y   T   D   D   G   Q   Y   M   A   T   K     720
CGT GTC TAT TAT GGC GAT TTA TAT ACA GAT GAT GGT CAA TAT ATG GCA ACA AAG  2160

S   P   Y   Y   D   A   I   N   T   L   L   K   A   R   V   Q   Y   V     738
TCA CCA TAC TAT GAT GCG ATT AAC ACT TTG CTA AAG GCT AGA GTT CAG TAT GTT  2214

A   G   G   Q   S   M   S   V   D   S   N   D   V   L   T   S   V   R     756
GCT GGT GGC CAA TCG ATG TCC GTT GAT AGT AAT GAC GTG TTA ACA AGT GTT CGC  2268

Y   G   K   D   A   M   T   A   S   D   T   G   T   S   E   T   R   T     774
TAT GGT AAA GAT GCC ATG ACA GCT TCT GAC ACT GGA ACA TCT GAG ACG CGT ACT  2322
```

FIGURE 5 (continued)

```
 E   G   I   G   V   I   V   S   N   N   A   E   L   Q   L   E   D   G     792
GAA GGT ATT GGA GTC ATC GTC AGC AAT AAC GCG GAG CTA CAA TTA GAG GAT GGG   2376

 H   T   V   T   L   H   M   G   A   A   H   K   N   Q   A   Y   R   A     810
CAT ACT GTC ACA TTG CAT ATG GGG GCA GCT CAT AAG AAC CAA GCT TAT CGT GCT   2430

 L   L   S   T   T   A   D   G   L   A   Y   Y   D   T   D   E   N   A     828
TTG TTA TCA ACA ACT GCA GAT GGA TTA GCT TAT TAT GAT ACT GAT GAA AAT GCA   2484

 P   V   A   Y   T   D   A   N   G   D   L   I   F   T   N   E   S   I     846
CCT GTG GCG TAC ACA GAC GCT AAC GGC GAT TTG ATT TTT ACG AAT GAA TCA ATT   2538

 Y   G   V   Q   N   P   Q   V   S   G   Y   L   A   V   W   V   P   V     864
TAT GGT GTA CAA AAT CCA CAA GTT TCT GGT TAC TTG GCA GTT TGG GTT CCG GTA   2592

 G   A   Q   Q   D   Q   D   A   R   T   A   S   D   T   T   T   N   T     882
GGT GCG CAA CAA GAT CAA GAT GCA CGA ACG GCC TCT GAT ACA ACA ACA AAC ACG   2646

 S   D   K   V   F   H   S   N   A   A   L   D   S   Q   V   I   Y   E     900
AGT GAT AAA GTG TTC CAT TCA AAC GCT GCT CTT GAT TCT CAA GTC ATC TAC GAA   2700

 G   F   S   N   F   Q   A   F   A   T   D   S   S   E   Y   T   N   V     918
GGT TTC TCA AAC TTC CAA GCA TTT GCT ACA GAC AGC AGT GAA TAT ACA AAC GTA   2754

 V   I   A   Q   N   A   D   Q   F   K   Q   W   G   V   T   S   F   Q     936
GTC ATC GCT CAG AAT GCG GAC CAA TTT AAG CAA TGG GGT GTG ACA AGC TTC CAA   2808

 L   A   P   Q   Y   R   S   S   T   D   T   S   F   L   D   S   I   I     954
TTG GCA CCA CAA TAT CGT TCA AGT ACA GAT ACA AGT TTC TTG GAT TCA ATT ATT   2862

 Q   N   G   Y   A   F   T   D   R   Y   D   L   G   Y   G   T   P   T     972
CAA AAC GGG TAT GCA TTC ACG GAT CGT TAT GAC TTA GGT TAT GGC ACA CCG ACA   2916

 K   Y   G   T   A   D   Q   L   R   D   A   I   K   A   L   H   A   S     990
AAA TAT GGA ACT GCT GAT CAG TTG CGC GAT GCT ATT AAA GCC TTA CAT GCT AGC   2970

 G   I   Q   A   I   A   D   W   V   P   D   Q   I   Y   N   L   P   E    1008
GGT ATT CAA GCC ATT GCC GAT TGG GTG CCG GAC CAA ATT TAT AAT TTG CCA GAG   3024

 Q   E   L   A   T   V   T   R   T   N   S   F   G   D   D   D   T   D    1026
CAA GAA TTA GCT ACT GTC ACA AGA ACA AAT TCA TTT GGA GAT GAC GAT ACA GAT   3078

 S   D   I   D   N   A   L   Y   V   V   Q   S   R   G   G   G   Q   Y    1044
TCT GAT ATT GAC AAT GCC TTA TAT GTT GTA CAA AGT CGT GGG GGT GGT CAA TAT   3132

 Q   E   M   Y   G   G   A   F   L   E   E   L   Q   A   L   Y   P   S    1062
CAA GAG ATG TAT GGT GGT GCC TTC TTA GAA GAG TTA CAG GCA CTC TAT CCA TCC   3186

 L   F   K   V   N   Q   I   S   T   G   V   P   I   D   G   S   V   K    1080
CTA TTT AAA GTG AAT CAA ATC TCA ACT GGC GTT CCA ATT GAT GGC AGT GTA AAG   3240

 I   T   E   W   A   A   K   Y   F   N   G   S   N   I   Q   G   K   G    1098
ATT ACT GAG TGG GCG GCT AAG TAC TTC AAT GGC TCT AAC ATC CAA GGT AAA GGT   3294

 A   G   Y   V   L   K   D   M   G   S   N   K   Y   F   K   V   V   S    1116
GCT GGA TAC GTA TTG AAA GAT ATG GGT TCT AAT AAG TAC TTT AAG GTC GTT TCG   3348

 N   T   E   D   G   D   Y   L   P   K   Q   L   T   N   D   L   S   E    1134
AAC ACT GAG GAT GGT GAC TAC TTA CCA AAA CAG TTA ACT AAT GAT CTG TCA GAA   3402

 T   G   F   T   H   D   D   K   G   I   I   Y   Y   T   L   S   G   Y    1152
ACT GGC TTT ACA CAC GAT GAT AAA GGA ATC ATC TAT TAT ACA TTA AGT GGT TAT   3456

 R   A   Q   N   A   F   I   Q   D   D   D   N   N   Y   Y   Y   F   D    1170
CGT GCC CAA AAT GCA TTT ATT CAA GAT GAT GAT AAT AAC TAT TAC TAT TTT GAT   3510

 K   T   G   H   L   V   T   G   L   Q   K   I   N   N   H   T   Y   F    1188
AAA ACA GGT CAT TTA GTA ACA GGT TTG CAA AAG ATT AAT AAC CAT ACC TAC TTC   3564

 F   L   P   N   G   I   E   L   V   K   S   F   L   Q   N   E   D   G    1206
TTC TTA CCT AAT GGT ATC GAA CTG GTC AAG AGC TTC TTA CAA AAC GAA GAT GGT   3618
```

FIGURE 5 (continued)

```
    T   I   V   Y   F   D   K   K   G   H   Q   V   F   D   Q   Y   I   T    1224
   ACA ATT GTT TAT TTC GAT AAG AAA GGT CAT CAA GTT TTT GAT CAA TAT ATA ACT   3672

    D   Q   N   G   N   A   Y   Y   F   D   D   A   G   V   M   L   K   S    1242
   GAT CAA AAT GGA AAT GCG TAT TAC TTT GAT GAT GCT GGT GTA ATG CTT AAA TCA   3726

    G   L   A   T   I   D   G   H   Q   Q   Y   F   D   Q   N   G   V   Q    1260
   GGG CTT GCA ACG ATT GAT GGA CAT CAA CAG TAT TTT GAT CAA AAT GGT GTG CAG   3780

    V   K   D   K   F   V   I   G   T   D   G   Y   K   Y   Y   F   E   P    1278
   GTT AAG GAT AAG TTT GTG ATT GGC ACT GAT GGT TAT AAG TAT TAC TTT GAA CCA   3834

    G   S   G   N   L   A   I   L   R   Y   V   Q   N   S   K   N   Q   W    1296
   GGT AGT GGT AAC TTA GCT ATC CTA CGT TAT GTG CAA AAT AGT AAG AAT CAA TGG   3888

    F   Y   F   D   G   N   G   H   A   V   T   G   F   Q   T   I   N   G    1314
   TTC TAT TTT GAT GGT AAT GGC CAT GCT GTC ACT GGT TTC CAA ACA ATT AAT GGT   3942

    K   K   Q   Y   F   Y   N   D   G   H   Q   S   K   G   E   F   I   D    1332
   AAA AAA CAA TAT TTC TAT AAT GAT GGT CAT CAA AGT AAA GGT GAA TTC ATT GAT   3996

    A   D   G   D   T   F   Y   T   S   A   T   D   G   R   L   V   T   G    1350
   GCA GAC GGG GAT ACT TTC TAT ACG AGT GCC ACT GAT GGT CGC CTA GTA ACT GGT   4050

    V   Q   K   I   N   G   I   T   Y   A   F   D   N   T   G   N   L   I    1368
   GTT CAG AAG ATT AAT GGT ATT ACC TAT GCT TTT GAT AAC ACA GGA AAT TTG ATC   4104

    T   N   Q   Y   Y   Q   L   A   D   G   K   Y   M   L   L   D   D   S    1386
   ACA AAT CAG TAT TAT CAA TTA GCA GAT GGT AAA TAT ATG TTG TTA GAT GAT AGT   4158

    G   R   A   K   T   G   F   V   L   Q   D   G   V   L   R   Y   F   D    1404
   GGT CGT GCG AAA ACA GGG TTT GTA TTG CAA GAT GGT GTA CTA AGA TAC TTC GAT   4212

    Q   N   G   E   Q   V   K   D   A   I   I   V   D   P   D   T   N   L    1422
   CAA AAC GGT GAG CAA GTG AAA GAT GCT ATC ATT GTG GAT CCA GAT ACT AAC TTG   4266

    S   Y   K   G   E   L   E   G   K   P   I   P   N   P   L   L   G   L    1440
   AGT TAC AAG GGC GAG CTT GAA GGT AAG CCT ATC CCT AAC CCT CTC CTC GGT CTC   4320

    D   S   T   R   T   G   H   H   H   H   H   H                            1452
   GAT TCT ACG CGT ACC GGT CAT CAT CAC CAT CAC CAT                           4356
```

FIGURE 5 (end)

CONSTRUCTION OF NEW VARIANTS OF DEXTRANSUCRASE DSR-S BY GENETIC ENGINEERING

SUBMISSION ON COMPACT DISC

The contents of the following submission on compact discs are incorporated herein by reference in its entirety: A compact disc copy of the Sequence Listing (COPY 1), (file name: B6624A.ST25, date recorded: Feb. 8, 2007, size: 152 KB); a duplicate compact disc copy of the Sequence Listing (COPY 2), (file name: B6624A.ST25, date recorded: Feb. 8, 2007, size: 152 KB); a computer readable form copy of the Sequence Listing (CRF COPY) (file name: B6624A.ST25, date recorded: Feb. 8, 2007, size: 152 KB).

The present invention relates to a recombinant process for the production of truncated and/or mutated dextransucrases while conserving their enzymatic activity and/or conserving their specificity for synthesizing α-1, 6 bonds. More precisely, the present invention relates to nucleic acid sequences of truncated or mutated dextransucrases, vectors containing said nucleic acid sequences and host cells transformed by sequences encoding truncated or mutated dextransucrases. In a further aspect, the invention concerns a method for producing, in a recombinant manner, truncated and/or mutated dextransucrases which conserve their enzymatic activity and/or conserve their specificity for synthesizing α-1, 6 bonds in the final product and methods for producing dextrans or isomalto-oligosaccharides, in a single step, with a controlled molar mass and dextrans with modified rheological properties, especially compared with the properties of dextrans obtained with the native enzyme.

FIELD OF THE INVENTION

Dextrans are α-D-glucans with various structures, comprising contiguous glycosyl units more than 50% of which have α-1,6 bonds in the principal chain and α-1,2, α-1,3 and/or α-1,4 branches [1]. The enzymes which produce such dextrans from sucrose are termed dextransucrases and belong to glycoside hydrolase family 70 [2]. During the reaction, fructose derived from the sucrose is released and may be upgraded elsewhere. Dextransucrases are produced by lactic bacteria from genera *Leuconostoc, Streptococcus* and *Lactobacillus [*1].

Dextransucrase (DSR-S) from *Leuconostoc mesenteroides* NRRL B-512F contains 1,527 amino acids [3]. This enzyme catalyzes the synthesis of glucose homopolymers with more than 95% α-1,6 bonds. The production of dextran may be redirected towards that of oligosaccharides or glucosylated conjugates by adding a suitable acceptor to the reaction mixture [4].

The number of industrial applications for dextrans and dextran derivatives is increasing, in particular for dextrans with a specific size. Dextrans with a size in the range 70,000 to 100,000 Da are, for example, used as a plasma substitute [5, 31]. Further, dextran of 40,000 Da is used to improve blood flow, most probably by reducing the viscosity of the blood and inhibiting erythrocytary aggregation [6,8]. After sulphation, smaller dextrans of about 10,000 daltons, for example, are used as transporters for iron [7] or anticoagulants [8]. Those compounds may have antiviral properties [9, 10].

Further, cross-linked dextran derivatives have long been used in the field of molecular separation; chromatography supports under the trade name Sephadex® have been sold since 1961 [6].

Moreover, the European Union has recently approved the use of dextran as a food ingredient in bakery products when these contain more than 95% of α-1,6 bonds and have a molar mass of more than $2\times10^6$ Da [15].

Dextransucrase may also produce isomalto-oligosaccharides (IMO) via an acceptor reaction. Acceptor reactions carried out by glucansucrases consist of a transfer of glucosyl residues from sucrose to other molecules added to the reaction medium. It is of increasing commercial interest, particularly in Japan, where the demand for isomalto-oligosaccharides represents about fifteen thousand tons per year [11]. Such small IMOs (DP 2 to 6) are used in bakery items, for drinks, in saké, in seasonings, in confectionery and as anti-cariogenic sweeteners. It has also been shown that said IMOs have prebiotic properties which are useful with respect to the intestinal and/or vaginal flora [12, 13]. These properties appear to vary with the size of the IMOs and are favored by high degrees of polymerization [14].

The only commercial and usual source of dextrans consists of cultivating *L. mesenteroides* NRRL B-512F with sucrose, leading to the formation of high molar mass polymers of about $10^8$ Da. The direct synthesis of smaller dextrans of 10000 to 100000 Da is currently impossible. Dextrans are currently produced conventionally by acid hydrolysis of high molar mass native polymers followed by fractionation using organic solvents. This second step is, however, renowned for its low yields [19].

From a commercial viewpoint, IMOs of DP 2 to 6 are not produced by an acceptor reaction with dextransucrase DSR-S and glucose due to the low reaction yields, but from starch hydrolysates and a mixture of α-amylases and glucosidases [11].

Monchois et al [16] describe carboxy-terminal deletions from the dextransucrase of *Leuconostoc mesenteroides* NRRL B-512F and conclude that the role of the C-terminal domain is to facilitate transfer of dextran and oligosaccharides beyond the active site.

U.S. Pat. No. 5,229,277 describes a process for producing dextran polymers having a homogeneous low molar mass using *Leuconostoc mesenteroides* and a mutant microorganism of *Lipomyces starkeyi* ATCC 74054, which is a yeast having dextranase activity, a specific enzyme for the hydrolysis of α-1,6 bonds of dextran. That method necessitates particular culture conditions and a precisely regulated duration and temperature so that the dextranase activity reduces the molar mass of the dextrans. Dextran polymers produced by that method have a molar mass in the range of 40,000 and 150,000 Da.

The foregoing shows that there is a need for the production of dextrans with a molar mass of about 10,000 to 100,000 Da using a faster method with a better yield, which in particular requires neither acid hydrolysis nor fractionation.

The present invention concerns dextransucrases produced in a recombinant manner, which are truncated and/or mutated, while conserving their enzymatic activity and/or conserving their specificity for synthesizing α-1,6 bonds, or truncated variants of dextransucrase which produce dextrans with a controlled molar mass. More precisely, they conserve the binding specificity of native DSR-S and/or conserve their specificity for synthesizing α-1,6 bonds and, starting from sucrose, produce high molar mass dextrans with interesting texturing properties and/or dextrans and IMOs with a controlled molar mass.

The present invention also pertains to providing nucleic acid sequences of truncated and/or mutated dextransucrase, vectors and host cells transformed by said vectors, and amino acid sequences of truncated and/or mutated dextransucrases.

In particular, as will become apparent from the Examples, certain dextransucrases produce polymers with interesting texturing properties, i.e., substantially superior to those of the polymer produced by the native enzyme; others produce dextrans and isomalto-oligosaccharides with a controlled molar mass. Isomaltose is produced by at least one truncated and mutated dextransucrase.

Further aspects of the present invention will become apparent from the following description and Examples or preferred implementations.

SUMMARY OF THE INVENTION

In a first aspect, the invention concerns a nucleotide sequence consisting essentially of or consisting of a nucleotide sequence according to FIG. 1 (SEQ ID NO: 1), a nucleotide sequence according to FIG. 2 (SEQ ID NO: 2), a nucleotide sequence according to FIG. 3 (SEQ ID NO: 3), a nucleotide sequence according to FIG. 4 (SEQ ID NO: 4), a nucleotide sequence according to FIG. 5 (SEQ ID NO: 5), a complementary sequence of one of the sequences with SEQ ID NO: 1, 2, 3, 4 or 5 or a sequence which hybridizes with a sequence with SEQ ID NO: 1, 2, 3, 4 or 5 under stringent hybridization conditions, provided that it conserves dextransucrase enzymatic activity.

In a further aspect, the invention concerns nucleotide sequences of dextransucrase consisting essentially of or consisting of a nucleotide sequence selected from the fragment of SEQ ID NO: 1 from position 373 to position 4269 (SEQ ID NO: 17), the fragment of sequence SEQ ID NO: 2 from position 373 to position 4005 (SEQ ID NO:18), the fragment of sequence SEQ ID NO: 3 from position 373 to position 3408 (SEQ ID NO:19), the fragment of sequence SEQ ID NO: 4 from position 373 to position 3018 (SEQ ID NO:20), and the fragment of sequence SEQ ID NO: 5 from position 373 to position 4269 (SEQ ID NO:21).

It also concerns nucleotide sequences consisting essentially of or consisiting of a nucleotide sequence selected from a complementary nucleotide sequence of the fragment of SEQ ID NO: 1 from the nucleotide at position 373 to that at position 4269, a complementary nucleotide sequence of the fragment of SEQ ID NO: 2 from the nucleotide at position 373 to that at position 4005, a complementary nucleotide sequence of the fragment of SEQ ID NO: 3 from the nucleotide at position 373 to that at position 3408, a complementary nucleotide sequence of the fragment of SEQ ID NO: 4 from the nucleotide at position 373 to that at position 3018 and a complementary nucleotide sequence to the fragment of SEQ ID NO: 5 from the nucleotide at position 373 to that at position 4269.

It also concerns nucleotide sequences which hybridize under stringent conditions with a nucleotide sequence selected from the fragment of sequence SEQ ID NO: 1 from position 373 to position 4269, the fragment of sequence SEQ ID NO: 2 from position 373 to position 4005, the fragment of sequence SEQ ID NO: 3 from position 373 to position 3408, the fragment of sequence SEQ ID NO: 4 from position 373 to position 3018 and the fragment of sequence SEQ ID NO: 5 from position 373 to position 4269, provided that it conserves dextransucrase enzymatic activity and said nucleotide sequences that hybridizes thereto has the same number of nucleotides and hybridizes over the full length of the fragment.

In yet another aspect, the present invention concerns nucleotide sequences encoding a protein consisting essentially of or consisting of consecutive amino acid sequences of any one of SEQ ID NOs:6 to 10 or 22 to 26.

In a still further aspect, the present invention concerns vectors, for example plasmids, and host cells transformed by said vectors and containing said sequence of nucleic acids from truncated and/or mutated dextransucrase, in particular the variants of the Examples.

In a still further aspect of the present invention, the present invention concerns a protein encoded by said truncated and/or mutated dextransucrase nucleotide sequence selected from the fragment of SEQ ID NO: 6 from the amino acid at position 125 to the amino acid at position 1423 (SEQ ID NO: 22), the fragment of SEQ ID NO: 7 from the amino acid at position 125 to the amino acid at position 1335 (SEQ ID NO: 23), the fragment of SEQ ID NO: 8 from the amino acid at position 125 to the amino acid at position 1136 (SEQ ID NO: 24), the fragment of SEQ ID NO: 9 from the amino acid at position 125 to the amino acid at position 1006 (SEQ ID NO: 25), and the fragment of SEQ ID NO: 10 from the amino acid at position 125 to the amino acid at position 1423 (SEQ ID NO: 26).

Further, the invention concerns a truncated and/or mutated dextransucrase consisting essentially of or consisting of one of the sequences described here, in particular selected from the fragment of SEQ ID NO: 6 from the amino acid at position 125 to the amino acid at position 1423 (SEQ ID NO:22), the fragment of SEQ ID NO: 7 from the amino acid at position 125 to the amino acid at position 1335 (SEQ ID NO:23), the fragment of SEQ ID NO: 8 from the amino acid at position 125 to the amino acid in position 1136 (SEQ ID NO:24), the fragment of SEQ ID NO: 9 from the amino acid at position 125 to the amino acid at position 1006 (SEQ ID NO:25), and the fragment of SEQ ID NO: 10 from the amino acid at position 125 to the amino acid at position 1423 (SEQ ID NO:26).

In a further aspect, the invention concerns the preparation of a mutated and/or truncated dextransucrase by culture of host cells containing a truncated and/or mutated dextransucrase under conditions allowing the expression of a dextransucrase, and isolating said dextransucrase from the culture medium.

The invention also concerns a method for producing dextrans and/or isomalto-oligosaccharides (IMO) with a controlled molar mass controlled by reacting a mutated and/or truncated dextransucrase of the invention with sucrose and optionally an acceptor, to obtain said dextrans or IMO with a controlled molar mass, including isomaltose.

A method for the direct production of IMOs essentially from sucrose also constitutes an aspect of the invention. The term "essentially" as used here means that it is not necessary for the acceptor to be employed in the reaction.

The high molar mass dextrans of the invention have modified rheological properties compared with those of dextran synthesized by a native enzyme, in particular a non-Newtonian, stringy and/or gelling nature.

Finally, the invention concerns compositions comprising dextrans obtained by using said dextransucrases and the use of said dextransucrases for the production of dextrans and isomalto-oligosaccharides with a controlled molar mass in the range of 342 and $10^9$ Da. More precisely, the invention produces (i) isomaltose (342 Da), (ii) isomalto-oligosaccharides of 342 to 5,000 Da, (iii) dextrans with a controlled size of 1,300 to 52,000 Da, more precisely 5,000 to 22,000 Da, and centered around 10,000 Da, (iv) dextrans with a controlled size of 7,000 to $1.7\times10^5$ Da, more precisely between 22,000 and 70,000 Da, centered around 40,000 Da.

BRIEF DESCRIPTION OF THE FIGURES

FIG. 1 shows the amino acid (SEQ ID NO: 6) and nucleotide sequence (SEQ ID NO: 1) of a truncated DSR-S vardel Δ4N dextransucrase with a thioredoxin tag in the 5' terminal position of the sequence and 6 histidine tags in the 3' terminal position of the sequence as well as spacer arms between the protein tags and the sequence coding for dextransucrase.

FIG. 2 shows the amino acid (SEQ ID NO: 7) and nucleotide sequence (SEQ ID NO: 2) of a truncated DSR-S vardel Δ3 with a thioredoxin tag in the 5' terminal position of the sequence and 6 histidine tags in the 3' terminal position of the sequence and spacer arms between the protein tags and the sequence coding for dextransucrase.

FIG. 3 shows the amino acid (SEQ ID NO: 8) and nucleotide sequence (SEQ ID NO: 3) of a truncated DSR-S vardel Core with a thioredoxin tag in the 5' terminal position of the sequence and 6 histidine tags in the 3' terminal position of the sequence and spacer arms between the protein tags and the sequence coding for dextransucrase.

FIG. 4 shows the amino acid (SEQ ID NO: 9) and nucleotide sequence (SEQ ID NO: 4) of a truncated DSR-S Core ΔA with a thioredoxin tag in the 5' terminal position of the sequence and 6 histidine tags in the 3' terminal position of the sequence and spacer arms between the protein tags and the sequence coding for dextransucrase.

FIG. 5 shows the amino acid (SEQ ID NO: 10) and nucleotides sequence (SEQ ID NO: 5) for a mutant DSR-S vardel Δ4N SEV663YDA with a thioredoxin tag in the 5' terminal position of the sequence and 6 histidine tags in the 3' terminal position of the sequence and spacer arms between the protein tags and the sequence coding for dextransucrase.

DETAILED DESCRIPTION OF THE PREFERRED EMBODIMENTS

Figure 6:
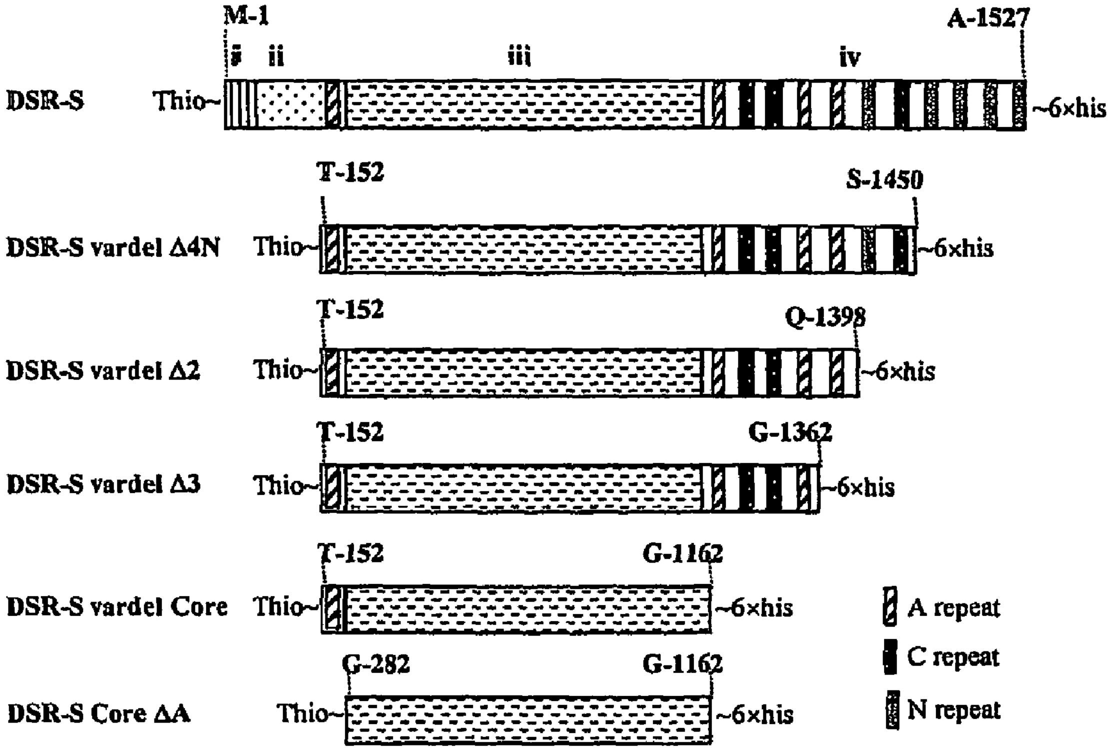
FIG. 6 is a diagrammatic representation of the truncated variants of DSR-S and their relative activity. The four different domains (i) to (iv) of DSR-S correspond to: (i) signal peptide, (ii) variable region; (iii) catalytic domain and (iv) C-terminal domain as well as the repeat units A, C and N (in the shaded boxes) located in accordance with Monchois et al, 1998 [16].

The term "enzyme having dextransucrase enzymatic activity" as used here means an enzyme which catalyzes the conversion of sucrose into oligosides and polyosides comprising more than 50% glucosyl units bound by α-1,6 bonds with a size in the range 342 and $10^9$ Da, and more particularly dextrans and isomalto-oligosaccharides comprising more than 95% α-1,6 bonds. This conversion may take place in the presence of absence of external acceptors such as maltose, glucose, isomaltose or fructose or isomalto-oligosaccharides. Maltose, isomaltose and glucose are the preferred acceptors in the present invention. The enzymatic activity of the dextransucrases of the present invention may be measured as described in the Examples.

The terms "nucleotides", "polynucleotides" "nucleic acids" and "oligonucleotides" as used here are interchangeable and include, without being limited thereto, RNA, DNA, DNA/RNA sequences comprising more than one nucleotide in a single chain or in the form of a double chain. The polynucleotide sequences of the present invention may be prepared by any known method including, without being limited thereto, any recombinant synthesis method and any ex vivo generation method, as well as combinations of those methods.

The term "truncated" as used here means that at least one of the N- or C-terminal ends of the amino acid or nucleic acid sequence has been shortened. That shortening may be carried out using restriction enzymes, proteolytic enzymes or synthetically, including by specific amplification of nucleotide sequences, in particular by PCR.

The term "purified dextransucrase" as used here means a dextransucrase which has only one active form of dextransucrase in the preparations, which has a degree of protein purity of at least 70% or 85% or 95%.

The term "interesting original texturizing property" as used here means the rheological properties of the dextrans of the invention which, compared with dextrans synthesized by native enzyme under the same conditions, for example, exhibit non-Newtonian behavior, especially a gel or stringy type behavior. A "gel type polymer" is characterized here by dynamic mode rheological measurements, detecting the energy conservation (G') and energy dissipation (G") moduli. For a gel, G' is higher than G" over the entire frequency range studied, as will become apparent in Example 5. The stringy character can be identified with the naked eye. The stringy dextrans of the invention change from solution type behavior to gel type behavior after application of a second series of shear stresses, as will also be seen in Example 5.

The following abbreviations used here have the following meanings: DSR-S for dextransucrase from *L. mesenteroides* NRRL B-512F; DP for degree of polymerization; HMW for "high molar mass", IMW for "intermediate molar mass", IMW polymers being highly polydispersed polymers with sizes in the range 1,000 to $10^7$ Da, where separation by HPSEC is difficult because of their low concentration. LMW polymers (low molar mass) are, according to the invention, a population which is much higher and easily detected between 750 and 70,000 Da, centered around 10,000 Da or in the range 2,000 to $1.7\times10^5$ Da and centered around 40,000 Da.

The term "10,000 Da dextran" as used here means a population of dextran with a size in the range 1,300 to 52,000 Da, more precisely between 5,000 and 22,000 Da, and centered at the height of the peak at about 10,000 Da. During characterization, the base of the elution peak obtained by gel permeation was in the range 1,300 to 52,000 Da, the range of molar mass estimated at the elution peak half height was in the range from 5,000 to 22,000 Da and the peak was centered at the height of the peak at about a mass of 10,000 Da. When the molar mass was expressed at the peak half height, at least 50% of the dextran population fell within the indicated range.

The term "40,000 Da dextran" as used here means a population of dextran with a size in the range 7000 to $1.7\times10^5$ Da, more precisely between 22,000 and 70,000 Da, and centered at the height of the peak at about 40,000 Da. During characterization, the base of the elution peak obtained by gel permeation was in the range 7,000 to $1.7\times10^5$ Da, the range of molar mass estimated at the elution peak half height was in the range 22,000 to 70,000 Da and the peak was centered at a mass of about 40,000 Da. When the molar mass was expressed at the peak half height, at least 50% of the dextran population fell within the indicated range.

IMO means isomalto-oligosaccharides.

The term "consisting essentially of" when used in connection with nucleic acids or amino acids as used here means that other minor ingredients or molecules may be present with the amino acid or nucleic acid sequences. The nucleic acid sequence has the exact same length as indicated in the sequence identification number, but may have 3 to 12 extra nucleotides at the N- and C-terminals. Like wise, the amino acid sequence has the exact same length as indicated in the sequence identification number but from 1 to 4 extra amino acids may be added at the N- or C-terminals. These extra amino acids have no effect on the enzyme activity.

More specifically, the present invention concerns nucleic acids which encode a truncated dextransucrase or a mutated dextransucrase, a sequence complementary to all or part of those sequences or a sequence which hybridizes under stringent conditions with one of the above sequences provided that dextransucrase enzymatic activity is maintained. It should be appreciated that the nucleotide sequences that hybridizes thereto has the same number of nucleotides and hybridizes over the full length of the fragment.

The term "stringent hybridization conditions" as used here means conditions as described by Sambrook et al, Molecular Cloning Manual, $3^{rd}$ edition (2001), i.e., as an example, the following conditions: hybridization buffers: 2×SSC, 10×Denhardts solution (Ficoll 400 & PEG & BSA, ratio 1:1:1), 0.1% SDS, 5 mM EDTA, 50 mM $Na_2HPO_4$, 250 μg/ml herring sperm DNA, 50 μg/ml of t-RNA or 0.25 M of sodium phosphate buffer with a pH of 7.2, 1 mM EDTA, 7% SDS;

Hybridization temperature: 60° C.;

Washing buffer 2×SSC, 0.1% SDS;

Washing temperature: 60° C.

The nucleic acid molecules which hybridize under stringent conditions with the nucleic acids of the present invention may in principle encode dextransucrases from any microorganism such as bacteria, gram positive bacteria and, in one aspect of the invention, bacteria from the genera *Leuconostoc, Streptococcus* or *Lactobacillus*.

The present invention concerns nucleic acids which encode dextransucrase proteins having at least 70% or 80% or 90% sequence identity with those of sequences SEQ ID NOs: 1 to SEQ ID NO: 5 and SEQ ID NOs 17 to 21: provided that the protein encoded by said sequences has dextransucrase enzymatic activity.

In another aspect, the present invention concerns nucleotide sequences encoding a protein consisting essentially of or consisting of consecutive amino acid sequences of any one of SEQ ID NOs:6 to 10 or 22 to 26.

In a further aspect of the invention, the sequences complementary to the sequences of the invention or sequences which hybridize with said sequences under stringent conditions, provided that dextransucrase enzymatic activity is maintained, are also included in the present invention.

Derivations from the basic nucleotide sequences SEQ ID NO: 1, SEQ ID NO: 2, SEQ ID NO: 3, SEQ ID NO: 4 or SEQ ID NO: 5), where the sequences are selected from the fragment of sequence SEQ ID NO: 1 from position 373 to position 4269, the fragment of sequence SEQ ID NO: 2 from position 373 to position 4005, the fragment of sequence SEQ ID NO: 3 from position 373 to position 3408, the fragment of sequence SEQ ID NO: 4 from position 373 to position 3018 and the fragment of sequence SEQ ID NO: 5 of a nucleotide in position 373 to position 4269, the sequences complementary to said sequences or sequences which hybridize with said sequences under stringent conditions provided that the dextransucrase enzymatic activity is maintained, may be produced by deletion, substitution, insertion or recombination, for example; the methods for carrying out said steps and transformations being well known in the art and described, for example, by Sambrook et al, supra.

It should be understood here that if any deletions, substitutions, insertions or recombinations of any of the sequences cited above take place, the proteins encoded by the sequences must maintain their dextransucrase enzymatic activity. Thus, 1 to 132, preferably 2 to 60 nucleotides, more preferably 15 to 36 nucleotides and still more preferably 12 to 27 nucleotides may be modified, for example, by deletion, substitution, insertion or recombination. According to the invention, 90%, preferably 95% of the nucleotides remain unchanged.

The dextransucrase enzymatic activity can be measured, as described in the method section and in the Examples of the present application.

The oligonucleotides which may be used as a probe or primer are, for example, SEQ ID NO: 1 to SEQ ID NO: 5 or nucleotide sequences selected from the fragment of sequence SEQ ID NO: 1 from position 373 to position 4269, the fragment of sequence SEQ ID NO: 2 from position 373 to position 4005, the fragment of sequence SEQ ID NO: 3 from position 373 to position 3408, the fragment of sequence SEQ ID NO: 4 from position 373 to position 3018 and the fragment of sequence SEQ ID NO: 5 from a nucleotide in position 373 to position 4269.

The length of the probes and primers can vary depending on their applications. In general, they must have at least 25 nucleotides and may comprise all of the dextransucrase sequences described, such as 3,896 nucleotides. The length can also vary to be in the range of 25 to 150 nucleotides, 25 and 800 nucleotides or 25 and 3000 nucleotides, for example.

The primers generally comprise 18 to 25 nucleotides in length, but may also be longer, depending on the envisaged application. Examples of primers which can be used in the present invention are:

```
GGC TTC TCT GGT GTG ATT      (SEQ ID NO: 11)
GAT CTG TCA GAA ACT GGC      (SEQ ID NO: 12)
ACA CAA CAA GTT AGC GGC      (SEQ ID NO: 13)
CCA GAT ACT AAC TTG AGT      (SEQ ID NO: 14)
TTC ATT GAT GCA GAC GGG      (SEQ ID NO: 15)
CAC GAC TAC GAC GCG CAA      (SEQ ID NO: 16)
```

It should be noted that the primers in the 5' and 3' terminal positions of the nucleotides encode the dextransucrase (SEQ ID NOs: 11 to 15) and the 5' and 3' side of the mutant sequence (SEQ ID NO: 16). However, a skilled person can use each of these sequences to produce primers or probes using consecutive nucleotides. Furthermore, these nucleotide sequences which are used as a probe may be tagged with radioactivity, enzymatic tagging, fluorescent tagging, in particular.

In order to genetically engineer the prokaryotic or eukaryotic cell, the nucleic acids of the present application or a portion of the nucleic acids of the present application may be introduced into plasmids that allow mutagenesis or modification of sequences by recombination of nucleotide sequences. Standard methods using these techniques are known to the skilled person and have been described by Sambrook et al, supra, in particular. The DNA fragments can also be connected to each other by adapters or links and suitable restriction enzymes can be used to remove certain DNA sequences. Methods such as mutagenesis, restriction after the restoration of primers or ligatures can be used to obtain the desired sequence with the appropriate insertions, deletions or necessary or desirable substitutions.

Furthermore, well defined tags coding for nucleic acids may be attached to the N- or C-terminal ends of the nucleic acid sequences of the present invention. They may be peptides such as poly-His, c-myc epitope or HA-tag or small proteins such as bacterial GST, MBP (maltose binding protein), thioredoxin, β-galactosidase, VSV-glycoprotein and the like.

Particular nucleic acids coding for other protein tags are His-tag, T7tag, S-tag, a “flag” peptide, trpE, avidin/streptavidin, staphylococcal A or G protein, dihydrofolate reductase, cellulose binding domains, polycysteine, polyphenylalanine and the like, which may also be used in the present invention.

According to one aspect of the present invention, a nucleic acid coding for a thioredoxin is fused to the N-terminal nucleic acid sequence. A nucleic acid coding for a 6×His tag is fused to the 3' end of the nucleic acid sequences.

The nucleic acids of the present invention may be linked to a transcription unit comprising (1) gene expression regulation elements such as promoters and amplifiers and (2) a coding or structural sequence which is transcribed into a mRNA and translated into the corresponding protein, and (3) appropriate initiation and termination signals.

A number of suitable expression control sequences are known in the art. General methods for expressing the recombinant protein are also known and exemplified in the document by R Kaufman, Methods in Enzymology 185, 537-566 (1990) [17].

The promoter regions which can be used in the vectors of the present invention include lacL, lacZ, T3, T7, gpt, lambda PR, tre and ara.

The present invention also concerns vectors, in particular plasmids, cosmids, viruses, bacteriophages and other vectors which are known in the genetic engineering field and which comprise the nucleic acid sequences of the present application in one aspect of the present invention, said vectors being plasmids and selected from DSR-S vardel Δ4N, DSR-S vardel Δ3, DSR-S vardel Core, DSR-S Core ΔA and DSR-S vardel Δ4N SEV663YDA.

The nucleic acids of the present invention may be expressed in prokaryotic or eukaryotic cells. Non-limiting examples of such cells which may be cited are VERO cells, HELA cells such as ATCC No CCL3, CHO cell lines such as ATCC CCL61, COS cells such as COS-7 and ATCC No CR cells: 1650, W138, BHK, HepG2, 3T3 such as ATCC No CRL6361, A549, PC12, K562, 293 cells, Sf9 cells such as ATCC No CRL 1711, Cv1 cells such as ATCC No CCL70 and JRKAT cells such as ATCC Tib152.

Non-limiting cells which can be used in the present application include strains of the prokaryotic host cells such as *Eschierichia coli Bacillus subtilis, Salmonella typhimurium* or strains of the genus *Pseudomonas, Streptomyces* and *Staphylococcus* or strains of eukaryotic host cells such as the parasites *Apicomplexan* (*Plasmodia, Toxoplasma, Cryptosporidia*), *Leishmania* or *Trypanosoma.*

Other appropriate cells may be used in the present invention and in particular include yeast cells such as *Saccharomyces*, for example *Saccharomyces cerevisiae* or *pombe, Pichia pastoris* and eukaryotic cells (plant cells, CHO cells and the like).

In a further aspect, the cells used for expressing nucleic acids of the present invention are *Escherichia coli* and strains selected, for example, from JM109, BL21(DE3)pLysS, TOP10 or Pir1. The INVsc strain of *Saccharomyces cerevisiae* may also be used.

The present invention concerns host cells transformed with the nucleic acid sequences described above or with a vector as described above and cells derived from transformed cells and containing the vector or the nucleic acid sequences described herein.

Examples of such host cells which may be cited are *Escherichia coli*, in which the truncated and/or mutated dextransucrase may be produced. The preparation of such host cells is known in the art.

Proteins and biologically active fragments of such proteins as well as mutated proteins which are encoded by the nucleic acid molecules of the present invention and their preparation methods also fall within the scope of the present invention.

Thus, the present invention concerns a method for preparing mutated and/or truncated dextransucrase, comprising the following steps:

(a) culturing host cells transformed with the nucleic acid sequences described above or with a vector as described above under conditions allowing the expression of a dextransucrase; and (b) isolating said dextransucrase from the culture medium.

More specifically, the nucleic acid sequences may be selected from SEQ ID NO: 1 from position 373 to position 4269, the fragment of sequence SEQ ID NO: 2 from position 373 to position 4005, the fragment of sequence SEQ ID NO: 3 from position 373 to position 3408, the fragment of sequence SEQ ID NO: 4 from precursor 373 to position 3018, and the fragment of sequence SEQ ID NO: 5 from position 373 to position 4269, complementary sequences of said sequences and sequences which hybridize with said sequences under stringent conditions, provided that dextransucrase enzymatic activity is maintained.

After being isolated, the dextransucrases of the present invention may also be purified. In this respect, the usual purification methods may be used such as precipitation, ion exchange chromatography, affinity chromatography, hydrophobic exchange chromatography, gel filtration, reverse phase HPLC, phase demixing and the like. In one aspect of the present invention, the mutated or truncated dextransucrases of the present invention may be purified using a resin charged with nickel, taking into account the existence of the thioredoxin and 6×His tag.

Another aspect of the present invention concerns dextransucrase proteins consisting essentially of or consisting of an amino acid sequence selected from SEQ ID NO: 6 to 10 or an amino acid sequence selected from the fragment of SEQ ID NO: 6 from the amino acid at position 125 to the amino acid at position 1423, the fragment of SEQ ID NO: 7 from the amino acid at position 125 to the amino acid at position 1335, the fragment of SEQ ID NO: 8 from the amino acid at position 125 to the amino acid at position 1136, the fragment of SEQ ID NO: 9 from the amino acid at position 125 to the amino acid at position 1006, and the fragment of SEQ ID NO: 10 from the amino acid at position 125 to the amino acid at position 1423.

A protein encoded by one of nucleotide sequences SEQ ID NO: 1 to SEQ ID NO: 5 or fragments of said sequences, as set forth above, is another embodiment of the present invention.

Homologous amino acid sequences, i.e., wherein the degree of similarity with the sequences defined above is sufficient for the enzymatic activity to be maintained, are also included in the subject matter of the present application. Thus, Blast and Fasta programs may be used to investigate similarity. Since it was demonstrated herein that it was possible to truncate the N- and C-terminal ends of dextransucrases, maintaining enzymatic activity, sequence similarity cannot be considered for just the single complete sequence, but also for the truncated sequences. The present invention thus concerns any sequence containing 80%, 90% or 98% sequence similarity with the complete sequence, but also those which would have 80%, 90% or 98% sequence similarity with one of the truncated sequences, provided that enzymatic activity is maintained.

More specifically, the present invention concerns sequences having a degree of similarity of the order of 90%, 95% or 98% similarity with SEQ ID NO: 6 to 10 or amino acid sequences selected from the fragment of SEQ ID NO: 6 from the amino acid at position 125 to the amino acid at position 1423, SEQ ID NO: 7 from the amino acid at position 125 to the amino acid at position 1335, SEQ ID NO: 8 from the amino acid at position 125 to the amino acid at position 1136, SEQ ID NO: 9 from the amino acid at position 125 to the amino acid at position 1006, and SEQ ID NO: 10 from the amino acid at position 125 to the amino acid at position 1423, provided that these proteins have the enzymatic activity of said dextransucrases. Clearly, the amino acid sequences with a specific identity defined above have a majority of conservative amino acid substitutions.

Conservative amino acid substitutions include amino acid substitutions of the same class. These classes comprise, for example, amino acids having uncharged polar side chains, such as Asn, Gln, Ser, Thr or Tyr; amino acids containing basic side chains, such as His, Lys or Arg; amino acids containing acidic side chains, such as Glu or Asp and amino acids containing non-polar side chains, such as Ala, Gly, Leu, Val, Ile, Phe, Cys or Trp.

Furthermore, concerning the enzymatic activity of dextransucrase with amino acid substitutions, this can be tested as set forth in the Examples, but the activity can also be evaluated by HPLC analyses or using the usual predictions concerning the way amino acid changes affect protein functions.

In a further aspect, since the amino acid sequences are indicated here, the protein may be synthesized using R B Merrifield's method, 1963 [20]. For this reason, the synthesized dextransucrase proteins constitute another aspect of the present invention.

The present invention also concerns mutant dextransucrases designated mutant SEV663YDA of DSR-S vardel Δ4N in which the serine, glutamic acid and valine in positions 663, 664 and 665 have been modified to tyrosine, aspartic acid and alanine respectively.

This mutant may be used to synthesize isomaltose from sucrose, using sucrose as the only substrate in a yield which is equivalent to that obtained when an acceptor, such as glucose is added to the reaction medium.

For this reason, the present invention concerns a method for producing isomaltose directly from sucrose, said method comprising reacting mutant dextransucrase with SEQ ID NO: 10 with sucrose, and producing isomaltose.

The fusion proteins containing a protein tag as described above also form part of the present invention. In this regard, the mutated and/or truncated proteins of the present invention may be fused with at least one protein tag.

The preparation of high molar mass dextrans (about $10^6$-$10^8$ Da) and with modified Theological properties compared with dextran synthesized by native DSR-S of *L. mesenteroides* NRRL B-512F using the truncated dextransucrase of the present invention is another aspect of the invention.

More specifically, microorganisms secreting dextransucrase or cellular extracts of microorganisms producing dextransucrase in an intracellular manner may be cultivated or used in a medium comprising sucrose, resulting in the synthesis of isomaltose (342 Da), (ii) isomalto-oligosaccharides of 342 to 5,000 Da, (iii) dextrans with a controlled size of 1,300 to 5,200 Da centered around 10,000 Da, (iv) dextrans with a controlled size of 7,000 to $1.7\times10^5$ Da centered around 40,000 Da, and (v) dextrans with a high molar mass from $2\times10^6$ Da to $10^9$ Da. These compounds may be isolated from the culture medium by conventional methods such as ultrafiltration, nanofiltration, alcoholic precipitation, liquid chromatography and the like.

Alternatively, the truncated and/or mutated dextransucrases described in the present invention may be purified and used in a method for producing dextrans with a controlled molar mass.

Thus, the invention concerns a method for producing dextrans and/or isomalto-oligosaccharides with a controlled molar mass, comprising reacting a mutated and/or truncated dextransucrase consisting essentially of or consisting of a sequence selected from nucleotide sequences SEQ ID NO: 6 to SEQ ID NO: 10 defined above with at least sucrose and optionally an acceptor.

The invention also concerns a method for producing isomaltose, the method comprising reacting a mutated and/or truncated dextransucrase with sequence SEQ ID NO: 10 essentially with sucrose. The invention also concerns a method for producing dextrans with interesting textural properties, the method comprising reacting a mutated and/or truncated dextransucrase with the sequence of SEQ ID NO: 6.

The invention also concerns dextrans and isomalto-oligosaccharides having the characteristics defined in the present application which may be obtained by the methods described here. These characteristic properties include the fact that high molar mass dextrans have non-Newtonian behavior and have the character of a gel or a stringy nature, and the property of changing form a solution type behavior to that of a gel after application of a second series of shear stresses.

As will become apparent in the Examples, advantageously, the different rheological properties may be obtained depending on whether the enzyme is purified or non-purified.

The enzymatically produced dextrans of the invention may be used as a support in the pharmaceutical industry, as a plasma substitute, additives in textiles or paints, in cosmetics and in the agroalimentary industry, as well as a texturing agent, for example as a substitute for gum Arabic or a gelling agent. The invention also concerns compositions comprising the dextrans and IMOs of the invention.

One important application of the dextrans and isomalto-oligosaccharides of the present application is their use as prebiotics. These products are not completely metabolized and are selectively fermented in the colon by appropriate bacterial species such as *Bifidobacteria* and *Lactobacilli.*

Oligosaccharides have traditionally been used for human or animal foodstuffs, in the pharmaceutical industries and in the cosmetics industry or as a sweetener, stabilizer or filler [21]. During the last fifteen years, a new field of activity has developed for the prebiotic properties of certain non digestible molecules [23]. Oligosaccharides as prebiotics are interesting with respect to their capacity to resist attack by digestive enzymes and to accentuate the growth of "healthy" bacteria, primarily Bifidobacteria and Lactobacilli, in the intestine. This concept has been stimulated by the emergence of commercial prebiotic products which have rapidly gained popularity. Oligomers such as fructo-oligosaccharides, lactulose, galacto-oligosaccharides, xylo-oligosaccharides, oligosaccharides extracted from soya or isomalto-oligosaccharides which are usually obtained by biological processes or by extraction from plants, are also promising. Currently, research in this field has centered on the production of novel oligosaccharide structures termed second generation prebiotics which should have novel physico-chemical properties and more specific biological activities [18].

In a further aspect, the present invention concerns a composition comprising a dextran obtained from a dextransucrase of the invention, and a pharmaceutically acceptable vehicle or a food quality vehicle.

The acceptable vehicle may, for example, be selected from adjuvants, salts and the like and the adjuvants may be selected from muramyl peptides, alum, montanide and the like. The mutated and/or truncated dextransucrases may be a purified protein, a protein produced in a recombinant manner or a synthetically produced protein.

Regarding the method for producing the dextrans and/or IMOs, preferred acceptors, when used, are glucose, isomaltose, maltose and isomalto-oligosaccharides.

Preferably, the method for producing isomalto-oligosaccharides with a controlled molar mass comprises reacting a mutated and/or truncated dextransucrase consisting of sequences SEQ ID NO: 7, 8, 9 or 10 essentially with sucrose. The degree of polymerization thus varies from 2 to 60 glucosyl units (DP2 to DP60).

The production reaction takes place at temperatures in the range 4° C. to 80° C., preferably 4° C. to 40° C.

Preferably, when the sequence is SEQ ID NO: 7, SEQ ID NO: 8 or SEQ ID NO: 9, the temperature is in the range 4° C. to 15° C., preferably 8° C. to 12° C., and more preferably the temperature is of the order of 10° C. for the production of dextrans with a controlled size. Further, for such sequences, the temperature is preferably in the range from about 8° C. to 25° C., more preferably on the order of 20° C. for IMO synthesis.

Furthermore, preferably when the sequence is SEQ ID NO: 6 or SEQ ID NO: 10, the temperature is in the range 15° C. to 45° C., preferably 517° C. to 30° C., and more preferably on the order of 20° C. to 25° C.

Further, the sucrose concentration is in the range 10 to 600 g/l, preferably 75 to 400 g/l, and more preferably 90 to 280 g/l.

When the sequence is SEQ ID NO: 7, SEQ ID NO: 8 or SEQ ID NO: 9, the concentration of sucrose in the medium is preferably on the order of 250 g/l.

Further, when the sequence is SEQ ID NO: 6 or SEQ ID NO: 10, the concentration of sucrose may be on the order of 100 g/l.

Further, as appropriate, the sucrose/acceptor weight ratio may be on the order of 0.5 to 12, preferably 1 to 4, more preferably about 2.

In the method of the invention, the dextransucrase is in the free form or immobilized on a support. Said immobilization may be effected by adsorption, inclusion or covalent binding, for example.

Finally, to carry out the method, the pH is in the range 3.0 to 10.0, preferably 4.0 to 7.0, more preferably 4.5 to 6.0 and still more preferably about 5.2.

Other aspects of the invention may become apparent from a study of the Examples below.

EXAMPLE 1

Construction of Variants

The pBad/TOPO Thiofusion vector (Invitrogen) was used for cloning and expressing truncated and/or mutated dsrS genes under the control of the L-arabinose promoter. It allows fusion of the gene to the 6×His tag at the C-terminal end, and to a thioredoxin tag at the N-terminal end.

For use as a matrix, genomic DNA from *L. mesenteroides* NRRL B-512F was extracted using the "Blood and Cell culture DNA maxi" kit (Qiagen). The strain is derived from the NCAUR collection, Peoria, Ill., USA.

One Shot TOP10 cells (Invitrogen) were used for expression of the truncated and/or mutated dsrS genes. The restriction enzymes were purchased from New England Biolabs and used in accordance with the manufacturer's instructions. DNA was purified using "QIAquick" (purification by PCR and gel extraction) and "QIAprep" (plasmid purification) kits from Qiagen.

The variants were constructed by PCR amplification of the DSR-S gene from genomic DNA from *L. mesenteroides* NRRL B-512F using the "Expand High fidelity" polymerase (Roche) and the following primers (given in the 5'→3' direction):

1 DSR-S vardel Δ4N was constructed using the pBad and DSR-S vardel primers: 454-acacaacaagttagcggcaagtacgttgaaaaagac-490 and PBad Δ4N: 4350-actcaagttagtatctggatccacaatgatagc-4317. It contained amino acids T152 to S1450 of DSR-S.

2 DSR-S vardel Δ3 was constructed using the PBad and DSR-S vardel primers: 454-acacaacaagttagcggcaagtacgttgaaaaagac-490 and PBad Δ3: 4086-cccgtctgcatcaatgaattcacc-4062. It contained amino acids T152 to G1362 of DSR-S.

3 DSR-S vardel Core was constructed using the PBad and DSR-S vardel primers: 454-acacaacaagttagcggcaagtacgttgaaaaagac-490 and PBad Core: 3489-gccagtttctgacagatcattagttaactg-3459. It contained amino acids T152 to G1162 of DSR-S.

4 DSR-S Core ΔA was constructed using the PBad DSR-S cat primers: 843-ggcttctctggtgtgattgatggtcaa-870 and PBad Core: 3489-gccagtttctgacagatcattagttaactg-3459. It contains amino acids G282 to G1162 of DSR-S.

5 The mutant DSR-S vardel Δ4N SEV663YDA was constructed by directed mutagenesis using the "mega primer" technique [33, 21] and DNA polymerase Pfu (Strategene). A first PCR reaction was carried out using the DSR-S vardel Δ4N plasmid matrix and the SEV663YDA primer pair: 1965-agctttgtac agctcacgactacgacgcgcaaacggtt-2004 and rev: 3447-gtcaccatcctcagtgttcaaacg-3422, comprising the BstBI restriction site (underlined). This PCR product was then used as a reverse mega primer in a second PCR with the forw primer: 1329-caaccacagtggaatgaaactagtc-1354 comprising the SpeI restriction site. This second PCR product was then digested with the two restriction enzymes SpeI and BstBI in accordance with the manufacturer's conditions (New England Biolabs) and cloned into the pBad DSR-S vardel Δ4N vector previously digested with the same enzymes. The SEV663YDA primer was designed to introduce a single restriction site to select positive clones (in this case, the SacI site).

The primary structure of each of the variants DSR-S vardel Δ4N, DSR-S vardel Δ3, DSR-S vardel Core and DSR-S Core ΔA is diagrammatically shown in FIG. 6.

EXAMPLE 2

Production of Variants in *E coli*

Cultures were carried out in a baffled Erlenmeyer flask on 2×YT medium buffered to a pH of 6.4 with 100 mN of Tris-HCl, DSR-S being known to be unstable under alkaline pH conditions [3].

Composition of Medium 2X YT:

| | |
|---|---|
| Bactotryptone | 16 g/l |
| Yeast extract | 10 g/l |
| NaCl | 5 g/l |
| Tris | 12.1 g/l |

*E. coli* TOP10 cells carrying pBad DSR-S vardel Δ4N and pBad DSR-S vardel Δ4N SEV663YDA plasmids were cultivated at 23° C. L arabinose induction was carried out when cell growth reached $OD_{600\ nm}$ of 0.2 with 0.002% (w/v) of inducer. Culturing was stopped when cell growth reached a plateau ($OD_{600nm}$ of about 3-3.5) before starting the cell lysis phase.

*E. coli* TOP10 cells carrying pBad DSR-S vardel Δ3, pBad DSR-S vardel Core and pBad DSR-S Core ΔA plasmids were brought to 16° C. Induction was carried out when the cell growth reached $OD_{600\ nm}$ of 0.2 with 0.005% (w/v) of L arabinose in the case of DSR-S vardel Δ3 and 0.02% (w/v) in the case of DSR-S vardel Core and DSR-S Core ΔA. Culturing was halted when the cell growth reached a plateau ($OD_{600\ nm}$ of about 2.5) before starting the cell lysis phase.

Following culture, the cells were recovered by centrifuging (8,000×g, 10 minutes, 4° C.), re-suspended and concentrated to an $OD_{600\ nm}$ of equivalent to 80 in a sodium acetate buffer 50 mM, pH 5.2, supplemented with 0.05 g/l of 1 mM $CaCl_2$ and phenylmethanesulfonyl fluoride (PMSF). Cell rupture was carried out by sonication. The preparations were then centrifuged once again (20,000×g, 30 min, 4° C.) to eliminate cellular debris and recover only the sonication supernatant.

The enzymatic activity of the extracts was measured using the dinitrosalicylic acid (DNS) method of Sumner and Howell, 1935 [22]. An enzymatic unit is defined as the quantity of enzyme which catalyses the formation of one μmole of fructose per minute at a given temperature (4° C. to 40° C. depending on the case, more precisely 20° C. or 30° C.) and in a sodium acetate buffer (50 mM), pH 5.2, containing 0.05 g/l of $CaCl_2$ and 100 g/l of sucrose.

EXAMPLE 3

Purification of DSR-S Vardel Δ4N Variant

Figure 7A:
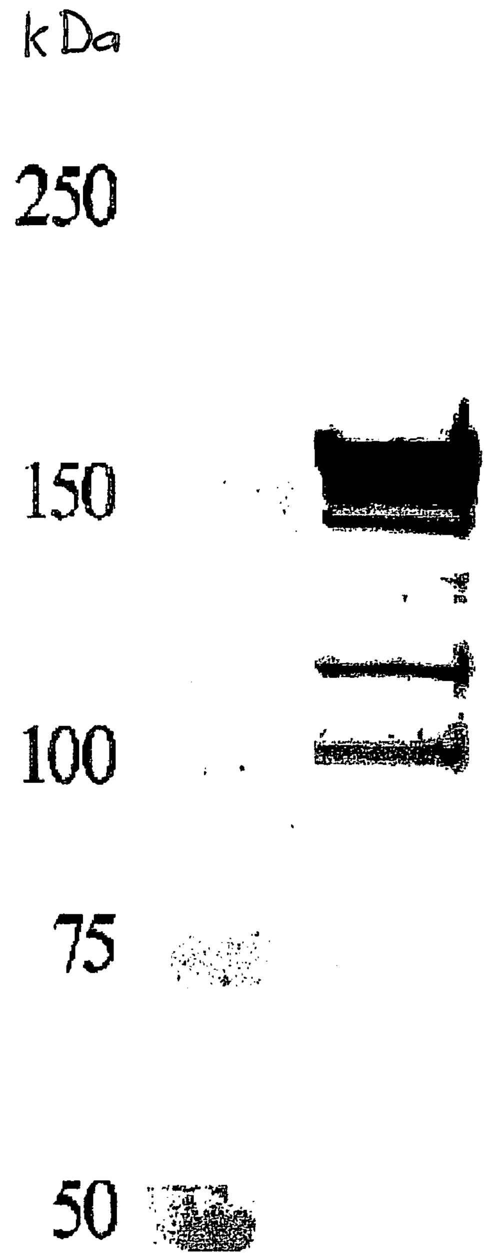
FIGS. 7 (A, B) shows anti-thioredoxin (A) and anti-6×His (B) Western blots carried out on a DSR-S vardel Δ4N produced by *E. coli* TOP10 at 23° C.
Figure 7B:
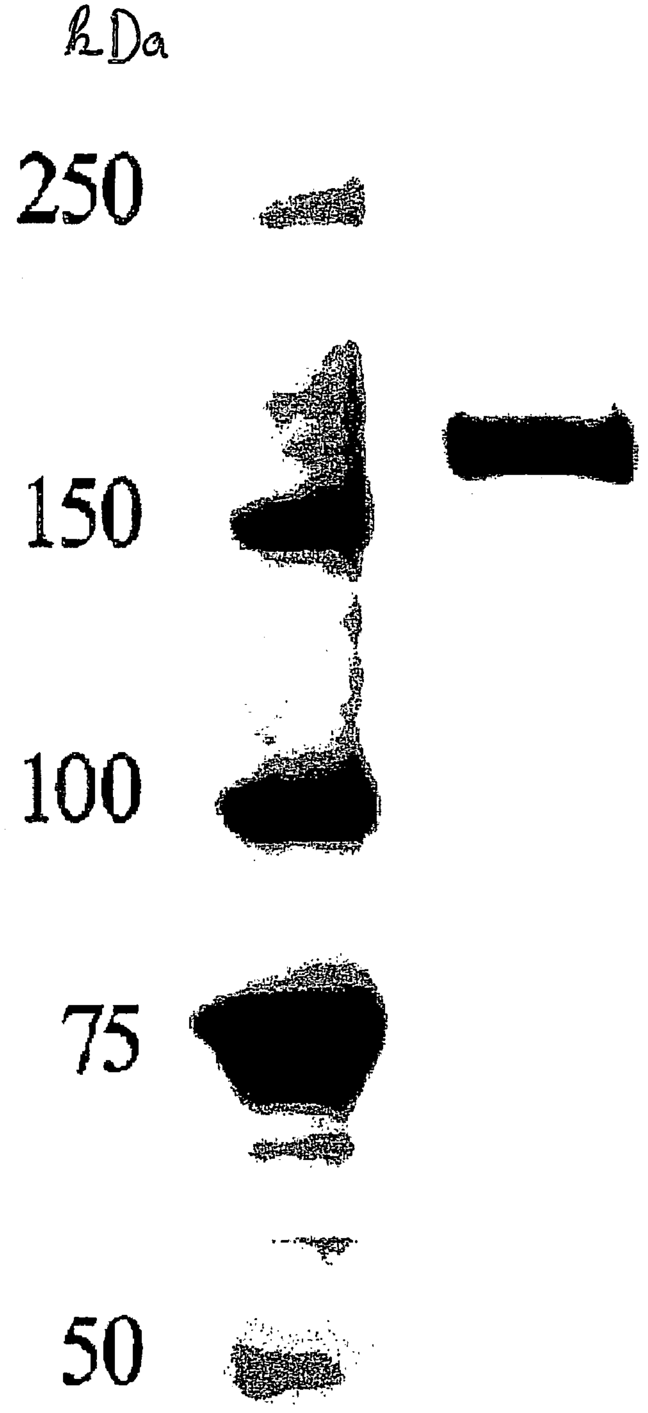

Different enzymatic forms of DSR-S vardel Δ4N were produced during the culture of *E. coli* TOP10: a vastly major entire form and different degraded forms at the C-terminal end (FIG. 7). The origin of these degradations remains unclear. Production in Example 2 reached about 5500 U/l of culture in the sonication supernatants (activity assayed at 30° C.).

To determine the number of active enzymatic forms in the extracts, electrophoresis gels were produced under native or denaturing conditions. After gel re-naturing, it was incubated overnight at 25° C. in a sodium acetate buffer, 50 mM, pH 5.2 supplemented with 100 g/l of sucrose. The active enzymatic forms then synthesized polymer at the region to which they migrated in the gel. A reagent (Schiff's reagent) which specifically colored the polymers synthesized by active dextransucrases, after oxidation of primary alcohol functions of the periodic acid polymer was used and the gels were stained with this reagent. This type of gel is termed a zymogram. In the case of DSR-S vardel Δ4N, or its mutant SEV663YDA, only the two higher molar mass forms were detected as being active (results not shown). However, only the entire form had both the thioredoxin tag and the 6×His tag.

The presence of the 6×His tag only in the entire form of DSR-S vardel Δ4N was exploited to purify the enzyme by affinity chromatography on nickel resin (Probond Ni-NTA, Invitrogen).

Purification was carried out at 4° C. All of the buffers had concentrations of 50 mM sodium acetate, 400 mM of NaCl, different concentrations of imidazole and were adjusted to a pH of 7.5. The resin was equilibrated with 8 volumes of buffer having a concentration of 40 mM of imidazole. Fixing was carried out for 2 hours with 7 volumes of enzymatic extract supplemented with 20 mM of imidazole and adjusted to a pH of 7.5. Next, the resin was washed with 40 volumes of 40 mM imidazole buffer, 8 volumes at 60 mM and 4 volumes at 100 mM. Finally, the proteins were eluted with 7 volumes of buffer having a concentration of 250 mM of imidazole.

The fractions containing the eluted fusion proteins were mixed and dialyzed overnight at 4° C. against a buffer containing a concentration of 50 mM of sodium acetate, pH of 5.2, and 0.05 g/l of $CaCl_2$. The protein concentration was determined by the microbradford method (Biorad Laboratories) with BSA (bovine serum albumin) as the standard.

Figure 8:
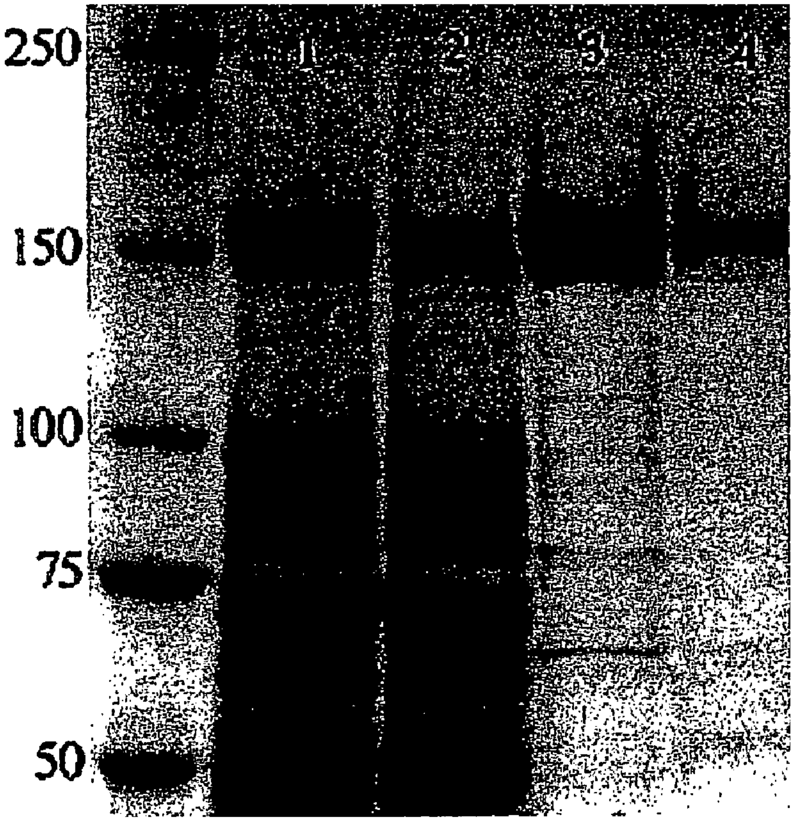
FIG. 8 shows an electrophoresis gel after staining the proteins with colloidal blue on DSR-S vardel Δ4N extracts during affinity purification on nickel resin (Probond, Invitrogen). Track 1 corresponds to the supernatant from sonication of *E. coli* TOP10 at the end of culture; track 2 corresponds to the effluent obtained after binding the tagged 6×His proteins on the resin, track 3 corresponds to the elution fraction and track 4 corresponds to the elution fraction after eliminating aggregates.

The purity of the preparation at the end of the procedure was estimated at about 90% (FIG. 8). The purified DSR-S vardel Δ4N proteins had a very strong tendency to aggregate, causing the formation of white precipitates and limiting the yields obtained at the end of the procedure (Table 1). However, the specific activity of the preparation was estimated at 584 U/mg of protein, which corresponded to the best described specific activity of a recombinant dextransucrase. By way of comparison, the specific activity of native DSR-S (expressed by *L. mesenteroides* NRRL B-512F) was estimated at about 170 U/mg [24].

TABLE 1

Purification of DSR-S vardel Δ4N by affinity chromatography on nickel resin

| Purification stage | Volume (ml) | Activity (U/ml) | Protein conc (mg/l) | Specific activity (U/mg) | Purification factor | Yield (%) |
|---|---|---|---|---|---|---|
| Sonication supernatants | 150 | 149.2 | 9.46 | 15.7 | 1 | 100 |
| Elution fraction after dialysis | 150 | 67.6 | 0.25 | 270.5 | 17 | 45.3 |
| Soluble fraction after eliminating aggregates | 150 | 38.2 | 0.09 | 424.4 | 27 | 25.4 |

EXAMPLE 4

Nucleotide Sequences and Amino Acid Sequences

The constructs were sequenced and the corresponding sequences are shown in FIGS. 1 to 5.

EXAMPLE 5

Synthesis of Dextran by DSR-S Vardel Δ4N, Comparison with DSR-S from *L. mesenteroides* NRRL B-512F Dextran was synthesized from native DSR-S from *L. mesenteroides* NRRL B-512F, entire recombinant DSR-S (sonication supernatant) and DSR-S vardel Δ4N (sonication supernatant and purified enzyme).

Synthesis Conditions and Analysis of Products Formed

Entire recombinant DSR-S was constructed on the same principle as the variants described in Example 1, with primers which were suitable for amplification of the entire gene. *E. coli* TOP10 cells carrying the pBad DSR-S plasmid were cultivated using the protocol described for DSR-S vardel Δ4N (Example 2). The supernatant contained three enzymatic forms, including two with higher active molar mass.

The form with the greatest size contained DSR-S in its entirety; the two other forms were degraded at their N-terminal position (data not shown).

The activity of each enzymatic preparation was determined at 30° C.

Dextran syntheses were carried out at 25° C. starting with a 100 g/l sucrose solution, in a 50 mM sodium acetate buffer containing 0.05 g/l of $CaCl_2$ and with 1 unit per ml of enzyme. The progressive exhaustion of sucrose was monitored by HPAEC-PAD analyses (see below) and the reaction was stopped after its complete consumption, by heating for 5 min at 95° C. (complete denaturing of cited dextransucrases).

The products formed were analyzed by HPAEC-PAD (high performance anion exchange chromatography with pulsed amperometric detection) with respect to the mono, di and oligosaccharides, and by HPSEC (high performance size exclusion chromatography) with respect to the polysaccharides.

The HPAEC-PAD system comprised a Dionex "Carbopack PA100" 4×250 mm column. A 6 to 300 mM sodium acetate gradient in 28 minutes in a 150 mM sodium hydroxide solution was applied at a flow rate of 1 ml/min. Detection was carried out by amperometry using a Dionex ED40 module with a gold electrode and an Ag/AgCl pH reference electrode.

The HPSEC system was constituted by two Shodex OH-Pack SB-805 and SB-802.5 columns in series, using 0.45 M sodium nitrate+1% (v/v) ethylene glycol as the solvent, in an amount of 0.3 ml/min. The columns and pre-columns were kept at 70° C. and the samples were filtered on 0.45 μm filters (Sartorius) prior to injection. Detection was of the refractometric type, coupled to a light diffusion detector (Wyatt) to determine the mass of the dextrans.

The concentrations by weight of glucose, fructose and leucrose (sucrose isomer) were determined by HPAEC-PAD analyses. The percentages of glucosyl residues from the sucrose incorporated into the free glucose and leucrose were calculated using the following formula:

$$\% \, G_{glucose} = [\text{glucose}_{tf}] / ([\text{sucrose}_{t0}] \times (180/342))$$

and $$\% G_{leucrose} = [leucrose_{tf}]/[sucrose_{t0}]$$

where [$glucose_{tf}$] and [$leucrose_{tf}$] correspond to the final concentrations of glucose and leucrose at the end of the reaction and [$sucrose_{t0}$] corresponds to that of the initial substrate (g/l).

The percentage of glucosyl residues incorporated into the HMW polymer was determined by HPSEC analyses using the formula:

$$\% G_{dextran} = \text{surface area}_{dextran\text{-}tf} / (\text{surface area}_{sucrose\text{-}t0} / (162/342))$$

in which surface $\text{area}_{dextran\ tf}$ corresponds to the surface area of the dextran peak, determined using the HPSEC chromatogram at the end of the reaction, and surface $\text{area}_{sucrose\text{-}t0}$ corresponds to that of the peak of the initial substrate. For a given concentration, the surface obtained by refractometry is identical regardless of the sugar.

The proportion of glucosyl units incorporated into the IMW polymers or oligosaccharides for which the concentration could not be directly quantified by HPAEC-PAD or HPSEC was determined using the formula:

$$\% G_{IMW} = 100 - \% G_{glucose\text{-}tf} - \% G_{leucrose\text{-}tf} - \% G_{dextan\text{-}tf}$$

Figure 9:
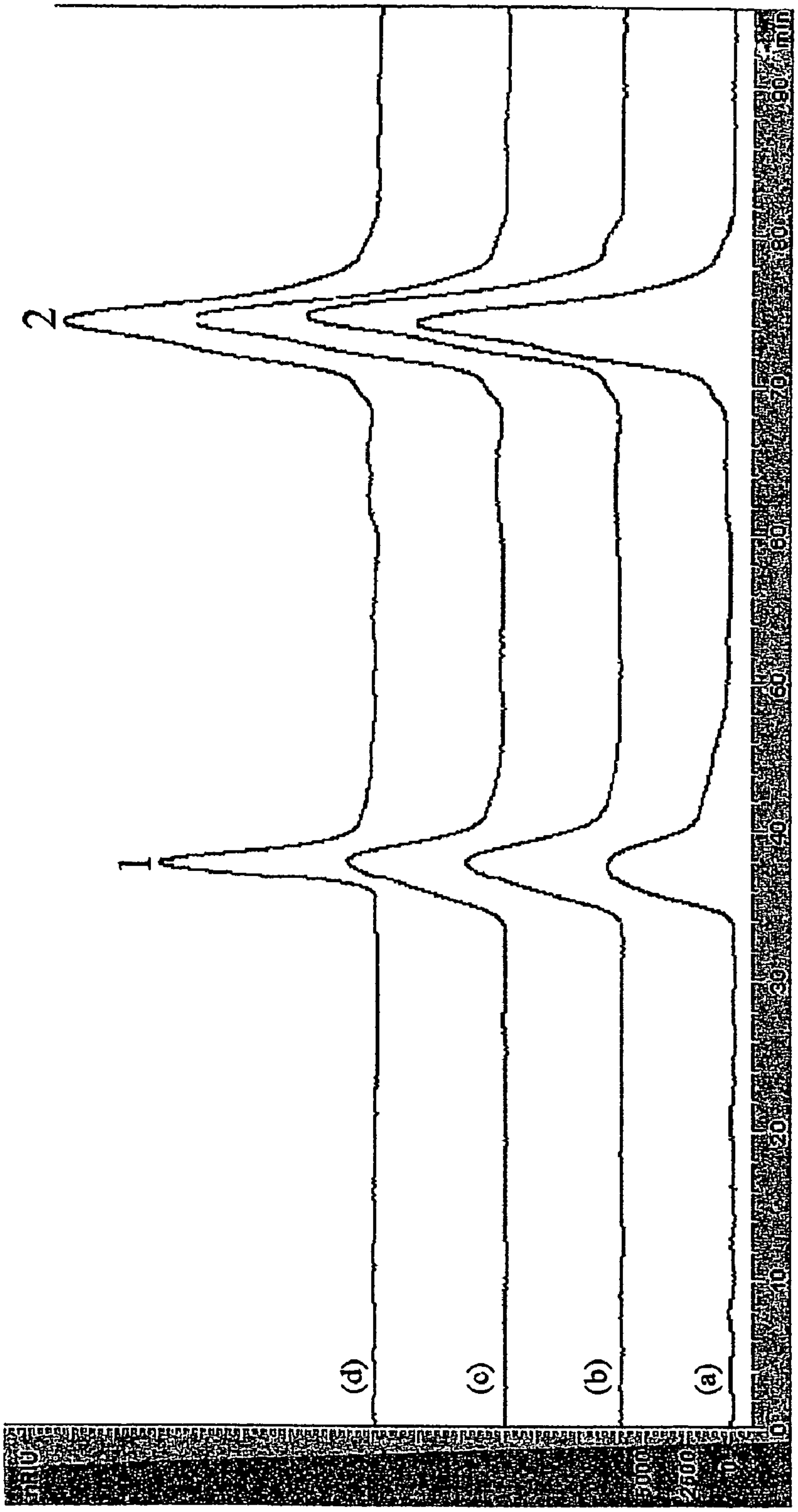
FIG. 9 shows the elution profiles obtained by HPSEC of dextrans produced by the preparation of a) native DSR-S from *L. mesenteroides* NRRL B-512F, b) entire recombinant DSR-S, c) DSR-S vardel Δ4N before purification and d) purified DSR-S vardel Δ4N. Peak 1 corresponds to the high molar mass polymer (HMW), peak 2 to fructose, glucose and oligosaccharides with a DP of less than 7, not separated by the system. Between those two peaks, perturbations of the base line reflect the presence of dextrans with an intermediate size (between $10^3$ to $10^7$ Da) in a very low concentration.

The elution profiles of the four dextrans obtained by HPSEC are shown in FIG. 9. Different populations can be distinguished: a first peak eluted at 38 minutes, corresponding to the high molar mass polymer (HMW), and a second peak at 75 minutes corresponding to fructose, glucose, leucrose (5-O-α-D glucosyl fructose) and other oligosaccharides with a degree of polymerization (DP) of less than 7, not separated by the system or in very low concentrations. Between these two principal peaks, as indicated by the base line perturbations, the products of intermediate size (IMW dextrans) were also present. These compounds, with very variable sizes, between 1000 and $10^7$ Da, were highly polydispersed and in very low concentrations, which explains their low intensity on the chromatogram. HPAEC-PAD analyses confirmed their presence, however (results not shown).

The relative quantity of glucosyl units derived from sucrose and incorporated into the different products is listed below in Table 2. The synthesis yield for HMW dextran represents about 60% of the glucosyl units for each of the preparations. The transfer of glucosyl units to water (glucose) or fructose (leucrose) represents less than 8%, while the synthesis of intermediate size dextrans (IMW) accounted for 25% to 32% of the transferred glucosyl units. All of the recombinant forms of DSR-S tended to synthesize more intermediate size dextrans. The HPSEC analyses also showed that the native enzyme appeared to synthesize two different populations of dextran, as opposed to only one for the recombinant enzymes. The molar mass of HMW dextrans was determined by light diffusion and estimated to be over $10^7$ g/mol for all of the samples (exclusion limit of the columns used).

TABLE 2

Percentage of glucosyl units incorporated into the various products derived from the synthesis of dextran at 25° C. and 100 g/l of sucrose, for the four cited DSR-S preparations

| | Glucose | Leucrose | IMW dextrans | HMW dextrans Rel % | HMW dextrans HMW (g/mol) |
|---|---|---|---|---|---|
| Native | 4.12 | 5.80 | 25.60 | 64.47 | $1.5 \times 10^8$ |
| DSR-S | | | | | $8.88 \times 10^7$ |
| Entire DSR-S | 2.32 | 5.39 | 29.32 | 62.96 | $1.86 \times 10^8$ |
| DSR-S vardel Δ4N | 2.43 | 5.90 | 31.03 | 60.64 | $4.87 \times 10^7$ |
| Purified DSR-S vardel Δ4N | 2.33 | 5.80 | 32.24 | 59.62 | $2.47 \times 10^7$ |

Structure of Dextrans Formed

The structure of the dextran produced by DSR-S vardel Δ4N (purified or otherwise) was compared with that of dextrans synthesized from entire recombinant DSR-S and native DSR-S. These structures were determined by nuclear magnetic resonance ($^1$H NMR) using a Brücker AC 300, at 85° C. and with an acquisition frequency of 300.13 MHz. The acquisition time was 3 s, with 32 to 64 passes. The dextrans were initially separated from the co-produced fructose by precipitating 3 times with 1 volume of absolute ethanol, recovered by centrifuging, washed with distilled water and freeze dried. The samples were dissolved in $D_2O$ to a concentration of 6 mg/ml.

Figure 10:
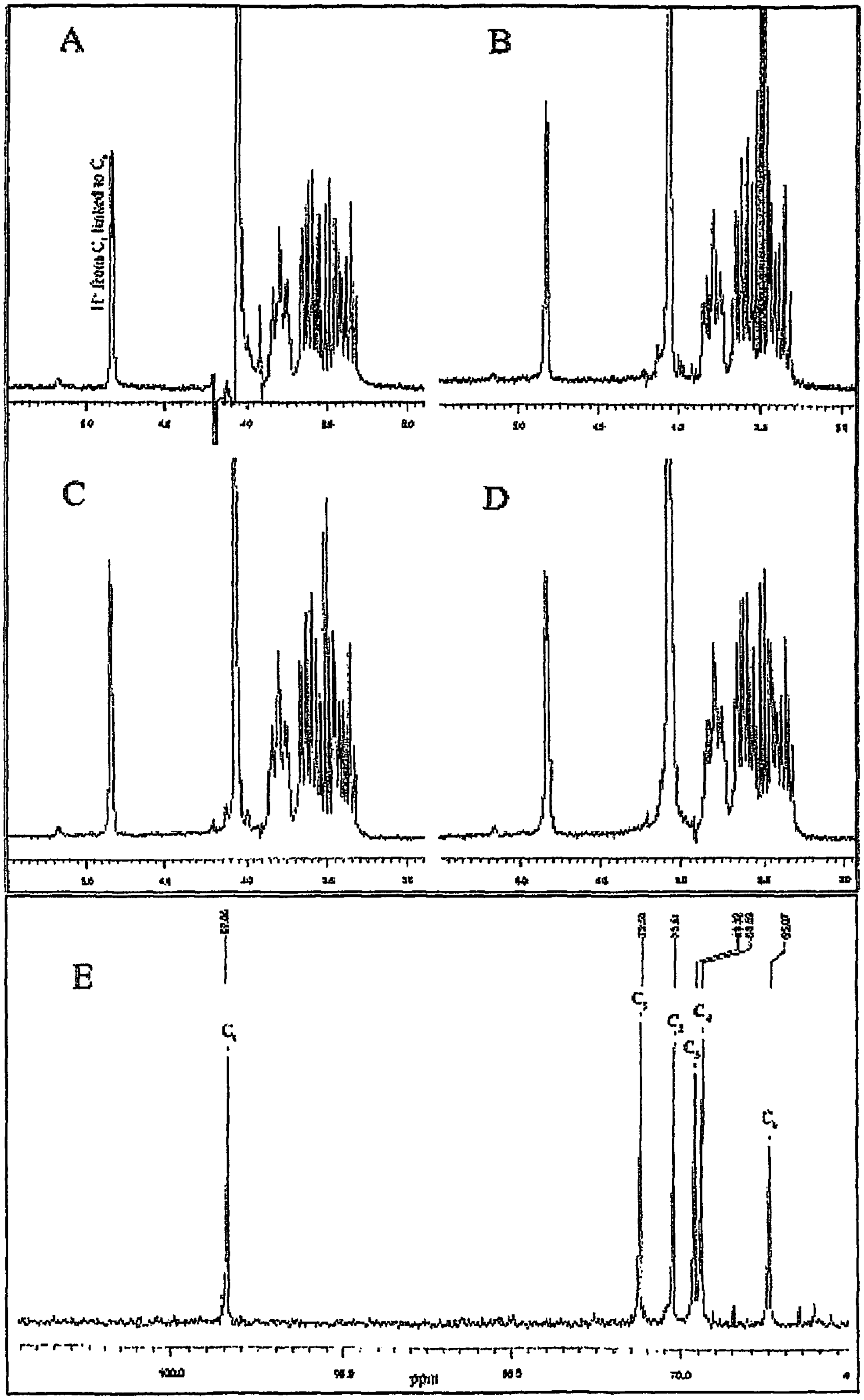
FIG. 10 A-E shows the spectra obtained by proton NMR on dextrans synthesized by A) native DSR-S from *L. mesenteroides* NRRL B-512F, B) the entire recombinant DSR-S, C) DSR-S vardel Δ4N before purification and D) DSR-S vardel Δ4N after purification. Spectrum E) is a carbon-13 spectrum of the dextran synthesized by purified DSR-S vardel Δ4N.

The NMR spectra are shown in FIGS. 10. Only α-1,6 bonds were detected. Carbon-13 NMR analysis was also carried out on the dextran synthesized by purified DSR-S vardel Δ4N. The spectrum obtained was identical to those published for the dextran from *L. mesenteroides* NRRL B-512F and entire DSR-S [3].

Figure 11:
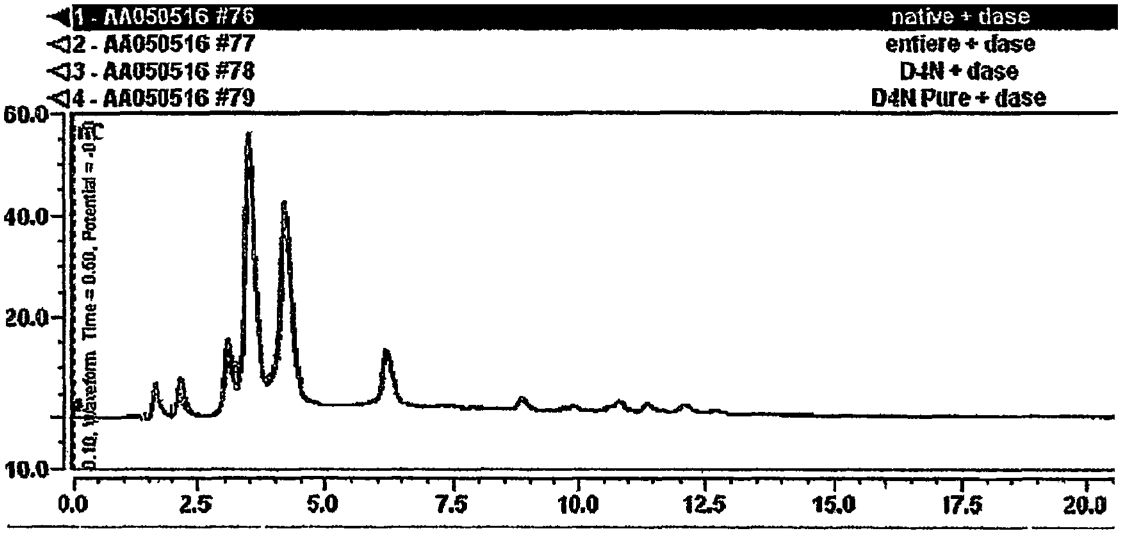
FIG. 11 corresponds to the HPAEC-PAD chromatogram of the digestion products using endodextranase (dase) of the four dextrans synthesized by native DSR-S, entire recombinant DSR-S and DSR-S vardel Δ4N, before and after purification.

These polymers were also digested with endodextranase from *Chaetomium gracile* carried out for 16 h at 37° C. with 3 enzyme units per ml of synthesis medium. The digestion products were analyzed by HPAEC-PAD (FIG. 11). The digestion profiles obtained were identical for the four analyzed dextrans, confirming that they all had at least 95% α-1,6 bonds.

The deletions made in the N and C-terminal positions of the DSR-S to construct the DSR-S vardel Δ4N variant thus have no significant influence on the initial activity of DSR-S or on the portion of glucosyl units derived from sucrose incorporated into the synthesis of the HMW dextran, the size or the structure of the polysaccharide.

Rheological Behavior of Dextrans Formed

The Theological behavior of the four dextrans was analyzed using a cone-plane system (AR 1000, TA Instruments) provided with a 4 cm diameter cone at an angle of 3.59°, and covering speeds of 0.01 to 100 $s^{-1}$. The measurements were carried out at 25° C. Dynamic experiments were carried out in the linear domain between 0 and 10 Pa, with a deformation of 8% for the dextran synthesized by native DSR-S from *L. mesenteroides* NRRL B-512F (control), 3% for that synthesized by the entire recombinant DSR-S, 5% for that synthesized by a non-purified extract of DSR-S vardel Δ4N and 0.4% for that synthesized by purified DSR-S vardel Δ4N. The complex stiffness modulus is defined by the relationship:

$$G^*(\omega) = G'(\omega) + iG''(\omega).$$

The energy conservation modulus G'(ω) is larger when the sample is predominantly elastic or highly structured. The loss modulus G"(ω) represents the energy dissipated during deformation. Predominantly viscous samples have a high G"(ω).

These rheological analyses produced entirely original results (FIG. 12). As described in the literature, native DSR-S synthesized a dextran with Newtonian behavior [25].

Figure 12A:
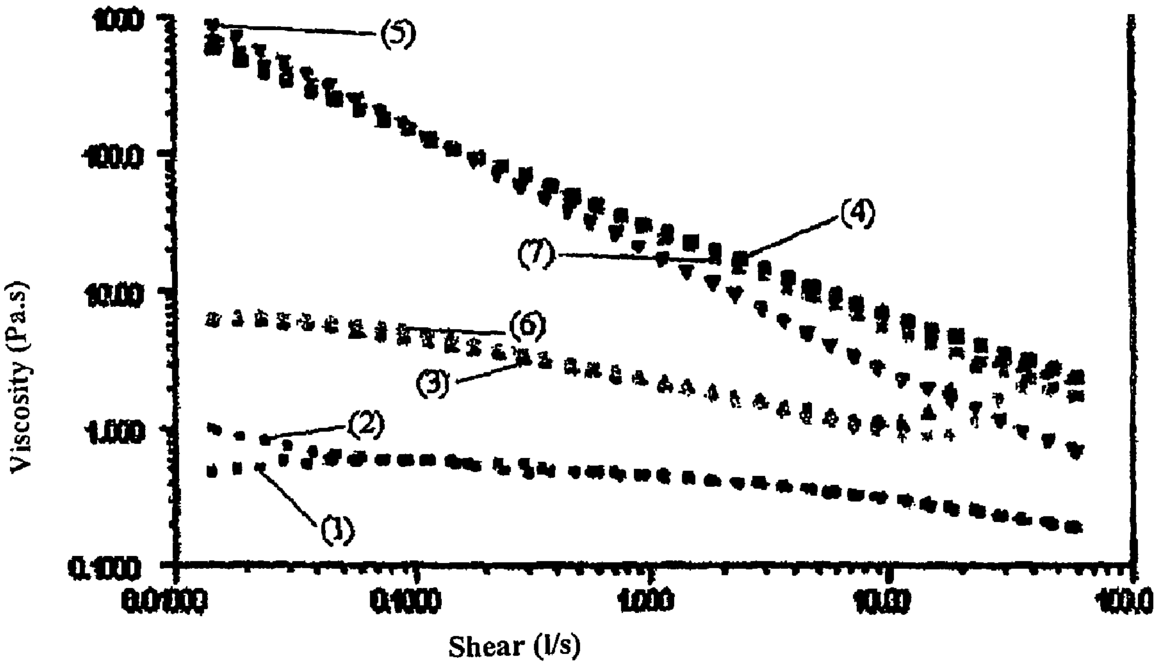
FIG. 12 shows the rheological behavior of four dextrans synthesized by native DSR-S (1) before and (2) after shearing, entire recombinant DSR-S (3) before and (4) after application of a second series of shear stresses, DSR-S vardel Δ4N (6) before and (7) after application of a second series of shear stresses, purified DSR-S vardel Δ4N (5) where A) represents the measurement of the viscosity flow, B) dynamic mode viscosity measurements (oscillations between 0 and 10 Pa), before determining the conservation G' and energy dissipation G" moduli for the dextrans synthesized by the non-purified DSR-S vardel Δ4N preparations (° and ●; solution type behavior, G'<G"; at 5% deformation) and purified preparation (□ and ■; gel type behavior G'>G"; 0.4% deformation).
Figure 12B:
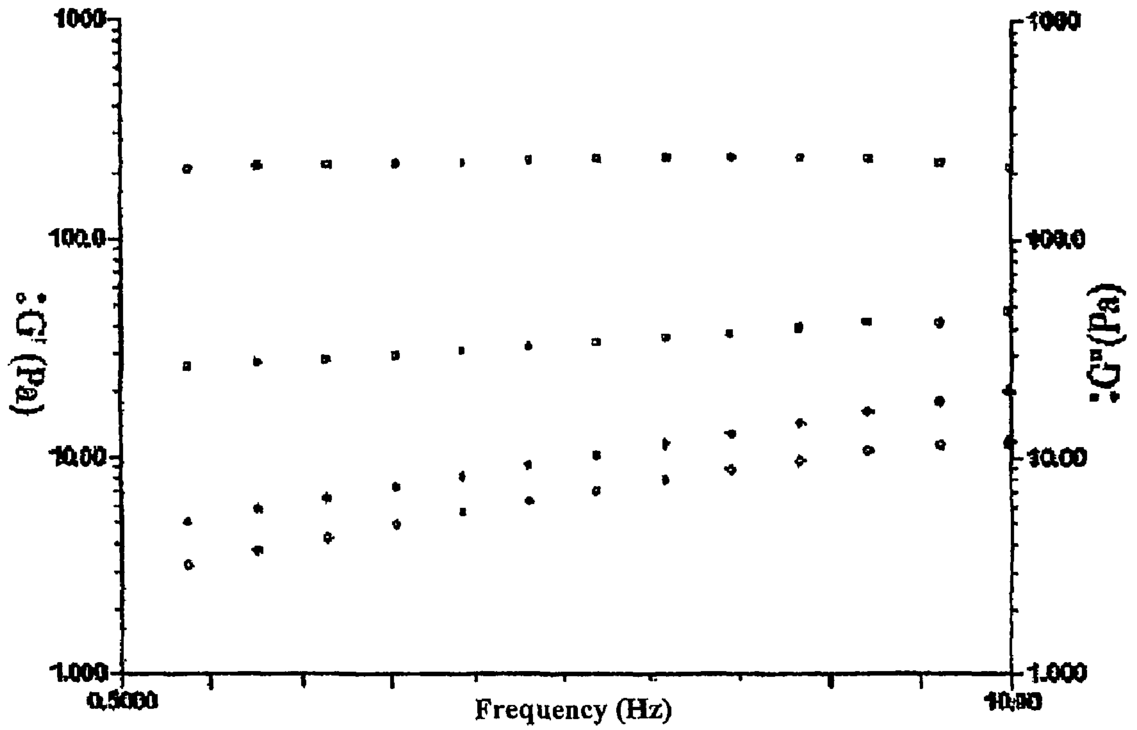

The entire recombinant DSR-S extracts and non-purified DSR-S vardel Δ4N extracts produced viscous solutions with identical behavior (viscosity about 10 times higher than that of dextran produced by native enzyme). When observed with the naked eye, they also had a fairly pronounced stringy behavior. Further, after application of new shear stresses, the behavior of said polymers changed from a solution type to a gel type, which is a novel property which has been identified for this type of biopolymer. The dextran produced by the native enzyme, in contrast, was not stringy, and its behavior was entirely reversible after application of a second series of stresses (FIG. 12A).

The purified enzyme directly synthesized a polymer having the properties of a highly structured gel (FIG. 12B, modulus G' much higher than G"), retaining its characteristics through a range of temperatures from 10° C. to 70° C. (results not shown). This behavior is completely different from that of the native enzyme.

Only the preparation of purified DSR-S vardel Δ4N contained only one active dextransucrase in the extract. Native DSR-S is known to be prone to problems of proteolytic degradation [26] and the purification techniques developed could not resolve that problem [27, 28, 29]. Entire recombinant DSR-S used in the test contained at least two active enzymatic forms, like the DSR-S vardel Δ4N preparation prior to purification. However, the degraded forms of native DSR-S, entire recombinant DSR-S and DSR-S vardel Δ4N are entirely different. It is currently assumed that cooperation between these different active enzymatic forms present in the medium could be the origin of modifications to the dextran chains, causing these differences in behavior.

EXAMPLE 6

Synthesis of Isomaltose from Sucrose

The capacity of mutant DSR-S vardel Δ4N SEV663YDA to synthesize only isomaltose (IMO with DP 2) from sucrose to the detriment of high molar mass dextrans was studied.

The mutant was purified by affinity chromatography using the procedure described for DSR-S vardel Δ4N given in Example 3.

The activity was assayed at 30° C.

With a specific activity of only 9 U/mg, the SEV663YDA mutations induced severe effects on the activity of DSR-S (loss of 98% of the initial sucrose consumption rate). That specific activity, however, is equivalent to that of recombinant amylosucrase from *N. polysaccharea [*32], which has been widely studied for its application potential.

The characterizations which were carried out demonstrate the feasibility of producing isomaltose by this mutant DSR-S, while the wild enzyme produces only high molar mass dextrans. Syntheses were carried out at 25° C. in a buffer containing a concentration of 50 mM of sodium acetate at a pH of 5.2 and 0.05 g/l of $CaCl_2$, 1 U/ml of purified enzyme and using 100 g/l of sucrose as the only substrate, or by acceptor reaction starting with 100 g/l of sucrose and 50 g/l of glucose. Exhaustion of sucrose was monitored by HPAEC-PAD analyses (see Example 4 for analysis conditions) and the reactions were interrupted after complete consumption.

Isomaltose production thus reached a yield of 47% using sucrose as the only substrate (Table 3 and FIG. 13), a yield which was equivalent to that obtained by the acceptor reaction. Adding an exogenous acceptor was thus not necessary. Traces of isomaltotriose, maltose or nigerose (not separated by the system) were also identified (FIG. 13) as well as the presence of other oligosaccharides with a DP of less than 7 and of unknown structure.

TABLE 3

Synthesis of isomaltose by mutant DSR-S vardel Δ4N SEV663YDA from 100 g/l of sucrose alone, or by acceptor reaction with 50 g/l of glucose. Concentration of different products present at the end of the reaction.

| | 100 g/l sucrose | 100 g/l sucrose + 50 g/l glucose |
|---|---|---|
| Glucose | 16.73 | 33.14 |
| Fructose | 45.95 | 42.31 |
| isomaltose | 23.99 | 47.17 |
| Other oligosaccharides | 13.33 | 27.38 |
| % of glucose residues transferred to isomaltose | 47.98% | 47.17%[2] |

[2]calculated from glucosyl residues derived from exogenous glucose and sucrose added to medium.

Thus in this Example, the production of isomaltose attained a yield of 47%. Currently, this is the first method involving a single enzyme for synthesizing isomaltose from sucrose; all prior studies being linked to the degradation of starch by a cocktail of α-amylases and glycosidases [11], or to the joint action of dextransucrase and dextranase [30]. Further, sucrose is a cheap and widely available substrate and the fructose released during the syntheses constitute a co-product the value of which can be exploited separately.

EXAMPLE 7

Synthesis of Dextran by DSR-S Vardel Δ3

Different enzymatic forms of DSR-S vardel Δ3 were produced during culture of *E. coli* TOP10. However, the entire form was vastly in the majority and the zymograms produced (see Example 3) showed that only the entire form was active.

The optimum activity temperature for this variant was 20° C. Thus, activity assays were carried out at this temperature. Production of DSR-S vardel Δ3 in accordance with Example 2 reached about 320 U/l of culture.

Dextran syntheses were carried out at 20° C. in a buffer containing 50 mM of sodium acetate, pH of 5.2, and 0.05 g/l of $CaCl_2$, 100 g/l of sucrose and 1 U/ml of non-purified DSR-S vardel Δ3 extract. The DSR-S vardel Δ3 extract could be purified by affinity chromatography on nickel resin using the protocol described for DSR-S vardel Δ4N in Example 3. However, since the sonication supernatant contained only a single enzymatic form of dextransucrase and *E. coli* did not produce another enzyme which could consume the sucrose, purification of the variant did not constitute a prerequisite for rigorous characterization of its properties. By way of comparison, dextran syntheses were carried out under the same conditions as with (non-purified) DSR-S vardel Δ4N. The disappearance of the sucrose was monitored by HPAEC-PAD analyses and the reactions were stopped (5 minutes, 95° C.) after total exhaustion.

The synthesized products were analyzed and quantified by HPAEC-PAD and HPSEC using the conditions described in Example 4. For the HPSEC analyses, the size of the dextrans was estimated using commercially available dextrans with sizes of $2\times10^6$, $503\times10^3$, 70,000, 10,000 Da, maltoheptaose and glucose (Sigma).

Figure 13:
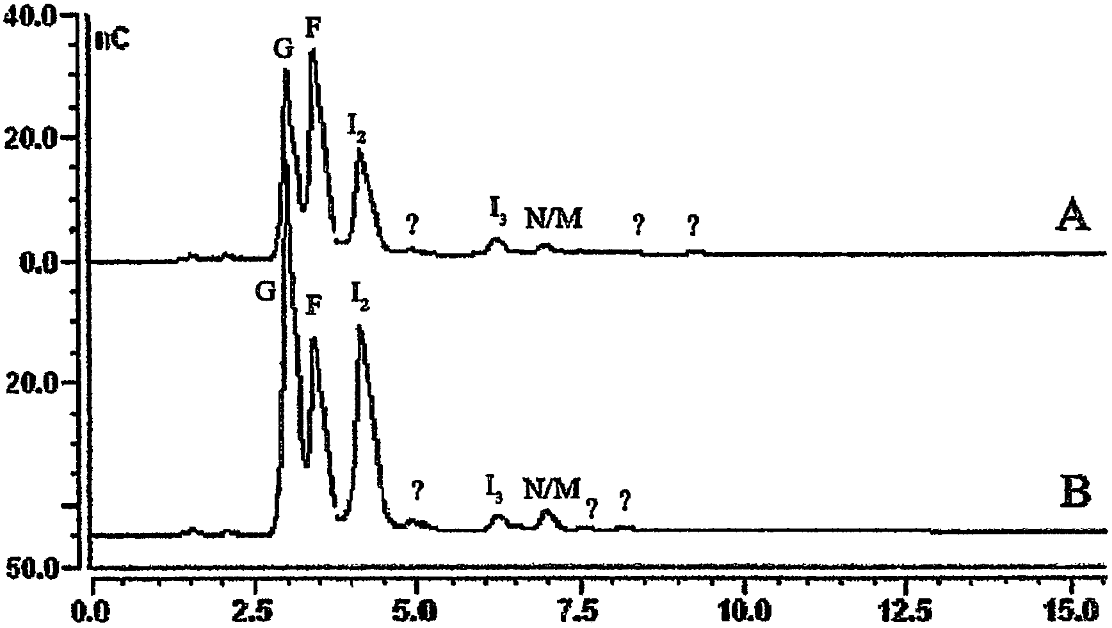
FIG. 13 shows a HPAEC-PAD chromatogram of products synthesized by mutant DSR-S vardel Δ4N SEV663YDA with 100 g/l of sucrose alone (A) or by acceptor reaction with 100 g/l of sucrose and 50 g/l of glucose (B). The symbol G signifies glucose, F: fructose, $I_2$: isomaltose, I3: isomaltotriose, N/M: nigerose or maltose (not separated by the HPAEC-pad system) and the symbol "?" corresponds to products with an unknown structure.

As can be seen in FIG. 13, at 20° C. the DSR-S vardel Δ3 variant synthesized two populations of polymers; major population of HMW dextran with a size of $2\times10^6$ Da, representing about 39% of the glucosyl residues derived from sucrose (Table 4) and a second population of 1,300 to 52,000 Da, centered at the highest peak at around 10,000 Da (about 25% glucosyl residues). This is the first time that a second population of dextran which is clearly visibly on the HPSEC chromatogram has been observed for a DSR-S variant.

Effect of Temperature on the Profile of the Products

Dextran syntheses were also carried out at a temperature of 10° C., still with a buffer containing 50 mM of sodium acetate, pH 5.2, 0.05 g/l of $CaCl_2$ and 1 U/ml of enzyme (activity assayed at 20° C.). Sucrose exhaustion was monitored by HPAEC-PAD analyses and the reactions were stopped (5 min, 95° C.) after total consumption thereof.

Figure 14:
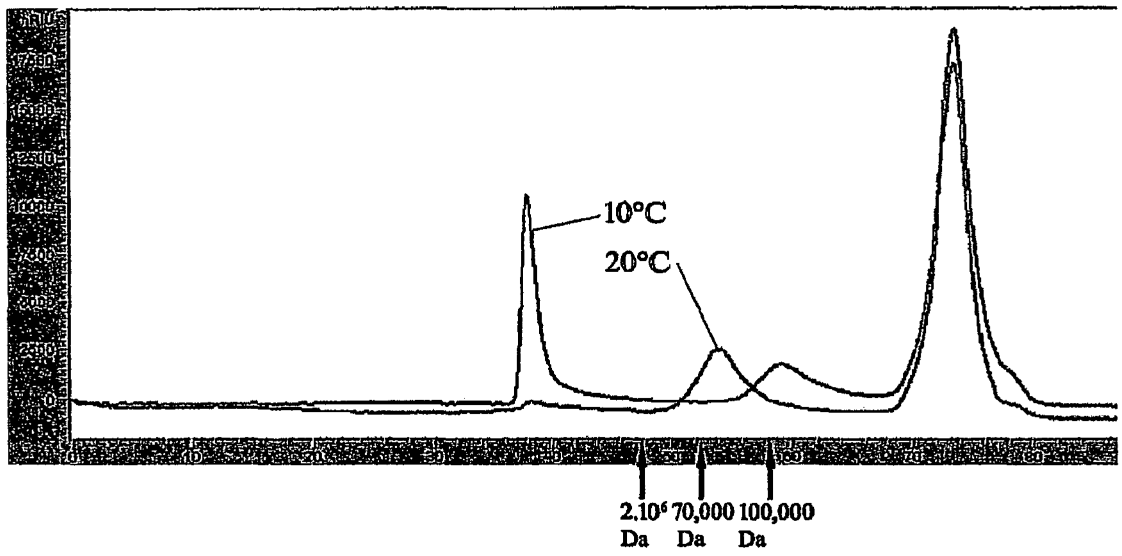
FIG. 14 shows the HPSEC chromatogram of dextrans synthesized by DSR-S vardel Δ3 at 20° C. and 10° C. The arrows correspond to the retention times of commercial dextrans of $2\times10^6$ Da, 70,000 and 10,000 Da which served as references.

As can be seen in FIG. 14, at 10° C. the DSR-S vardel Δ3 variant synthesized a population of dextran which was very different from that produced at 20° C. The major polymer (about 44%) formed at that temperature had a molar mass in the range 7,000 and $1.7\times10^5$ Da centered at the peak at around 40,000 Da.

TABLE 4

Percentage of glucosyl units incorporated into different products synthesized by DSR-S vardel Δ4N nd DSR-S vardel Δ3 at 10° C. and 20° C. starting from 100 g/l of sucrose

| | DSR-S vardel Δ4N | | DSR-S vardel Δ3 | |
|---|---|---|---|---|
| | 20° C. | 10° C. | 20° C. | 10° C. |
| HMW dextran > 2 × $10^6$ Da | 55.2 | 37.1 | 39.2 | 8.8 |
| Dextran 40,000 Da | nd[1] | nd | nd | 43.9 |
| Dextran 10,000 Da | 18.2 | 14.7 | 24.8 | nd |
| Oligosaccharides with DP ≦8[2] | 16.2 | 39.1 | 27.3 | 36.7 |
| Leucrose | 9.2 | 7.6 | 5.3 | 9.3 |
| Glucose | 1.2 | 1.5 | 3.4 | 1.3 |

[1]nd: not detected

[2]degree of polymerization calculated from retention time estimated at lower limit of 10000 Da dextran peak.

Effect of Sucrose Concentration

Four increasing concentrations of sucrose were tested (100, 150, 200 and 250 g/l) for the dextran syntheses carried out at 20° C. and 10° C. with DSR-S vardel Δ3 (1 U/ml). The total consumption of sucrose was monitored by HPAEC-PAD analyses and the syntheses were stopped after its total consumption (less than 48 h).

For the two temperatures, the initial increase in the concentration of substrate encouraged the synthesis of low molar mass dextrans. At 20° C., the synthesis of 10,000 Da dextran thus changed from a yield of 25% to 48% on changing from 100 to 250 g/l of initial sucrose. At 10° C. and from 250 g/l, HMW dextran synthesis was completely abolished, and that of dextran with the main population with a molar mass centered around 40,000 Da advantageously reached a yield of 69%.

For all of the dextrans synthesized by DSR-S vardel Δ3, at 10° C. and 20° C., and from 100 to 250 g/l of sucrose, the endodextranase digestion profiles (see Example 5) carried out confirmed that the binding specificity of DSR-S was unchanged (same oligosaccharide profiles detected by HPAEC-PAD as with DSR-S vardel Δ4N, i.e., at least 95% α-1,6 bonds).

EXAMPLE 8

Synthesis of Dextran by DSR-S Vardel Core and DSR-S Core ΔA

The DSR-S vardel Core and DSR-S Core ΔA variants were also slightly degraded during expression by *E. coli* TOP under the conditions described in Example 2. However, as was the case for the DSR-S vardel Δ3 variant, only the entire form, which was in the vast majority, was active according to the zymogram (results not shown).

The optimum activity temperature for these variants was also 20° C. Production thus reached 38 and 180 U/L of culture for DSR-S vardel Core and DSR-S Core ΔA respectively.

Dextran syntheses were carried out at 20° C. and 10° C. using 100 to 250 g/l of sucrose in a buffer containing 50 mM of sodium acetate, pH 5.2, 0.05 g/l of $CaCl_2$ and 1 U/ml of enzymatic extract (non-purified). Sucrose consumption was monitored by HPAEC-PAD analyses and the syntheses were stopped (5 min, 95° C.) after complete exhaustion (less than 48 h). The products formed were analyzed by HPAEC-PAD and HPSEC and their concentration was quantified as described in Example 5.

Figure 15:
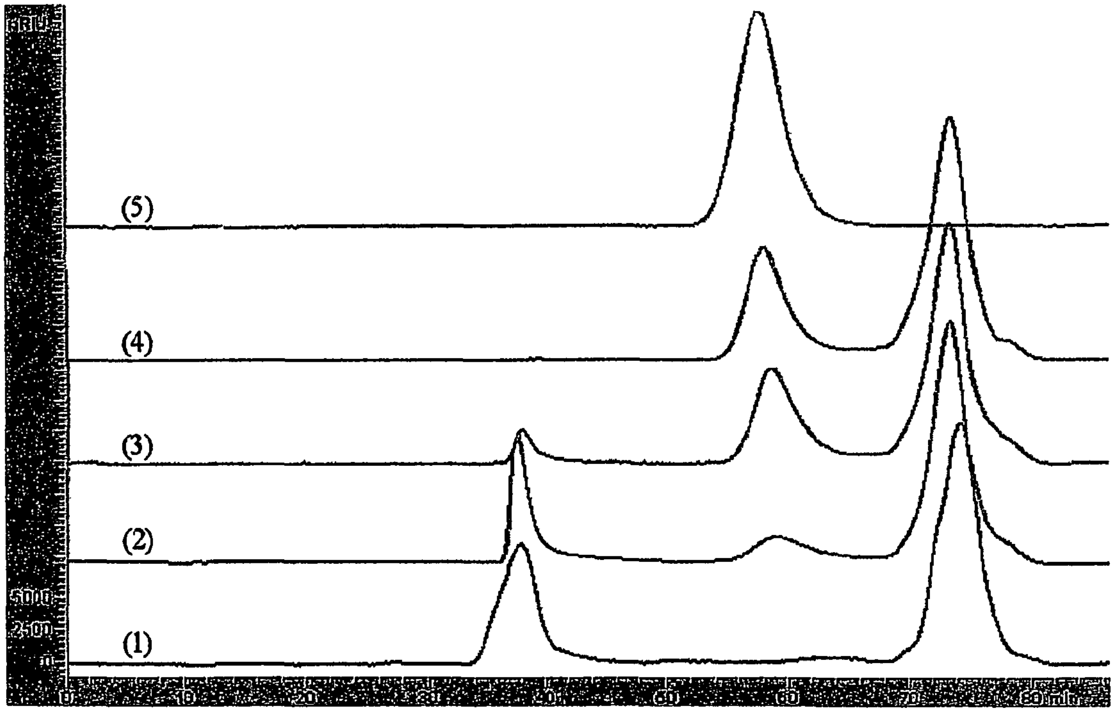
FIG. 15 shows the HPSEC chromatogram of dextrans synthesized at 20° C. with 100 g/l of sucrose and with 1 U/ml of (1) DSR-S vardel Δ4N, (2) DSR-S vardel Δ3, (3) DSR-S vardel Core and (4) DSR-S Core ΔA and the elution profile (5) of a commercial dextran of 10,000 Da (Sigma).

FIG. 15 shows the profile of the products synthesized at 20° C. by the two variants (HPSEC chromatogram). It can clearly be seen that with 5 these variants, and in contrast to DSR-S vardel Δ4N and DSR-S vardel Δ3, the major population of dextran formed had a molar mass of close to 10,000 Da with the base of the peak between 1,300 and 52,000 (at half height between 5,000 and 22,000). With the DSR-S Core ΔA variant, the synthesis of HMW dextran was completely abolished (Table 5). A reduction in temperature to 10° C. could increase the yields of dextran with ~10,000 Da without a significant size difference, as was the case with DSR-S vardel Δ3 (Table 5). Dextran synthesis with the DSR-S Core ΔA variant thus reached a yield of 75%. An equivalent yield was obtained with the DSR-S vardel Core variant when the initial concentration of sucrose was 250 g/l (results not shown).

TABLE 5

Percentage of glucosyl units incorporated into different products synthesized by DSR-S vardel Core and DSR-S Core ΔA at 10° C. and 20° C. starting from 100 g/l of sucrose

| | DSR-S vardel Δ4N | | DSR-S vardel Core | | DSR-S Core ΔA | |
|---|---|---|---|---|---|---|
| | 20° C. | 10° C. | 20° C. | 10° C. | 20° C. | 10° C. |
| HMW dextran >2 × $10^6$ Da | 55.2 | 37.1 | 9.9 | 2.4 | nd | Nd |
| Dextran 10,000 Da | 18.2 | 14.7 | 57.5 | 62.5 | 64.4 | 74.5 |
| Oligo-saccharides with DP ≦8[2] | 16.2 | 39.1 | 19.6 | 14.8 | 19.8 | 10.0 |
| Leucrose | 9.2 | 7.6 | 6.5 | 10.2 | 12.7 | 12.8 |
| Glucose | 1.2 | 1.5 | 6.5 | 10.1 | 3.1 | 2.7 |

[1]nd: not detected

[2]degree of polymerization calculated from retention time estimated at lower limit of 10000 Da dextran peak.

Figure 16:
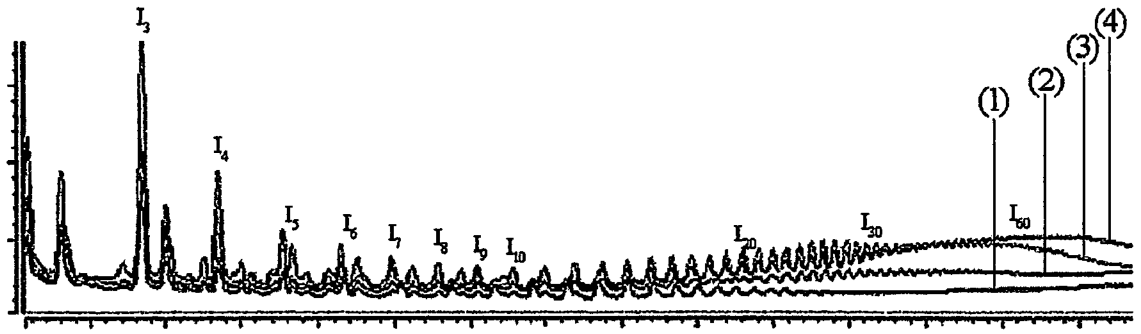
FIG. 16 shows the HPAEC-PAD profile of dextrans synthesized at 20° C. with 100 g/l of sucrose and with 1 U/ml of DSR-S vardel Δ4N (1), DSR-S vardel Δ3 (2), DSR-S vardel Core (3) and DSR-S vardel Core ΔA (4).

HPAEC-PAD analysis of the dextran synthesized from 100 g/l of sucrose at 20° C. by the different variants showed the very high polydispersibility of the product (FIG. 16), containing isomalto-oligosaccharides with a DP of 2 to a DP of about 60 for DSR-S Core ΔA in particular.

For all of the dextrans synthesized by DSR-S vardel Core and DSR-S Core ΔA at 10° C. and 20° C., and using 100 to 250 g/l of sucrose, the endodextranase digestion profiles (see Example 5) carried out confirmed that the binding specificity of DSR-S was unchanged (even the oligosaccharide profiles detected by HPAEC-PAD compared with DSR-S vardel Δ4N, thus at least 95% α-1,6 bonds).

EXAMPLE 9

Acceptor Reaction with Glucose

Acceptor reactions were carried out at 20° C. with a sucrose/glucose ratio of 2 (100 g/l of sucrose, 50 g/l of glucose), 1 U/ml of extract of DSR-S vardel Δ4N, DSR-S vardel Δ3, DSR-S vardel Core and DSR-S Core ΔA in a buffer containing 50 mM of sodium acetate at a pH of 5.2 and 0.05 g/l of $CaCl_2$. The total consumption of sucrose was monitored by HPAEC-PAD and the reactions were stopped after it had been completely exhausted. All of the variants synthesized isomalto-oligosaccharides (IMO) with a DP of 2 to about 30, to the detriment of the synthesis of polymer with a higher DP.

Figure 17A:
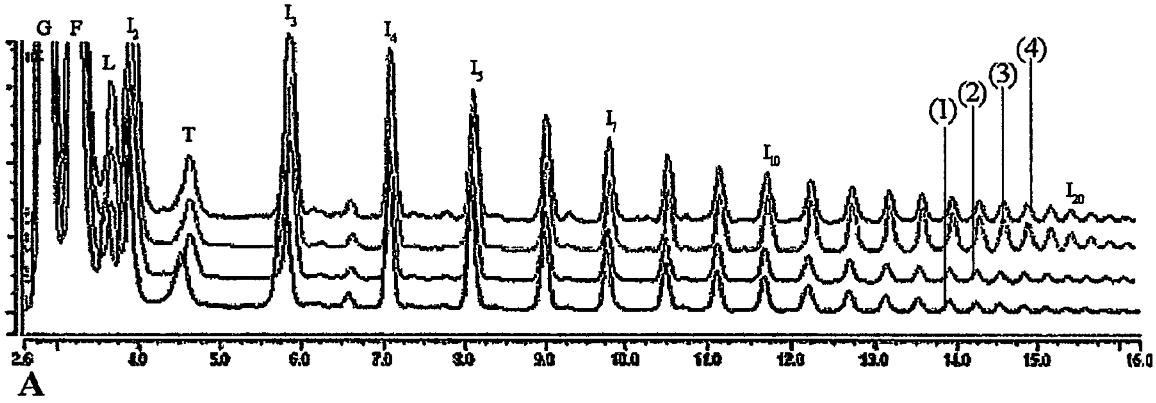
FIG. 17 shows the HPAEC-PAD profile (A) and distribution (B) of IMOs produced by an acceptor reaction at 20° C. with the variants DSR-S vardel Δ4N (1), DSR-S vardel Δ3 (2), DSR-S vardel Core (3) and DSR-S vardel Core ΔA (4). G: glucose; F: fructose; L: leucrose; T: trehalulose; I2 to I20: isomalto-oligosaccharides with DP 2 to DP 20. The insert of Figure B corresponds to an enlargement of the IMOs from DP of 15 to 27.
Figure 17B:
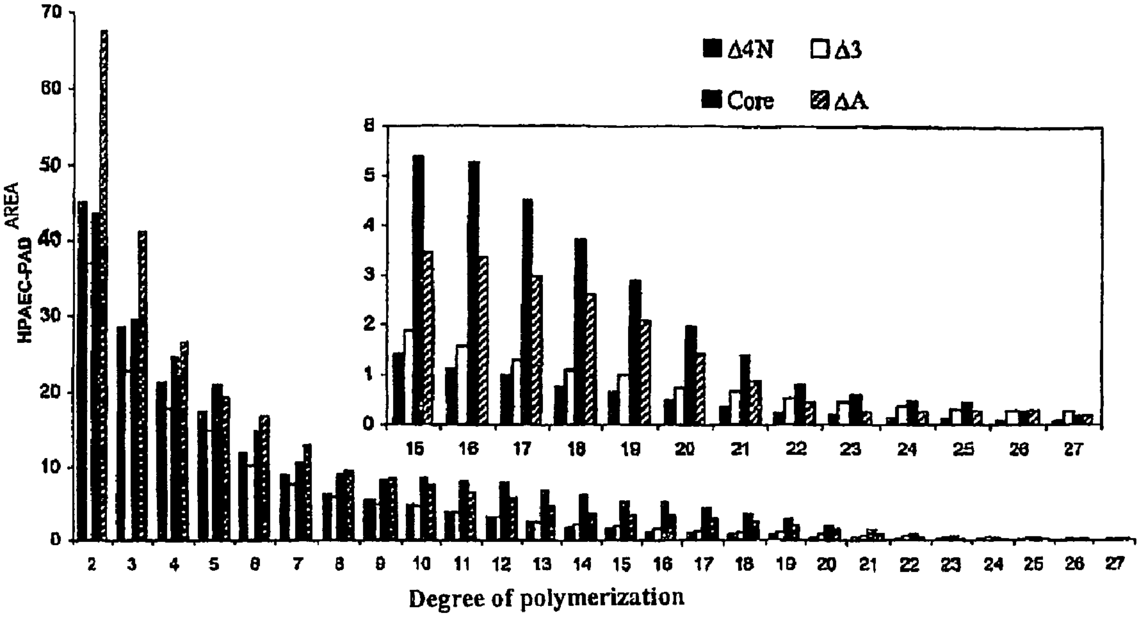

However, the yields obtained were higher for the variants truncated of A units. Hence, IMO production reached 52% in the case of DSR-S vardel Δ3 and 58% for DSR-S vardel Core and DSR-S Core ΔA, as opposed to 47% in the case of DSR-S vardel Δ4N. The oligosaccharide distribution was also modified (FIG. 17).

For DSR-S vardel Δ3, the proportion of IMO with a DP of 2 to DP of 15 was less than that of products synthesized by DSR-S vardel Δ4N. The situation was reversed for IMOs with a DP of more than 15.

Similarly, the DSR-S vardel Core and DSR-S Core ΔA mutants were shown to perform better for the synthesis of IMO with a high DP than DSR-S vardel Δ4N or native DSR-S (DP essentially 2 to 15): the production of IMO with a DP of 12 to a DP of 27 was two to five times higher with these two variants (according to the ratio of the surface areas obtained by HPAEC-PAD).

REFERENCES

[1] Monsan, P., Bozonnet, S., Albenne, C., Joucla, G., Willemot, R. M., & Remaud-Simeon, M. 2001. Homopolysaccharides from lactic acid bacteria. International Dairy Journal 11, 675-685.

[2] Coutinho, P.M. & Henrissat, B. 1999, Carbohydrate-Active Enzymes server.

[3] Monchois, V., Remaud-Simeon, M., Russell, R. R., Monsan, P., & Willemot, R. M. 1997. Characterization of *Leuconostoc mesenteroides* NRRL B-512F dextransucrase (DSR-S) and identification of amino-acid residues playing a key role in enzyme activity. Appl. Microbiol. Biotechnol. 48, 465.

[4] Koepsell, H. J., Tsuchiya, H. M., Hellman, N. N., Kazenko, A., 15 Hoffman, C. A., Sharpe, E. S., & Jackson, R. W. 1953. Enzymatic synthesis of dextran; acceptor specificity and chain initiation. J Biol Chem 200, 793-801.

[5] Groenwall, A. J., & Ingelman, G. A. 1948. Manufacture of infusion and injection fluids. U.S. Pat. No. 2,437,518.

[6] Robyt, J. F. 1985. Dextran, p. 753-767. In J. I. Kroschwitz (ed.), Encyclopedia of polymer Science, vol. 4. Wiley-VCH, New-York.

[7] Ahsan, N. 1998. Intravenous infusion of total dose iron is superior to oral iron in treatment of anemia in peritoneal dialysis patients: a single center comparative study. J Am Soc Nephrol 9, 664-8.

[8] De Belder, A. N. 1996 Medical applications of dextran and its derivatives p 275-296. In S. Domitriu (ed.), Polysaccharides in medicinal applications. Marcel Dekker, Inc., New York.

[9] Jagodzinski, P. P., Lewandowska, M., Januchowski, R., Franciszkiewicz, K., & Trzeciak, W. H. 2002. The effect of high molecular weight dextran sulfate on the production of interleukin-8 in monocyte cell culture. Biomed Pharmacother 56, 254-7.

[10] Hersline, R. 2004. Antiviral composition. U.S. Pat. No. 6,821,958.

[11] Nakakuki, T. 2002. Present status and future of functional oligosaccharide development in Japan. Pure App Chem 74, 1245-1251.

[12] Goulas, A. K., Fisher, D. A., Grimble, G. K. Grandison, A. S., & Rastall, R. A. 2004b. Synthesis of isomaltooligosaccharides and oligodextrans by the combined use of dextransucrase and dextranase. Enzyme and Microbial Technology 35, 327-338.

[13] Rousseau, V., Lepargneur, J., Roques, C., Remaud-Simeon, M., & Paul, F. 2005. Prebiotic effect of oligosaccharides on selected vaginal lactobacilli and pathogenic microorganisms. Anaerobe, 11(3),145-153.

[14] Goulas, A. K., Cooper, J. M., Grandison, A. S., & Rastall, R. A. 2004a. Synthesis of isomaltooligosaccharides and oligodextrans in a recycle membrane bioreactor by the combined use of dextransucrase and dextranase. Biotechnol Bioeng 88, 778-87.

[15] Scientific Committee On Food. 2000. Opinion on the scientific committee on food on a dextran preparation produced using *Leuconostoc mesenteroides, Saccharomyces cerevisiae* and *Lactobacillus* ssp as a novel food ingredient in bakery products. European Commission, Health & Consumer Protection Directorate-General, Brussels.

[16] Monchois, V., Reverte, A., Remaud-Simeon, M., Monsan, P., & Willemot, R. M. 1998. Effect of *Leuconostoc mesenteroides* NRRL B-512F dextransucrase carboxy-terminal deletions on dextran and oligosaccharide synthesis. Appl. Environ. Microbiol. 64, 1644-49.

[17] R. Kaufman, Methods in Enzymology 185, 537-566 (1990)

[18] Tannock, W. G. Probiotics and Prebiotics. Where are we going? Caister Academic Press, Wymondham, UK 2002

[19] Khalikova, E., Susi, P. & Korpela, T., 2005. Microbial dextran-hydrolyzing enzymes: fundamentals and applications. Microbial. Mol. Biol. 69, 306-25

[20] Merrifield, R. B., 1963 J. Am. Chem. Soc. 85,2149.

[21] Monsan, P., Paul, F., 1995 Enzymatic synthesis of oligosaccharides FEMS Microbiol. Rev, 16, 187-192.

[22] Sumner, J., & Howell, S. 1935. A method for determination of invertase activity. Journal of Biological Chemistry 108, 51.

[23] Gibson, G. R., Roberfroid, M. B., 1995 Dietary modulation of the human colonic microbiota: introducing the concept of prebiotics J. Nutr., 125, 1401-12.

[24] Paul, F., Auriol, D., Oriol, E., & Monsan, P. 1984. Production and purification of dextransucrase from *Leuconostoc mesenteroides* NRRL B-512F. Ann. N.Y. Acad. Sci. 434, 267-270.

[25] Carrasco, F., Chomet, E., Overend, R. P., & Costa, J. 1989 A generalized correlation for the viscosity of dextrans in aqueous solutions as a function of temperature, concentration, and molecular weight at low shear rate. J Appl Polymer Sci 37, 2087-98.

[26] Arguello-Morales, M., Sanchez-Gonzalez. M., Canedo, M., Quirasco. M., Farres, A., & Lopez-Munguia, A. 2005. Proteolytic modification of *Leuconostoc mesenteroides* B-512F dextransucrase. Antonie Van Leeuwenhoek 87, 131-41.

[27] Miller, A. W., Eklund, S. H., & Robyt, J. F. 1986. Milligram to gram scale purification and characterization of dextransucrase from *Leuconostoc mesenteroides* NRRL B-512F. Carbohydr. Res. 147, 119.

[28] Kobayashi, M., & Matsumada, K. 1986. Electrophoretic analysis of the multiple forms of dextransucrase from *Leuconostoc mesenteroides*. J. Biochem. (Tokyo) 100, 615

[29] Kobayashi, M., Mihara, K., & Matsuda, K. 1986. Dextransucrase from *Leuconostoc mesenteroides* NRRL B-512F: characterization of the enzyme bound to Sephadex gel. Agric Biol Chem 50, 551-556.

[30] Paul, F., Monsan, P., Remaud, M., Pelenc, V. Process for preparing enzymatically a sugar mixture having a high content of isomaltose from sucrose, U.S. Pat. No. 4,861, 381

[31] Blood Products Committee 83rd Meeting—Jul. 21, 2005

[32] Potocki-de-Montalk, G., Remaud-Simeon, M., Willemot, R. M., Planchot, V., and Monsan, P. 1999. Sequence analysis of the gene encoding amylosucrase from *Neisseria polysaccharea* and characterization of the recombinant enzyme. J. Bacteriol. 181, 375-381.

[33] Barik, S. 1995. site-directed mutagenesis by double polymerase chain reaction. Mol Biotechno/3, 1-7.

The invention claimed is:

1. An isolated truncated dextransucrase consisting essentially of SEQ ID NO: 9 or SEQ ID NO: 25 provided that it conserves its dextransucrase enzymatic activity.

2. An isolated truncated dextransucrase consisting of SEQ ID NO: 9 or SEQ ID NO: 25 provided that it conserves its dextransucrase enzymatic activity.

3. An isolated truncated dextransucrase consisting essentially of SEQ ID NO: 9 or SEQ ID NO: 25 provided that it conserves its specificity for synthesizing $\alpha$-1,6 bonds.

4. An isolated truncated and mutated dextransucrase consisting of SEQ ID NO: 9 or SEQ ID NO: 25 provided that it conserves specificity for synthesizing $\alpha$-1,6 bonds.

5. A fusion protein consisting essentially of SEQ ID NO: 9 or SEQ ID NO: 25 and a protein tag at the N-terminal or C-terminal position of said fusion protein.

6. A fusion protein consisting of SEQ ID NO: 9 or SEQ ID NO: 25 and a protein tag at the N-terminal or C-terminal position of said fusion protein.

7. The fusion protein according to claim 5, in which the protein tag is a thioredoxin located at the N-terminal end.

8. The fusion protein according to claim 6, in which the protein tag is a thioredoxin located at the N-terminal end.

9. The fusion protein according to claim 5, in which the protein tag is a 6xHis tag located at the C-terminal end.

10. The fusion protein according to claim 6, in which the protein tag is a 6xHis tag located at the C-terminal end.

* * * * *

SEQUENCE LISTING

<160> NUMBER OF SEQ ID NOS: 26

<210> SEQ ID NO 1
<211> LENGTH: 4356
<212> TYPE: DNA
<213> ORGANISM: Artificial
<220> FEATURE:
<223> OTHER INFORMATION: Truncated dextrane saccharase

<400> SEQUENCE: 1
atgggatctg ataaaattat tcatctgact gatgattctt ttgatactga tgtacttaag 60
gcagatggtg caatcctggt tgatttctgg gcacactggt gcggtccgtg caaaatgatc 120
gctccgattc tggatgaaat cgctgacgaa tatcagggca aactgaccgt tgcaaaactg 180
aacatcgatc acaacccggg cactgcgccg aaatatggca tccgtggtat cccgactctg 240
ctgctgttca aaaacggtga agtggcggca accaaagtgg gtgcactgtc taaaggtcag 300
ttgaaagagt tcctcgacgc taacctggcc ggctctggat ccggtgatga cgatgacaag 360
ctcgccctta tgacacaaca agttagcggc aagtacgttg aaaaagacgg tagttggtat 420
tattattttg atgatggcaa aaatgctaaa ggtttatcaa cgatagacaa caatattcaa 480
tatttttacg agagtggtaa acaagccaaa ggacagtatg tcacaattga taatcaaaca 540
tattattttg ataagggctc aggtgatgag ttaactggtc tgcaaagcat tgatgggaac 600
atagttgctt ttaacgatga agggcaacaa atttttaatc aatattacca atctgaaaat 660
ggtacaacat actactttga tgataaagga cacgctgcta ccggtattaa gaatatcgag 720
ggcaaaaatt attattttga taatcttggg caactaaaaa aaggcttctc tggtgtgatt 780
gatggtcaaa taatgacatt tgatcaggaa acagggcaag aagtttctaa cacaacttct 840
gaaataaaag aaggtttgac gactcaaaac acggattata gcgaacataa tgcagcccac 900
ggtacggatg ctgaggactt tgaaaatatt gacggctatt taacagctag ttcatggtat 960
cgtccaacag gtattttacg taacggaaca gactgggaac cttctacaga tacagatttc 1020
agaccaatat tgtcagtgtg gtggccagat aagaacaccc aggtcaatta tttaaattac 1080
atggctgatt tagggtttat cagtaatgcg gacagttttg aaactgggga tagccaaagc 1140
ttattaaatg aagcaagtaa ctatgttcaa aaatcaattg aaatgaaaat tagtgcgcaa 1200
caaagtacag agtggttaaa ggatgcaatg gcggccttca ttgtcgcgca accacagtgg 1260
aatgaaacta gtgaagatat gagcaatgac catttacaaa atggcgcatt aacttatgtc 1320

-continued

```
aacagtccac tgacacctga cgctaattca aactttagac tacttaatcg gacaccaaca   1380
aaccagactg gtgaacaagc gtataattta gataattcaa aaggtggttt tgaattgttg   1440
ttagccaatg acgttgataa ttcaaaccct gtagtacaag cagaacaatt gaattggtta   1500
tattatttaa tgaattttgg tacgattacg gccaacgacg cggatgctaa ttttgatggt   1560
attcgtgtag atgcagtcga caatgtggat gctgatttgt tacaaattgc tgccgattat   1620
ttcaaactag cttacggtgt tgatcaaaat gatgctactg ctaatcagca tctttcaatt   1680
ttggaagatt ggagtcacaa tgatcctttg tatgtaacag atcaaggaag caatcaatta   1740
accatggatg attatgtgca cacacaatta atctggtctc taacaaaatc atctgacata   1800
cgaggtacaa tgcagcgctt cgtggattat tatatggtgg atcgatctaa tgatagtaca   1860
gaaaacgaag ccattcctaa ttacagcttt gtacgtgcac acgacagcga agtgcaaacg   1920
gttattgccc aaattgtttc cgatttgtat cctgatgttg aaaatagttt agcaccaaca   1980
acagaacaat tggcagctgc tttcaaagta tacaatgaag atgaaaaatt agcagacaaa   2040
aagtacacac aatataatat ggctagtgct tatgcgatgt tgctaaccaa taaggatact   2100
gttcctcgtg tctattatgg cgatttatat acagatgatg gtcaatatat ggcaacaaag   2160
tcaccatact atgatgcgat taacactttg ctaaaggcta gagttcagta tgttgctggt   2220
ggccaatcga tgtccgttga tagtaatgac gtgttaacaa gtgttcgcta tggtaaagat   2280
gccatgacag cttctgacac tggaacatct gagacgcgta ctgaaggtat tggagtcatc   2340
gtcagcaata acgcggagct acaattagag gatgggcata ctgtcacatt gcatatgggg   2400
gcagctcata agaaccaagc ttatcgtgct ttgttatcaa caactgcaga tggattagct   2460
tattatgata ctgatgaaaa tgcacctgtg gcgtacacag atgctaacgg cgatttgatt   2520
tttacgaatg aatcaattta tggtgtacaa aatccacaag tttctggtta cttggcagtt   2580
tgggttccgg taggtgcgca acaagatcaa gatgcacgaa cggcctctga tacaacaaca   2640
aacacgagtg ataaagtgtt ccattcaaac gctgctcttg attctcaagt catctacgaa   2700
ggtttctcaa acttccaagc atttgctaca gacagcagtg aatatacaaa cgtagtcatc   2760
gctcagaatg cggaccaatt taagcaatgg ggtgtgacaa gcttccaatt ggcaccacaa   2820
tatcgttcaa gtacagatac aagtttcttg gattcaatta ttcaaaacgg gtatgcattc   2880
acggatcgtt atgacttagg ttatggcaca ccgacaaaat atggaactgc tgatcagttg   2940
cgcgatgcta ttaaagcctt acatgctagc ggtattcaag ccattgccga ttgggtgccg   3000
gaccaaattt ataatttgcc agagcaagaa ttagctactg tcacaagaac aaattcattt   3060
ggagatgacg atacagattc tgatattgac aatgccttat atgttgtaca aagtcgtggg   3120
ggtggtcaat atcaagagat gtatggtggt gccttcttag aagagttaca ggcactctat   3180
ccatccctat ttaaagtgaa tcaaatctca actggcgttc caattgatgg cagtgtaaag   3240
attactgagt gggcggctaa gtacttcaat ggctctaaca tccaaggtaa aggtgctgga   3300
tacgtattga aagatatggg ttctaataag tactttaagg tcgtttcgaa cactgaggat   3360
ggtgactact taccaaaaca gttaactaat gatctgtcag aaactggctt tacacacgat   3420
gataaaggaa tcatctatta tacattaagt ggttatcgtg cccaaaatgc atttattcaa   3480
gatgatgata ataactatta ctattttgat aaaacaggtc atttagtaac aggtttgcaa   3540
aagattaata accataccta cttcttctta cctaatggta tcgaactggt caagagcttc   3600
ttacaaaacg aagatggtac aattgtttat ttcgataaga aaggtcatca agtttttgat   3660
caatatataa ctgatcaaaa tggaaatgcg tattactttg atgatgctgg tgtaatgctt   3720
```

-continued aaatcagggc ttgcaacgat tgatggacat caacagtatt ttgatcaaaa tggtgtgcag 3780
gttaaggata agtttgtgat tggcactgat ggttataagt attactttga accaggtagt 3840
ggtaacttag ctatcctacg ttatgtgcaa aatagtaaga atcaatggtt ctattttgat 3900
ggtaatggcc atgctgtcac tggtttccaa acaattaatg gtaaaaaaca atatttctat 3960
aatgatggtc atcaaagtaa aggtgaattc attgatgcag acggggatac tttctatacg 4020
agtgccactg atggtcgcct agtaactggt gttcagaaga ttaatggtat tacctatgct 4080
tttgataaca caggaaattt gatcacaaat cagtattatc aattagcaga tggtaaatat 4140
atgttgttag atgatagtgg tcgtgcgaaa acagggtttg tattgcaaga tggtgtacta 4200
agatacttcg atcaaaacgg tgagcaagtg aaagatgcta tcattgtgga tccagatact 4260
aacttgagtt acaagggcga gcttgaaggt aagcctatcc ctaaccctct cctcggtctc 4320
gattctacgc gtaccggtca tcatcaccat caccat 4356

<210> SEQ ID NO 2
<211> LENGTH: 4092
<212> TYPE: DNA
<213> ORGANISM: Artificial
<220> FEATURE:
<223> OTHER INFORMATION: Truncated dextrane saccharase

<400> SEQUENCE: 2
atgggatctg ataaaattat tcatctgact gatgattctt ttgatactga tgtacttaag 60
gcagatggtg caatcctggt tgatttctgg gcacactggt gcggtccgtg caaaatgatc 120
gctccgattc tggatgaaat cgctgacgaa tatcagggca aactgaccgt tgcaaaactg 180
aacatcgatc acaacccggg cactgcgccg aaatatggca tccgtggtat cccgactctg 240
ctgctgttca aaaacggtga agtggcggca accaaagtgg gtgcactgtc taaaggtcag 300
ttgaaagagt tcctcgacgc taacctggcc ggctctggat ccggtgatga cgatgacaag 360
ctcgccctta tgacacaaca agttagcggc aagtacgttg aaaaagacgg tagttggtat 420
tattattttg atgatggcaa aaatgctaaa ggtttatcaa cgatagacaa caatattcaa 480
tatttttacg agagtggtaa acaagccaaa ggacagtatg tcacaattga taatcaaaca 540
tattattttg ataagggctc aggtgatgag ttaactggtc tgcaaagcat tgatgggaac 600
atagttgctt ttaacgatga agggcaacaa atttttaatc aatattacca atctgaaaat 660
ggtacaacat actactttga tgataaagga cacgctgcta ccggtattaa gaatatcgag 720
ggcaaaaatt attattttga taatcttggg caactaaaaa aaggcttctc tggtgtgatt 780
gatggtcaaa taatgacatt tgatcaggaa acagggcaag aagtttctaa cacaacttct 840
gaaataaaag aaggtttgac gactcaaaac acggattata gcgaacataa tgcagcccac 900
ggtacggatg ctgaggactt tgaaaatatt gacggctatt taacagctag ttcatggtat 960
cgtccaacag gtattttacg taacggaaca gactgggaac cttctacaga tacagatttc 1020
agaccaatat tgtcagtgtg gtggccagat aagaacaccc aggtcaatta tttaaattac 1080
atggctgatt tagggtttat cagtaatgcg gacagttttg aaactgggga tagccaaagc 1140
ttattaaatg aagcaagtaa ctatgttcaa aaatcaattg aaatgaaaat tagtgcgcaa 1200
caaagtacag agtggttaaa ggatgcaatg gcggccttca ttgtcgcgca accacagtgg 1260
aatgaaacta gtgaagatat gagcaatgac catttacaaa atggcgcatt aacttatgtc 1320
aacagtccac tgacacctga cgctaattca aactttagac tacttaatcg gacaccaaca 1380

-continued

```
aaccagactg gtgaacaagc gtataattta gataattcaa aaggtggttt tgaattgttg   1440
ttagccaatg acgttgataa ttcaaaccct gtagtacaag cagaacaatt gaattggtta   1500
tattatttaa tgaattttgg tacgattacg gccaacgacg cggatgctaa ttttgatggt   1560
attcgtgtag atgcagtcga caatgtggat gctgatttgt tacaaattgc tgccgattat   1620
ttcaaactag cttacggtgt tgatcaaaat gatgctactg ctaatcagca tctttcaatt   1680
ttggaagatt ggagtcacaa tgatcctttg tatgtaacag atcaaggaag caatcaatta   1740
accatggatg attatgtgca cacacaatta atctggtctc taacaaaatc atctgacata   1800
cgaggtacaa tgcagcgctt cgtggattat tatatggtgg atcgatctaa tgatagtaca   1860
gaaaacgaag ccattcctaa ttacagcttt gtacgtgcac acgacagcga agtgcaaacg   1920
gttattgccc aaattgtttc cgatttgtat cctgatgttg aaaatagttt agcaccaaca   1980
acagaacaat tggcagctgc tttcaaagta tacaatgaag atgaaaaatt agcagacaaa   2040
aagtacacac aatataatat ggctagtgct tatgcgatgt tgctaaccaa taaggatact   2100
gttcctcgtg tctattatgg cgatttatat acagatgatg gtcaatatat ggcaacaaag   2160
tcaccatact atgatgcgat taacactttg ctaaaggcta gagttcagta tgttgctggt   2220
ggccaatcga tgtccgttga tagtaatgac gtgttaacaa gtgttcgcta tggtaaagat   2280
gccatgacag cttctgacac tggaacatct gagacgcgta ctgaaggtat tggagtcatc   2340
gtcagcaata acgcggagct acaattagag gatgggcata ctgtcacatt gcatatgggg   2400
gcagctcata agaaccaagc ttatcgtgct ttgttatcaa caactgcaga tggattagct   2460
tattatgata ctgatgaaaa tgcacctgtg gcgtacacag atgctaacgg cgatttgatt   2520
tttacgaatg aatcaattta tggtgtacaa aatccacaag tttctggtta cttggcagtt   2580
tgggttccgg taggtgcgca acaagatcaa gatgcacgaa cggcctctga tacaacaaca   2640
aacacgagtg ataaagtgtt ccattcaaac gctgctcttg attctcaagt catctacgaa   2700
ggtttctcaa acttccaagc atttgctaca gacagcagtg aatatacaaa cgtagtcatc   2760
gctcagaatg cggaccaatt taagcaatgg ggtgtgacaa gcttccaatt ggcaccacaa   2820
tatcgttcaa gtacagatac aagtttcttg gattcaatta ttcaaaacgg gtatgcattc   2880
acggatcgtt atgacttagg ttatggcaca ccgacaaaat atggaactgc tgatcagttg   2940
cgcgatgcta ttaaagcctt acatgctagc ggtattcaag ccattgccga ttgggtgccg   3000
gaccaaattt ataatttgcc agagcaagaa ttagctactg tcacaagaac aaattcattt   3060
ggagatgacg atacagattc tgatattgac aatgccttat atgttgtaca aagtcgtggg   3120
ggtggtcaat atcaagagat gtatggtggt gccttcttag aagagttaca ggcactctat   3180
ccatccctat ttaaagtgaa tcaaatctca actggcgttc caattgatgg cagtgtaaag   3240
attactgagt gggcggctaa gtacttcaat ggctctaaca tccaaggtaa aggtgctgga   3300
tacgtattga aagatatggg ttctaataag tactttaagg tcgtttcgaa cactgaggat   3360
ggtgactact taccaaaaca gttaactaat gatctgtcag aaactggctt tacacacgat   3420
gataaaggaa tcatctatta tacattaagt ggttatcgtg cccaaaatgc atttattcaa   3480
gatgatgata ataactatta ctattttgat aaaacaggtc atttagtaac aggtttgcaa   3540
aagattaata accataccta cttcttctta cctaatggta tcgaactggt caagagcttc   3600
ttacaaaacg aagatggtac aattgtttat ttcgataaga aaggtcatca agtttttgat   3660
caatatataa ctgatcaaaa tggaaatgcg tattactttg atgatgctgg tgtaatgctt   3720
aaatcagggc ttgcaacgat tgatggacat caacagtatt ttgatcaaaa tggtgtgcag   3780
```

-continued gttaaggata agtttgtgat tggcactgat ggttataagt attactttga accaggtagt 3840
ggtaacttag ctatcctacg ttatgtgcaa aatagtaaga atcaatggtt ctattttgat 3900
ggtaatggcc atgctgtcac tggtttccaa acaattaatg gtaaaaaaca atatttctat 3960
aatgatggtc atcaaagtaa aggtgaattc attgatgcag acgggtacaa gggcgagctt 4020
gaaggtaagc ctatccctaa ccctctcctc ggtctcgatt ctacgcgtac cggtcatcat 4080
caccatcacc at 4092

<210> SEQ ID NO 3
<211> LENGTH: 3495
<212> TYPE: DNA
<213> ORGANISM: Artificial
<220> FEATURE:
<223> OTHER INFORMATION: Truncated dextrane saccharase

<400> SEQUENCE: 3
atgggatctg ataaaattat tcatctgact gatgattctt ttgatactga tgtacttaag 60
gcagatggtg caatcctggt tgatttctgg gcacactggt gcggtccgtg caaaatgatc 120
gctccgattc tggatgaaat cgctgacgaa tatcagggca aactgaccgt tgcaaaactg 180
aacatcgatc acaacccggg cactgcgccg aaatatggca tccgtggtat cccgactctg 240
ctgctgttca aaaacggtga agtggcggca accaaagtgg gtgcactgtc taaaggtcag 300
ttgaaagagt tcctcgacgc taacctggcc ggctctggat ccggtgatga cgatgacaag 360
ctcgccctta tgacacaaca agttagcggc aagtacgttg aaaaagacgg tagttggtat 420
tattattttg atgatggcaa aaatgctaaa ggtttatcaa cgatagacaa caatattcaa 480
tatttttacg agagtggtaa acaagccaaa ggacagtatg tcacaattga taatcaaaca 540
tattattttg ataagggctc aggtgatgag ttaactggtc tgcaaagcat tgatgggaac 600
atagttgctt ttaacgatga agggcaacaa atttttaatc aatattacca atctgaaaat 660
ggtacaacat actactttga tgataaagga cacgctgcta ccggtattaa gaatatcgag 720
ggcaaaaatt attattttga taatcttggg caactaaaaa aaggcttctc tggtgtgatt 780
gatggtcaaa taatgacatt tgatcaggaa acagggcaag aagtttctaa cacaacttct 840
gaaataaaag aaggtttgac gactcaaaac acggattata gcgaacataa tgcagcccac 900
ggtacggatg ctgaggactt tgaaaatatt gacggctatt taacagctag ttcatggtat 960
cgtccaacag gtattttacg taacggaaca gactgggaac cttctacaga tacagatttc 1020
agaccaatat tgtcagtgtg gtggccagat aagaacaccc aggtcaatta tttaaattac 1080
atggctgatt tagggtttat cagtaatgcg gacagttttg aaactgggga tagccaaagc 1140
ttattaaatg aagcaagtaa ctatgttcaa aaatcaattg aaatgaaaat tagtgcgcaa 1200
caaagtacag agtggttaaa ggatgcaatg gcggccttca ttgtcgcgca accacagtgg 1260
aatgaaacta gtgaagatat gagcaatgac catttacaaa atggcgcatt aacttatgtc 1320
aacagtccac tgacacctga cgctaattca aactttagac tacttaatcg gacaccaaca 1380
aaccagactg gtgaacaagc gtataattta gataattcaa aaggtggttt tgaattgttg 1440
ttagccaatg acgttgataa ttcaaaccct gtagtacaag cagaacaatt gaattggtta 1500
tattatttaa tgaattttgg tacgattacg gccaacgacg cggatgctaa ttttgatggt 1560
attcgtgtag atgcagtcga caatgtggat gctgatttgt tacaaattgc tgccgattat 1620
ttcaaactag cttacggtgt tgatcaaaat gatgctactg ctaatcagca tctttcaatt 1680

-continued ttggaagatt ggagtcacaa tgatcctttg tatgtaacag atcaaggaag caatcaatta 1740
accatggatg attatgtgca cacacaatta atctggtctc taacaaaatc atctgacata 1800
cgaggtacaa tgcagcgctt cgtggattat tatatggtgg atcgatctaa tgatagtaca 1860
gaaaacgaag ccattcctaa ttacagcttt gtacgtgcac acgacagcga agtgcaaacg 1920
gttattgccc aaattgtttc cgatttgtat cctgatgttg aaaatagttt agcaccaaca 1980
acagaacaat tggcagctgc tttcaaagta tacaatgaag atgaaaaatt agcagacaaa 2040
aagtacacac aatataatat ggctagtgct tatgcgatgt tgctaaccaa taaggatact 2100
gttcctcgtg tctattatgg cgatttatat acagatgatg gtcaatatat ggcaacaaag 2160
tcaccatact atgatgcgat taacactttg ctaaaggcta gagttcagta tgttgctggt 2220
ggccaatcga tgtccgttga tagtaatgac gtgttaacaa gtgttcgcta tggtaaagat 2280
gccatgacag cttctgacac tggaacatct gagacgcgta ctgaaggtat tggagtcatc 2340
gtcagcaata acgcggagct acaattagag gatgggcata ctgtcacatt gcatatgggg 2400
gcagctcata agaaccaagc ttatcgtgct ttgttatcaa caactgcaga tggattagct 2460
tattatgata ctgatgaaaa tgcacctgtg gcgtacacag atgctaacgg cgatttgatt 2520
tttacgaatg aatcaattta tggtgtacaa aatccacaag tttctggtta cttggcagtt 2580
tgggttccgg taggtgcgca acaagatcaa gatgcacgaa cggcctctga tacaacaaca 2640
aacacgagtg ataaagtgtt ccattcaaac gctgctcttg attctcaagt catctacgaa 2700
ggtttctcaa acttccaagc atttgctaca gacagcagtg aatatacaaa cgtagtcatc 2760
gctcagaatg cggaccaatt taagcaatgg ggtgtgacaa gcttccaatt ggcaccacaa 2820
tatcgttcaa gtacagatac aagtttcttg gattcaatta ttcaaaacgg gtatgcattc 2880
acggatcgtt atgacttagg ttatggcaca ccgacaaaat atggaactgc tgatcagttg 2940
cgcgatgcta ttaaagcctt acatgctagc ggtattcaag ccattgccga ttgggtgccg 3000
gaccaaattt ataatttgcc agagcaagaa ttagctactg tcacaagaac aaattcattt 3060
ggagatgacg atacagattc tgatattgac aatgccttat atgttgtaca aagtcgtggg 3120
ggtggtcaat atcaagagat gtatggtggt gccttcttag aagagttaca ggcactctat 3180
ccatccctat ttaaagtgaa tcaaatctca actggcgttc caattgatgg cagtgtaaag 3240
attactgagt gggcggctaa gtacttcaat ggctctaaca tccaaggtaa aggtgctgga 3300
tacgtattga aagatatggg ttctaataag tactttaagg tcgtttcgaa cactgaggat 3360
ggtgactact taccaaaaca gttaactaat gatctgtcag aaactggcta caagggcgag 3420
cttgaaggta agcctatccc taaccctctc ctcggtctcg attctacgcg taccggtcat 3480
catcaccatc accat 3495

<210> SEQ ID NO 4
<211> LENGTH: 3105
<212> TYPE: DNA
<213> ORGANISM: Artificial
<220> FEATURE:
<223> OTHER INFORMATION: Truncated dextrane saccharase

<400> SEQUENCE: 4
atgggatctg ataaaattat tcatctgact gatgattctt ttgatactga tgtacttaag 60
gcagatggtg caatcctggt tgatttctgg gcacactggt gcggtccgtg caaaatgatc 120
gctccgattc tggatgaaat cgctgacgaa tatcagggca aactgaccgt tgcaaaactg 180
aacatcgatc acaacccggg cactgcgccg aaatatggca tccgtggtat cccgactctg 240

-continued

```
ctgctgttca aaaacggtga agtggcggca accaaagtgg gtgcactgtc taaaggtcag    300
ttgaaagagt tcctcgacgc taacctggcc ggctctggat ccggtgatga cgatgacaag    360
ctcgccctta tgggcttctc tggtgtgatt gatggtcaaa taatgacatt tgatcaggaa    420
acagggcaag aagtttctaa cacaacttct gaaataaaag aaggtttgac gactcaaaac    480
acggattata gcgaacataa tgcagcccac ggtacggatg ctgaggactt tgaaaatatt    540
gacggctatt taacagctag ttcatggtat cgtccaacag gtattttacg taacggaaca    600
gactgggaac cttctacaga tacagatttc agaccaatat tgtcagtgtg gtggccagat    660
aagaacaccc aggtcaatta tttaaattac atggctgatt tagggtttat cagtaatgcg    720
gacagttttg aaactgggga tagccaaagc ttattaaatg aagcaagtaa ctatgttcaa    780
aaatcaattg aaatgaaaat tagtgcgcaa caaagtacag agtggttaaa ggatgcaatg    840
gcggccttca ttgtcgcgca accacagtgg aatgaaacta gtgaagatat gagcaatgac    900
catttacaaa atggcgcatt aacttatgtc aacagtccac tgacacctga cgctaattca    960
aactttagac tacttaatcg gacaccaaca aaccagactg gtgaacaagc gtataattta   1020
gataattcaa aaggtggttt tgaattgttg ttagccaatg acgttgataa ttcaaaccct   1080
gtagtacaag cagaacaatt gaattggtta tattatttaa tgaattttgg tacgattacg   1140
gccaacgacg cggatgctaa ttttgatggt attcgtgtag atgcagtcga caatgtggat   1200
gctgatttgt tacaaattgc tgccgattat ttcaaactag cttacggtgt tgatcaaaat   1260
gatgctactg ctaatcagca tctttcaatt ttggaagatt ggagtcacaa tgatcctttg   1320
tatgtaacag atcaaggaag caatcaatta accatggatg attatgtgca cacacaatta   1380
atctggtctc taacaaaatc atctgacata cgaggtacaa tgcagcgctt cgtggattat   1440
tatatggtgg atcgatctaa tgatagtaca gaaaacgaag ccattcctaa ttacagcttt   1500
gtacgtgcac acgacagcga agtgcaaacg gttattgccc aaattgtttc cgatttgtat   1560
cctgatgttg aaaatagttt agcaccaaca acagaacaat tggcagctgc tttcaaagta   1620
tacaatgaag atgaaaaatt agcagacaaa aagtacacac aatataatat ggctagtgct   1680
tatgcgatgt tgctaaccaa taaggatact gttcctcgtg tctattatgg cgatttatat   1740
acagatgatg gtcaatatat ggcaacaaag tcaccatact atgatgcgat taacactttg   1800
ctaaaggcta gagttcagta tgttgctggt ggccaatcga tgtccgttga tagtaatgac   1860
gtgttaacaa gtgttcgcta tggtaaagat gccatgacag cttctgacac tggaacatct   1920
gagacgcgta ctgaaggtat tggagtcatc gtcagcaata acgcggagct acaattagag   1980
gatgggcata ctgtcacatt gcatatgggg gcagctcata agaaccaagc ttatcgtgct   2040
ttgttatcaa caactgcaga tggattagct tattatgata ctgatgaaaa tgcacctgtg   2100
gcgtacacag atgctaacgg cgatttgatt tttacgaatg aatcaattta tggtgtacaa   2160
aatccacaag tttctggtta cttggcagtt tgggttccgg taggtgcgca acaagatcaa   2220
gatgcacgaa cggcctctga tacaacaaca aacacgagtg ataaagtgtt ccattcaaac   2280
gctgctcttg attctcaagt catctacgaa ggtttctcaa acttccaagc atttgctaca   2340
gacagcagtg aatatacaaa cgtagtcatc gctcagaatg cggaccaatt taagcaatgg   2400
ggtgtgacaa gcttccaatt ggcaccacaa tatcgttcaa gtacagatac aagtttcttg   2460
gattcaatta ttcaaaacgg gtatgcattc acggatcgtt atgacttagg ttatggcaca   2520
ccgacaaaat atggaactgc tgatcagttg cgcgatgcta ttaaagcctt acatgctagc   2580
```

-continued

```
ggtattcaag ccattgccga ttgggtgccg gaccaaattt ataatttgcc agagcaagaa   2640

ttagctactg tcacaagaac aaattcattt ggagatgacg atacagattc tgatattgac   2700

aatgccttat atgttgtaca aagtcgtggg ggtggtcaat atcaagagat gtatggtggt   2760

gccttcttag aagagttaca ggcactctat ccatccctat ttaaagtgaa tcaaatctca   2820

actggcgttc caattgatgg cagtgtaaag attactgagt gggcggctaa gtacttcaat   2880

ggctctaaca tccaaggtaa aggtgctgga tacgtattga aagatatggg ttctaataag   2940

tactttaagg tcgtttcgaa cactgaggat ggtgactact taccaaaaca gttaactaat   3000

gatctgtcag aaactggcta caagggcgag cttgaaggta agcctatccc taaccctctc   3060

ctcggtctcg attctacgcg taccggtcat catcaccatc accat                   3105
```

<210> SEQ ID NO 5
<211> LENGTH: 4356
<212> TYPE: DNA
<213> ORGANISM: Artificial
<220> FEATURE:
<223> OTHER INFORMATION: Mutant dextrane saccharase

<400> SEQUENCE: 5

```
atgggatctg ataaaattat tcatctgact gatgattctt ttgatactga tgtacttaag     60

gcagatggtg caatcctggt tgatttctgg gcacactggt gcggtccgtg caaaatgatc    120

gctccgattc tggatgaaat cgctgacgaa tatcagggca aactgaccgt tgcaaaactg    180

aacatcgatc acaacccggg cactgcgccg aaatatggca tccgtggtat cccgactctg    240

ctgctgttca aaaacggtga agtggcggca accaaagtgg gtgcactgtc taaaggtcag    300

ttgaaagagt tcctcgacgc taacctggcc ggctctggat ccggtgatga cgatgacaag    360

ctcgccctta tgacacaaca agttagcggc aagtacgttg aaaaagacgg tagttggtat    420

tattattttg atgatggcaa aaatgctaaa ggtttatcaa cgatagacaa caatattcaa    480

tatttttacg agagtggtaa acaagccaaa ggacagtatg tcacaattga taatcaaaca    540

tattattttg ataagggctc aggtgatgag ttaactggtc tgcaaagcat tgatgggaac    600

atagttgctt ttaacgatga agggcaacaa atttttaatc aatattacca atctgaaaat    660

ggtacaacat actactttga tgataaagga cacgctgcta ccggtattaa gaatatcgag    720

ggcaaaaatt attattttga taatcttggg caactaaaaa aaggcttctc tggtgtgatt    780

gatggtcaaa taatgacatt tgatcaggaa acagggcaag aagtttctaa cacaacttct    840

gaaataaaag aaggtttgac gactcaaaac acggattata gcgaacataa tgcagcccac    900

ggtacggatg ctgaggactt tgaaaatatt gacggctatt taacagctag ttcatggtat    960

cgtccaacag gtattttacg taacggaaca gactgggaac cttctacaga tacagatttc   1020

agaccaatat tgtcagtgtg gtggccagat aagaacaccc aggtcaatta tttaaattac   1080

atggctgatt tagggtttat cagtaatgcg gacagttttg aaactgggga tagccaaagc   1140

ttattaaatg aagcaagtaa ctatgttcaa aaatcaattg aaatgaaaat tagtgcgcaa   1200

caaagtacag agtggttaaa ggatgcaatg gcggccttca ttgtcgcgca accacagtgg   1260

aatgaaacta gtgaagatat gagcaatgac catttacaaa atggcgcatt aacttatgtc   1320

aacagtccac tgacacctga cgctaattca aactttagac tacttaatcg gacaccaaca   1380

aaccagactg gtgaacaagc gtataattta gataattcaa aaggtggttt tgaattgttg   1440

ttagccaatg acgttgataa ttcaaaccct gtagtacaag cagaacaatt gaattggtta   1500

tattatttaa tgaattttgg tacgattacg gccaacgacg cggatgctaa ttttgatggt   1560
```

-continued

```
attcgtgtag atgcagtcga caatgtggat gctgatttgt tacaaattgc tgccgattat   1620
ttcaaactag cttacggtgt tgatcaaaat gatgctactg ctaatcagca tctttcaatt   1680
ttggaagatt ggagtcacaa tgatcctttg tatgtaacag atcaaggaag caatcaatta   1740
accatggatg attatgtgca cacacaatta atctggtctc taacaaaatc atctgacata   1800
cgaggtacaa tgcagcgctt cgtggattat tatatggtgg atcgatctaa tgatagtaca   1860
gaaaacgaag ccattcctaa ttacagcttt gtacgagctc acgactacga cgcgcaaacg   1920
gttattgccc aaattgtttc cgatttgtat cctgatgttg aaaatagttt agcaccaaca   1980
acagaacaat tggcagctgc tttcaaagta tacaatgaag atgaaaaatt agcagacaaa   2040
aagtacacac aatataatat ggctagtgct tatgcgatgt tgctaaccaa taaggatact   2100
gttcctcgtg tctattatgg cgatttatat acagatgatg gtcaatatat ggcaacaaag   2160
tcaccatact atgatgcgat taacactttg ctaaaggcta gagttcagta tgttgctggt   2220
ggccaatcga tgtccgttga tagtaatgac gtgttaacaa gtgttcgcta tggtaaagat   2280
gccatgacag cttctgacac tggaacatct gagacgcgta ctgaaggtat tggagtcatc   2340
gtcagcaata acgcggagct acaattagag gatgggcata ctgtcacatt gcatatgggg   2400
gcagctcata agaaccaagc ttatcgtgct ttgttatcaa caactgcaga tggattagct   2460
tattatgata ctgatgaaaa tgcacctgtg gcgtacacag atgctaacgg cgatttgatt   2520
tttacgaatg aatcaattta tggtgtacaa aatccacaag tttctggtta cttggcagtt   2580
tgggttccgg taggtgcgca acaagatcaa gatgcacgaa cggcctctga tacaacaaca   2640
aacacgagtg ataaagtgtt ccattcaaac gctgctcttg attctcaagt catctacgaa   2700
ggtttctcaa acttccaagc atttgctaca gacagcagtg aatatacaaa cgtagtcatc   2760
gctcagaatg cggaccaatt taagcaatgg ggtgtgacaa gcttccaatt ggcaccacaa   2820
tatcgttcaa gtacagatac aagtttcttg gattcaatta ttcaaaacgg gtatgcattc   2880
acggatcgtt atgacttagg ttatggcaca ccgacaaaat atggaactgc tgatcagttg   2940
cgcgatgcta ttaaagcctt acatgctagc ggtattcaag ccattgccga ttgggtgccg   3000
gaccaaattt ataatttgcc agagcaagaa ttagctactg tcacaagaac aaattcattt   3060
ggagatgacg atacagattc tgatattgac aatgccttat atgttgtaca aagtcgtggg   3120
ggtggtcaat atcaagagat gtatggtggt gccttcttag aagagttaca ggcactctat   3180
ccatccctat ttaaagtgaa tcaaatctca actggcgttc caattgatgg cagtgtaaag   3240
attactgagt gggcggctaa gtacttcaat ggctctaaca tccaaggtaa aggtgctgga   3300
tacgtattga aagatatggg ttctaataag tactttaagg tcgtttcgaa cactgaggat   3360
ggtgactact taccaaaaca gttaactaat gatctgtcag aaactggctt tacacacgat   3420
gataaaggaa tcatctatta tacattaagt ggttatcgtg cccaaaatgc atttattcaa   3480
gatgatgata ataactatta ctattttgat aaaacaggtc atttagtaac aggtttgcaa   3540
aagattaata accataccta cttcttctta cctaatggta tcgaactggt caagagcttc   3600
ttacaaaacg aagatggtac aattgtttat ttcgataaga aaggtcatca agtttttgat   3660
caatatataa ctgatcaaaa tggaaatgcg tattactttg atgatgctgg tgtaatgctt   3720
aaatcagggc ttgcaacgat tgatggacat caacagtatt ttgatcaaaa tggtgtgcag   3780
gttaaggata agtttgtgat tggcactgat ggttataagt attactttga accaggtagt   3840
ggtaacttag ctatcctacg ttatgtgcaa aatagtaaga atcaatggtt ctattttgat   3900
```

-continued

```
ggtaatggcc atgctgtcac tggtttccaa acaattaatg gtaaaaaaca atatttctat   3960

aatgatggtc atcaaagtaa aggtgaattc attgatgcag acggggatac tttctatacg   4020

agtgccactg atggtcgcct agtaactggt gttcagaaga ttaatggtat tacctatgct   4080

tttgataaca caggaaattt gatcacaaat cagtattatc aattagcaga tggtaaatat   4140

atgttgttag atgatagtgg tcgtgcgaaa acagggtttg tattgcaaga tggtgtacta   4200

agatacttcg atcaaaacgg tgagcaagtg aaagatgcta tcattgtgga tccagatact   4260

aacttgagtt acaagggcga gcttgaaggt aagcctatcc ctaaccctct cctcggtctc   4320

gattctacgc gtaccggtca tcatcaccat caccat                             4356


<210> SEQ ID NO 6
<211> LENGTH: 1452
<212> TYPE: PRT
<213> ORGANISM: Artificial
<220> FEATURE:
<223> OTHER INFORMATION: Truncated dextrane saccharase

<400> SEQUENCE: 6

Met Gly Ser Asp Lys Ile Ile His Leu Thr Asp Asp Ser Phe Asp Thr
1               5                   10                  15

Asp Val Leu Lys Ala Asp Gly Ala Ile Leu Val Asp Phe Trp Ala His
            20                  25                  30

Trp Cys Gly Pro Cys Lys Met Ile Ala Pro Ile Leu Asp Glu Ile Ala
        35                  40                  45

Asp Glu Tyr Gln Gly Lys Leu Thr Val Ala Lys Leu Asn Ile Asp His
    50                  55                  60

Asn Pro Gly Thr Ala Pro Lys Tyr Gly Ile Arg Gly Ile Pro Thr Leu
65                  70                  75                  80

Leu Leu Phe Lys Asn Gly Glu Val Ala Ala Thr Lys Val Gly Ala Leu
                85                  90                  95

Ser Lys Gly Gln Leu Lys Glu Phe Leu Asp Ala Asn Leu Ala Gly Ser
            100                 105                 110

Gly Ser Gly Asp Asp Asp Asp Lys Leu Ala Leu Met Thr Gln Gln Val
        115                 120                 125

Ser Gly Lys Tyr Val Glu Lys Asp Gly Ser Trp Tyr Tyr Tyr Phe Asp
    130                 135                 140

Asp Gly Lys Asn Ala Lys Gly Leu Ser Thr Ile Asp Asn Asn Ile Gln
145                 150                 155                 160

Tyr Phe Tyr Glu Ser Gly Lys Gln Ala Lys Gly Gln Tyr Val Thr Ile
                165                 170                 175

Asp Asn Gln Thr Tyr Tyr Phe Asp Lys Gly Ser Gly Asp Glu Leu Thr
            180                 185                 190

Gly Leu Gln Ser Ile Asp Gly Asn Ile Val Ala Phe Asn Asp Glu Gly
        195                 200                 205

Gln Gln Ile Phe Asn Gln Tyr Tyr Gln Ser Glu Asn Gly Thr Thr Tyr
    210                 215                 220

Tyr Phe Asp Asp Lys Gly His Ala Ala Thr Gly Ile Lys Asn Ile Glu
225                 230                 235                 240

Gly Lys Asn Tyr Tyr Phe Asp Asn Leu Gly Gln Leu Lys Lys Gly Phe
                245                 250                 255

Ser Gly Val Ile Asp Gly Gln Ile Met Thr Phe Asp Gln Glu Thr Gly
            260                 265                 270

Gln Glu Val Ser Asn Thr Thr Ser Glu Ile Lys Glu Gly Leu Thr Thr
        275                 280                 285
```

-continued

```
Gln Asn Thr Asp Tyr Ser Glu His Asn Ala Ala His Gly Thr Asp Ala
    290                 295                 300

Glu Asp Phe Glu Asn Ile Asp Gly Tyr Leu Thr Ala Ser Ser Trp Tyr
305                 310                 315                 320

Arg Pro Thr Gly Ile Leu Arg Asn Gly Thr Asp Trp Glu Pro Ser Thr
                325                 330                 335

Asp Thr Asp Phe Arg Pro Ile Leu Ser Val Trp Trp Pro Asp Lys Asn
            340                 345                 350

Thr Gln Val Asn Tyr Leu Asn Tyr Met Ala Asp Leu Gly Phe Ile Ser
        355                 360                 365

Asn Ala Asp Ser Phe Glu Thr Gly Asp Ser Gln Ser Leu Leu Asn Glu
    370                 375                 380

Ala Ser Asn Tyr Val Gln Lys Ser Ile Glu Met Lys Ile Ser Ala Gln
385                 390                 395                 400

Gln Ser Thr Glu Trp Leu Lys Asp Ala Met Ala Ala Phe Ile Val Ala
                405                 410                 415

Gln Pro Gln Trp Asn Glu Thr Ser Glu Asp Met Ser Asn Asp His Leu
            420                 425                 430

Gln Asn Gly Ala Leu Thr Tyr Val Asn Ser Pro Leu Thr Pro Asp Ala
        435                 440                 445

Asn Ser Asn Phe Arg Leu Leu Asn Arg Thr Pro Thr Asn Gln Thr Gly
    450                 455                 460

Glu Gln Ala Tyr Asn Leu Asp Asn Ser Lys Gly Gly Phe Glu Leu Leu
465                 470                 475                 480

Leu Ala Asn Asp Val Asp Asn Ser Asn Pro Val Val Gln Ala Glu Gln
                485                 490                 495

Leu Asn Trp Leu Tyr Tyr Leu Met Asn Phe Gly Thr Ile Thr Ala Asn
            500                 505                 510

Asp Ala Asp Ala Asn Phe Asp Gly Ile Arg Val Asp Ala Val Asp Asn
        515                 520                 525

Val Asp Ala Asp Leu Leu Gln Ile Ala Ala Asp Tyr Phe Lys Leu Ala
    530                 535                 540

Tyr Gly Val Asp Gln Asn Asp Ala Thr Ala Asn Gln His Leu Ser Ile
545                 550                 555                 560

Leu Glu Asp Trp Ser His Asn Asp Pro Leu Tyr Val Thr Asp Gln Gly
                565                 570                 575

Ser Asn Gln Leu Thr Met Asp Asp Tyr Val His Thr Gln Leu Ile Trp
            580                 585                 590

Ser Leu Thr Lys Ser Ser Asp Ile Arg Gly Thr Met Gln Arg Phe Val
        595                 600                 605

Asp Tyr Tyr Met Val Asp Arg Ser Asn Asp Ser Thr Glu Asn Glu Ala
    610                 615                 620

Ile Pro Asn Tyr Ser Phe Val Arg Ala His Asp Ser Glu Val Gln Thr
625                 630                 635                 640

Val Ile Ala Gln Ile Val Ser Asp Leu Tyr Pro Asp Val Glu Asn Ser
                645                 650                 655

Leu Ala Pro Thr Thr Glu Gln Leu Ala Ala Ala Phe Lys Val Tyr Asn
            660                 665                 670

Glu Asp Glu Lys Leu Ala Asp Lys Lys Tyr Thr Gln Tyr Asn Met Ala
        675                 680                 685

Ser Ala Tyr Ala Met Leu Leu Thr Asn Lys Asp Thr Val Pro Arg Val
    690                 695                 700
```

-continued

```
Tyr Tyr Gly Asp Leu Tyr Thr Asp Asp Gly Gln Tyr Met Ala Thr Lys
705                 710                 715                 720

Ser Pro Tyr Tyr Asp Ala Ile Asn Thr Leu Leu Lys Ala Arg Val Gln
                725                 730                 735

Tyr Val Ala Gly Gly Gln Ser Met Ser Val Asp Ser Asn Asp Val Leu
            740                 745                 750

Thr Ser Val Arg Tyr Gly Lys Asp Ala Met Thr Ala Ser Asp Thr Gly
        755                 760                 765

Thr Ser Glu Thr Arg Thr Glu Gly Ile Gly Val Ile Val Ser Asn Asn
    770                 775                 780

Ala Glu Leu Gln Leu Glu Asp Gly His Thr Val Thr Leu His Met Gly
785                 790                 795                 800

Ala Ala His Lys Asn Gln Ala Tyr Arg Ala Leu Leu Ser Thr Thr Ala
                805                 810                 815

Asp Gly Leu Ala Tyr Tyr Asp Thr Asp Glu Asn Ala Pro Val Ala Tyr
            820                 825                 830

Thr Asp Ala Asn Gly Asp Leu Ile Phe Thr Asn Glu Ser Ile Tyr Gly
        835                 840                 845

Val Gln Asn Pro Gln Val Ser Gly Tyr Leu Ala Val Trp Val Pro Val
    850                 855                 860

Gly Ala Gln Gln Asp Gln Asp Ala Arg Thr Ala Ser Asp Thr Thr Thr
865                 870                 875                 880

Asn Thr Ser Asp Lys Val Phe His Ser Asn Ala Ala Leu Asp Ser Gln
                885                 890                 895

Val Ile Tyr Glu Gly Phe Ser Asn Phe Gln Ala Phe Ala Thr Asp Ser
            900                 905                 910

Ser Glu Tyr Thr Asn Val Val Ile Ala Gln Asn Ala Asp Gln Phe Lys
        915                 920                 925

Gln Trp Gly Val Thr Ser Phe Gln Leu Ala Pro Gln Tyr Arg Ser Ser
    930                 935                 940

Thr Asp Thr Ser Phe Leu Asp Ser Ile Ile Gln Asn Gly Tyr Ala Phe
945                 950                 955                 960

Thr Asp Arg Tyr Asp Leu Gly Tyr Gly Thr Pro Thr Lys Tyr Gly Thr
                965                 970                 975

Ala Asp Gln Leu Arg Asp Ala Ile Lys Ala Leu His Ala Ser Gly Ile
            980                 985                 990

Gln Ala Ile Ala Asp Trp Val Pro  Asp Gln Ile Tyr Asn  Leu Pro Glu
        995                 1000                1005

Gln Glu  Leu Ala Thr Val Thr  Arg Thr Asn Ser Phe  Gly Asp Asp
    1010                 1015                1020

Asp Thr  Asp Ser Asp Ile Asp  Asn Ala Leu Tyr Val  Val Gln Ser
    1025                 1030                1035

Arg Gly  Gly Gly Gln Tyr Gln  Glu Met Tyr Gly Gly  Ala Phe Leu
    1040                 1045                1050

Glu Glu  Leu Gln Ala Leu Tyr  Pro Ser Leu Phe Lys  Val Asn Gln
    1055                 1060                1065

Ile Ser  Thr Gly Val Pro Ile  Asp Gly Ser Val Lys  Ile Thr Glu
    1070                 1075                1080

Trp Ala  Ala Lys Tyr Phe Asn  Gly Ser Asn Ile Gln  Gly Lys Gly
    1085                 1090                1095

Ala Gly  Tyr Val Leu Lys Asp  Met Gly Ser Asn Lys  Tyr Phe Lys
    1100                 1105                1110

Val Val  Ser Asn Thr Glu Asp  Gly Asp Tyr Leu Pro  Lys Gln Leu
```

-continued

```
    1115                1120                1125

Thr Asn  Asp Leu Ser Glu Thr  Gly Phe Thr His Asp  Asp Lys Gly
    1130                1135                1140

Ile Ile  Tyr Tyr Thr Leu Ser  Gly Tyr Arg Ala Gln  Asn Ala Phe
    1145                1150                1155

Ile Gln  Asp Asp Asp Asn Asn  Tyr Tyr Tyr Phe Asp  Lys Thr Gly
    1160                1165                1170

His Leu  Val Thr Gly Leu Gln  Lys Ile Asn Asn His  Thr Tyr Phe
    1175                1180                1185

Phe Leu  Pro Asn Gly Ile Glu  Leu Val Lys Ser Phe  Leu Gln Asn
    1190                1195                1200

Glu Asp  Gly Thr Ile Val Tyr  Phe Asp Lys Lys Gly  His Gln Val
    1205                1210                1215

Phe Asp  Gln Tyr Ile Thr Asp  Gln Asn Gly Asn Ala  Tyr Tyr Phe
    1220                1225                1230

Asp Asp  Ala Gly Val Met Leu  Lys Ser Gly Leu Ala  Thr Ile Asp
    1235                1240                1245

Gly His  Gln Gln Tyr Phe Asp  Gln Asn Gly Val Gln  Val Lys Asp
    1250                1255                1260

Lys Phe  Val Ile Gly Thr Asp  Gly Tyr Lys Tyr Tyr  Phe Glu Pro
    1265                1270                1275

Gly Ser  Gly Asn Leu Ala Ile  Leu Arg Tyr Val Gln  Asn Ser Lys
    1280                1285                1290

Asn Gln  Trp Phe Tyr Phe Asp  Gly Asn Gly His Ala  Val Thr Gly
    1295                1300                1305

Phe Gln  Thr Ile Asn Gly Lys  Lys Gln Tyr Phe Tyr  Asn Asp Gly
    1310                1315                1320

His Gln  Ser Lys Gly Glu Phe  Ile Asp Ala Asp Gly  Asp Thr Phe
    1325                1330                1335

Tyr Thr  Ser Ala Thr Asp Gly  Arg Leu Val Thr Gly  Val Gln Lys
    1340                1345                1350

Ile Asn  Gly Ile Thr Tyr Ala  Phe Asp Asn Thr Gly  Asn Leu Ile
    1355                1360                1365

Thr Asn  Gln Tyr Tyr Gln Leu  Ala Asp Gly Lys Tyr  Met Leu Leu
    1370                1375                1380

Asp Asp  Ser Gly Arg Ala Lys  Thr Gly Phe Val Leu  Gln Asp Gly
    1385                1390                1395

Val Leu  Arg Tyr Phe Asp Gln  Asn Gly Glu Gln Val  Lys Asp Ala
    1400                1405                1410

Ile Ile  Val Asp Pro Asp Thr  Asn Leu Ser Tyr Lys  Gly Glu Leu
    1415                1420                1425

Glu Gly  Lys Pro Ile Pro Asn  Pro Leu Leu Gly Leu  Asp Ser Thr
    1430                1435                1440

Arg Thr  Gly His His His His  His His
    1445                1450
```

<210> SEQ ID NO 7
<211> LENGTH: 1364
<212> TYPE: PRT
<213> ORGANISM: Artificial
<220> FEATURE:
<223> OTHER INFORMATION: Truncated dextrane saccharase

<400> SEQUENCE: 7

Met Gly Ser Asp Lys Ile Ile His Leu Thr Asp Asp Ser Phe Asp Thr

-continued

```
1               5                   10                  15

Asp Val Leu Lys Ala Asp Gly Ala Ile Leu Val Asp Phe Trp Ala His
            20                  25                  30

Trp Cys Gly Pro Cys Lys Met Ile Ala Pro Ile Leu Asp Glu Ile Ala
        35                  40                  45

Asp Glu Tyr Gln Gly Lys Leu Thr Val Ala Lys Leu Asn Ile Asp His
    50                  55                  60

Asn Pro Gly Thr Ala Pro Lys Tyr Gly Ile Arg Gly Ile Pro Thr Leu
65                  70                  75                  80

Leu Leu Phe Lys Asn Gly Glu Val Ala Ala Thr Lys Val Gly Ala Leu
                85                  90                  95

Ser Lys Gly Gln Leu Lys Glu Phe Leu Asp Ala Asn Leu Ala Gly Ser
            100                 105                 110

Gly Ser Gly Asp Asp Asp Asp Lys Leu Ala Leu Met Thr Gln Gln Val
        115                 120                 125

Ser Gly Lys Tyr Val Glu Lys Asp Gly Ser Trp Tyr Tyr Tyr Phe Asp
    130                 135                 140

Asp Gly Lys Asn Ala Lys Gly Leu Ser Thr Ile Asp Asn Asn Ile Gln
145                 150                 155                 160

Tyr Phe Tyr Glu Ser Gly Lys Gln Ala Lys Gly Gln Tyr Val Thr Ile
                165                 170                 175

Asp Asn Gln Thr Tyr Tyr Phe Asp Lys Gly Ser Gly Asp Glu Leu Thr
            180                 185                 190

Gly Leu Gln Ser Ile Asp Gly Asn Ile Val Ala Phe Asn Asp Glu Gly
        195                 200                 205

Gln Gln Ile Phe Asn Gln Tyr Tyr Gln Ser Glu Asn Gly Thr Thr Tyr
    210                 215                 220

Tyr Phe Asp Asp Lys Gly His Ala Ala Thr Gly Ile Lys Asn Ile Glu
225                 230                 235                 240

Gly Lys Asn Tyr Tyr Phe Asp Asn Leu Gly Gln Leu Lys Lys Gly Phe
                245                 250                 255

Ser Gly Val Ile Asp Gly Gln Ile Met Thr Phe Asp Gln Glu Thr Gly
            260                 265                 270

Gln Glu Val Ser Asn Thr Thr Ser Glu Ile Lys Glu Gly Leu Thr Thr
        275                 280                 285

Gln Asn Thr Asp Tyr Ser Glu His Asn Ala Ala His Gly Thr Asp Ala
    290                 295                 300

Glu Asp Phe Glu Asn Ile Asp Gly Tyr Leu Thr Ala Ser Ser Trp Tyr
305                 310                 315                 320

Arg Pro Thr Gly Ile Leu Arg Asn Gly Thr Asp Trp Glu Pro Ser Thr
                325                 330                 335

Asp Thr Asp Phe Arg Pro Ile Leu Ser Val Trp Trp Pro Asp Lys Asn
            340                 345                 350

Thr Gln Val Asn Tyr Leu Asn Tyr Met Ala Asp Leu Gly Phe Ile Ser
        355                 360                 365

Asn Ala Asp Ser Phe Glu Thr Gly Asp Ser Gln Ser Leu Leu Asn Glu
    370                 375                 380

Ala Ser Asn Tyr Val Gln Lys Ser Ile Glu Met Lys Ile Ser Ala Gln
385                 390                 395                 400

Gln Ser Thr Glu Trp Leu Lys Asp Ala Met Ala Ala Phe Ile Val Ala
                405                 410                 415

Gln Pro Gln Trp Asn Glu Thr Ser Glu Asp Met Ser Asn Asp His Leu
            420                 425                 430
```

```
Gln Asn Gly Ala Leu Thr Tyr Val Asn Ser Pro Leu Thr Pro Asp Ala
        435                 440                 445

Asn Ser Asn Phe Arg Leu Leu Asn Arg Thr Pro Thr Asn Gln Thr Gly
    450                 455                 460

Glu Gln Ala Tyr Asn Leu Asp Asn Ser Lys Gly Gly Phe Glu Leu Leu
465                 470                 475                 480

Leu Ala Asn Asp Val Asp Asn Ser Asn Pro Val Val Gln Ala Glu Gln
                485                 490                 495

Leu Asn Trp Leu Tyr Tyr Leu Met Asn Phe Gly Thr Ile Thr Ala Asn
            500                 505                 510

Asp Ala Asp Ala Asn Phe Asp Gly Ile Arg Val Asp Ala Val Asp Asn
        515                 520                 525

Val Asp Ala Asp Leu Leu Gln Ile Ala Ala Asp Tyr Phe Lys Leu Ala
    530                 535                 540

Tyr Gly Val Asp Gln Asn Asp Ala Thr Ala Asn Gln His Leu Ser Ile
545                 550                 555                 560

Leu Glu Asp Trp Ser His Asn Asp Pro Leu Tyr Val Thr Asp Gln Gly
                565                 570                 575

Ser Asn Gln Leu Thr Met Asp Asp Tyr Val His Thr Gln Leu Ile Trp
            580                 585                 590

Ser Leu Thr Lys Ser Ser Asp Ile Arg Gly Thr Met Gln Arg Phe Val
        595                 600                 605

Asp Tyr Tyr Met Val Asp Arg Ser Asn Asp Ser Thr Glu Asn Glu Ala
    610                 615                 620

Ile Pro Asn Tyr Ser Phe Val Arg Ala His Asp Ser Glu Val Gln Thr
625                 630                 635                 640

Val Ile Ala Gln Ile Val Ser Asp Leu Tyr Pro Asp Val Glu Asn Ser
                645                 650                 655

Leu Ala Pro Thr Thr Glu Gln Leu Ala Ala Ala Phe Lys Val Tyr Asn
            660                 665                 670

Glu Asp Glu Lys Leu Ala Asp Lys Lys Tyr Thr Gln Tyr Asn Met Ala
        675                 680                 685

Ser Ala Tyr Ala Met Leu Leu Thr Asn Lys Asp Thr Val Pro Arg Val
    690                 695                 700

Tyr Tyr Gly Asp Leu Tyr Thr Asp Asp Gly Gln Tyr Met Ala Thr Lys
705                 710                 715                 720

Ser Pro Tyr Tyr Asp Ala Ile Asn Thr Leu Leu Lys Ala Arg Val Gln
                725                 730                 735

Tyr Val Ala Gly Gly Gln Ser Met Ser Val Asp Ser Asn Asp Val Leu
            740                 745                 750

Thr Ser Val Arg Tyr Gly Lys Asp Ala Met Thr Ala Ser Asp Thr Gly
        755                 760                 765

Thr Ser Glu Thr Arg Thr Glu Gly Ile Gly Val Ile Val Ser Asn Asn
    770                 775                 780

Ala Glu Leu Gln Leu Glu Asp Gly His Thr Val Thr Leu His Met Gly
785                 790                 795                 800

Ala Ala His Lys Asn Gln Ala Tyr Arg Ala Leu Leu Ser Thr Thr Ala
                805                 810                 815

Asp Gly Leu Ala Tyr Tyr Asp Thr Asp Glu Asn Ala Pro Val Ala Tyr
            820                 825                 830

Thr Asp Ala Asn Gly Asp Leu Ile Phe Thr Asn Glu Ser Ile Tyr Gly
        835                 840                 845
```

-continued

Val Gln Asn Pro Gln Val Ser Gly Tyr Leu Ala Val Trp Val Pro Val
    850                 855                 860

Gly Ala Gln Gln Asp Gln Asp Ala Arg Thr Ala Ser Asp Thr Thr Thr
865                 870                 875                 880

Asn Thr Ser Asp Lys Val Phe His Ser Asn Ala Ala Leu Asp Ser Gln
                885                 890                 895

Val Ile Tyr Glu Gly Phe Ser Asn Phe Gln Ala Phe Ala Thr Asp Ser
            900                 905                 910

Ser Glu Tyr Thr Asn Val Val Ile Ala Gln Asn Ala Asp Gln Phe Lys
        915                 920                 925

Gln Trp Gly Val Thr Ser Phe Gln Leu Ala Pro Gln Tyr Arg Ser Ser
    930                 935                 940

Thr Asp Thr Ser Phe Leu Asp Ser Ile Ile Gln Asn Gly Tyr Ala Phe
945                 950                 955                 960

Thr Asp Arg Tyr Asp Leu Gly Tyr Gly Thr Pro Thr Lys Tyr Gly Thr
                965                 970                 975

Ala Asp Gln Leu Arg Asp Ala Ile Lys Ala Leu His Ala Ser Gly Ile
            980                 985                 990

Gln Ala Ile Ala Asp Trp Val Pro  Asp Gln Ile Tyr Asn  Leu Pro Glu
        995                 1000                 1005

Gln Glu  Leu Ala Thr Val Thr  Arg Thr Asn Ser Phe  Gly Asp Asp
    1010                 1015                 1020

Asp Thr  Asp Ser Asp Ile Asp  Asn Ala Leu Tyr Val  Val Gln Ser
    1025                 1030                 1035

Arg Gly  Gly Gly Gln Tyr Gln  Glu Met Tyr Gly Gly  Ala Phe Leu
    1040                 1045                 1050

Glu Glu  Leu Gln Ala Leu Tyr  Pro Ser Leu Phe Lys  Val Asn Gln
    1055                 1060                 1065

Ile Ser  Thr Gly Val Pro Ile  Asp Gly Ser Val Lys  Ile Thr Glu
    1070                 1075                 1080

Trp Ala  Ala Lys Tyr Phe Asn  Gly Ser Asn Ile Gln  Gly Lys Gly
    1085                 1090                 1095

Ala Gly  Tyr Val Leu Lys Asp  Met Gly Ser Asn Lys  Tyr Phe Lys
    1100                 1105                 1110

Val Val  Ser Asn Thr Glu Asp  Gly Asp Tyr Leu Pro  Lys Gln Leu
    1115                 1120                 1125

Thr Asn  Asp Leu Ser Glu Thr  Gly Phe Thr His Asp  Asp Lys Gly
    1130                 1135                 1140

Ile Ile  Tyr Tyr Thr Leu Ser  Gly Tyr Arg Ala Gln  Asn Ala Phe
    1145                 1150                 1155

Ile Gln  Asp Asp Asp Asn Asn  Tyr Tyr Tyr Phe Asp  Lys Thr Gly
    1160                 1165                 1170

His Leu  Val Thr Gly Leu Gln  Lys Ile Asn Asn His  Thr Tyr Phe
    1175                 1180                 1185

Phe Leu  Pro Asn Gly Ile Glu  Leu Val Lys Ser Phe  Leu Gln Asn
    1190                 1195                 1200

Glu Asp  Gly Thr Ile Val Tyr  Phe Asp Lys Lys Gly  His Gln Val
    1205                 1210                 1215

Phe Asp  Gln Tyr Ile Thr Asp  Gln Asn Gly Asn Ala  Tyr Tyr Phe
    1220                 1225                 1230

Asp Asp  Ala Gly Val Met Leu  Lys Ser Gly Leu Ala  Thr Ile Asp
    1235                 1240                 1245

Gly His  Gln Gln Tyr Phe Asp  Gln Asn Gly Val Gln  Val Lys Asp

-continued

```
    1250                1255                1260

Lys Phe  Val Ile Gly Thr Asp  Gly Tyr Lys Tyr Tyr  Phe Glu Pro
    1265                1270                1275

Gly Ser  Gly Asn Leu Ala Ile  Leu Arg Tyr Val Gln  Asn Ser Lys
    1280                1285                1290

Asn Gln  Trp Phe Tyr Phe Asp  Gly Asn Gly His Ala  Val Thr Gly
    1295                1300                1305

Phe Gln  Thr Ile Asn Gly Lys  Lys Gln Tyr Phe Tyr  Asn Asp Gly
    1310                1315                1320

His Gln  Ser Lys Gly Glu Phe  Ile Asp Ala Asp Gly  Tyr Lys Gly
    1325                1330                1335

Glu Leu  Glu Gly Lys Pro Ile  Pro Asn Pro Leu Leu  Gly Leu Asp
    1340                1345                1350

Ser Thr  Arg Thr Gly His His  His His His His
    1355                1360


<210> SEQ ID NO 8
<211> LENGTH: 1165
<212> TYPE: PRT
<213> ORGANISM: Artificial
<220> FEATURE:
<223> OTHER INFORMATION: Truncated dextrane saccharase

<400> SEQUENCE: 8

Met Gly Ser Asp Lys Ile Ile His Leu Thr Asp Asp Ser Phe Asp Thr
1               5                   10                  15

Asp Val Leu Lys Ala Asp Gly Ala Ile Leu Val Asp Phe Trp Ala His
            20                  25                  30

Trp Cys Gly Pro Cys Lys Met Ile Ala Pro Ile Leu Asp Glu Ile Ala
        35                  40                  45

Asp Glu Tyr Gln Gly Lys Leu Thr Val Ala Lys Leu Asn Ile Asp His
    50                  55                  60

Asn Pro Gly Thr Ala Pro Lys Tyr Gly Ile Arg Gly Ile Pro Thr Leu
65                  70                  75                  80

Leu Leu Phe Lys Asn Gly Glu Val Ala Ala Thr Lys Val Gly Ala Leu
                85                  90                  95

Ser Lys Gly Gln Leu Lys Glu Phe Leu Asp Ala Asn Leu Ala Gly Ser
            100                 105                 110

Gly Ser Gly Asp Asp Asp Asp Lys Leu Ala Leu Met Thr Gln Gln Val
        115                 120                 125

Ser Gly Lys Tyr Val Glu Lys Asp Gly Ser Trp Tyr Tyr Tyr Phe Asp
    130                 135                 140

Asp Gly Lys Asn Ala Lys Gly Leu Ser Thr Ile Asp Asn Asn Ile Gln
145                 150                 155                 160

Tyr Phe Tyr Glu Ser Gly Lys Gln Ala Lys Gly Gln Tyr Val Thr Ile
                165                 170                 175

Asp Asn Gln Thr Tyr Tyr Phe Asp Lys Gly Ser Gly Asp Glu Leu Thr
            180                 185                 190

Gly Leu Gln Ser Ile Asp Gly Asn Ile Val Ala Phe Asn Asp Glu Gly
        195                 200                 205

Gln Gln Ile Phe Asn Gln Tyr Tyr Gln Ser Glu Asn Gly Thr Thr Tyr
    210                 215                 220

Tyr Phe Asp Asp Lys Gly His Ala Ala Thr Gly Ile Lys Asn Ile Glu
225                 230                 235                 240

Gly Lys Asn Tyr Tyr Phe Asp Asn Leu Gly Gln Leu Lys Lys Gly Phe
```

-continued

```
                245                 250                 255

Ser Gly Val Ile Asp Gly Gln Ile Met Thr Phe Asp Gln Glu Thr Gly
            260                 265                 270

Gln Glu Val Ser Asn Thr Thr Ser Glu Ile Lys Glu Gly Leu Thr Thr
        275                 280                 285

Gln Asn Thr Asp Tyr Ser Glu His Asn Ala Ala His Gly Thr Asp Ala
    290                 295                 300

Glu Asp Phe Glu Asn Ile Asp Gly Tyr Leu Thr Ala Ser Ser Trp Tyr
305                 310                 315                 320

Arg Pro Thr Gly Ile Leu Arg Asn Gly Thr Asp Trp Glu Pro Ser Thr
                325                 330                 335

Asp Thr Asp Phe Arg Pro Ile Leu Ser Val Trp Trp Pro Asp Lys Asn
            340                 345                 350

Thr Gln Val Asn Tyr Leu Asn Tyr Met Ala Asp Leu Gly Phe Ile Ser
        355                 360                 365

Asn Ala Asp Ser Phe Glu Thr Gly Asp Ser Gln Ser Leu Leu Asn Glu
    370                 375                 380

Ala Ser Asn Tyr Val Gln Lys Ser Ile Glu Met Lys Ile Ser Ala Gln
385                 390                 395                 400

Gln Ser Thr Glu Trp Leu Lys Asp Ala Met Ala Ala Phe Ile Val Ala
                405                 410                 415

Gln Pro Gln Trp Asn Glu Thr Ser Glu Asp Met Ser Asn Asp His Leu
            420                 425                 430

Gln Asn Gly Ala Leu Thr Tyr Val Asn Ser Pro Leu Thr Pro Asp Ala
        435                 440                 445

Asn Ser Asn Phe Arg Leu Leu Asn Arg Thr Pro Thr Asn Gln Thr Gly
    450                 455                 460

Glu Gln Ala Tyr Asn Leu Asp Asn Ser Lys Gly Gly Phe Glu Leu Leu
465                 470                 475                 480

Leu Ala Asn Asp Val Asp Asn Ser Asn Pro Val Val Gln Ala Glu Gln
                485                 490                 495

Leu Asn Trp Leu Tyr Tyr Leu Met Asn Phe Gly Thr Ile Thr Ala Asn
            500                 505                 510

Asp Ala Asp Ala Asn Phe Asp Gly Ile Arg Val Asp Ala Val Asp Asn
        515                 520                 525

Val Asp Ala Asp Leu Leu Gln Ile Ala Ala Asp Tyr Phe Lys Leu Ala
    530                 535                 540

Tyr Gly Val Asp Gln Asn Asp Ala Thr Ala Asn Gln His Leu Ser Ile
545                 550                 555                 560

Leu Glu Asp Trp Ser His Asn Asp Pro Leu Tyr Val Thr Asp Gln Gly
                565                 570                 575

Ser Asn Gln Leu Thr Met Asp Asp Tyr Val His Thr Gln Leu Ile Trp
            580                 585                 590

Ser Leu Thr Lys Ser Ser Asp Ile Arg Gly Thr Met Gln Arg Phe Val
        595                 600                 605

Asp Tyr Tyr Met Val Asp Arg Ser Asn Asp Ser Thr Glu Asn Glu Ala
    610                 615                 620

Ile Pro Asn Tyr Ser Phe Val Arg Ala His Asp Ser Glu Val Gln Thr
625                 630                 635                 640

Val Ile Ala Gln Ile Val Ser Asp Leu Tyr Pro Asp Val Glu Asn Ser
                645                 650                 655

Leu Ala Pro Thr Thr Glu Gln Leu Ala Ala Ala Phe Lys Val Tyr Asn
            660                 665                 670
```

-continued

```
Glu Asp Glu Lys Leu Ala Asp Lys Lys Tyr Thr Gln Tyr Asn Met Ala
        675                 680                 685

Ser Ala Tyr Ala Met Leu Leu Thr Asn Lys Asp Thr Val Pro Arg Val
    690                 695                 700

Tyr Tyr Gly Asp Leu Tyr Thr Asp Asp Gly Gln Tyr Met Ala Thr Lys
705                 710                 715                 720

Ser Pro Tyr Tyr Asp Ala Ile Asn Thr Leu Leu Lys Ala Arg Val Gln
                725                 730                 735

Tyr Val Ala Gly Gly Gln Ser Met Ser Val Asp Ser Asn Asp Val Leu
            740                 745                 750

Thr Ser Val Arg Tyr Gly Lys Asp Ala Met Thr Ala Ser Asp Thr Gly
        755                 760                 765

Thr Ser Glu Thr Arg Thr Glu Gly Ile Gly Val Ile Val Ser Asn Asn
    770                 775                 780

Ala Glu Leu Gln Leu Glu Asp Gly His Thr Val Thr Leu His Met Gly
785                 790                 795                 800

Ala Ala His Lys Asn Gln Ala Tyr Arg Ala Leu Leu Ser Thr Thr Ala
                805                 810                 815

Asp Gly Leu Ala Tyr Tyr Asp Thr Asp Glu Asn Ala Pro Val Ala Tyr
            820                 825                 830

Thr Asp Ala Asn Gly Asp Leu Ile Phe Thr Asn Glu Ser Ile Tyr Gly
        835                 840                 845

Val Gln Asn Pro Gln Val Ser Gly Tyr Leu Ala Val Trp Val Pro Val
    850                 855                 860

Gly Ala Gln Gln Asp Gln Asp Ala Arg Thr Ala Ser Asp Thr Thr Thr
865                 870                 875                 880

Asn Thr Ser Asp Lys Val Phe His Ser Asn Ala Ala Leu Asp Ser Gln
                885                 890                 895

Val Ile Tyr Glu Gly Phe Ser Asn Phe Gln Ala Phe Ala Thr Asp Ser
            900                 905                 910

Ser Glu Tyr Thr Asn Val Val Ile Ala Gln Asn Ala Asp Gln Phe Lys
        915                 920                 925

Gln Trp Gly Val Thr Ser Phe Gln Leu Ala Pro Gln Tyr Arg Ser Ser
    930                 935                 940

Thr Asp Thr Ser Phe Leu Asp Ser Ile Ile Gln Asn Gly Tyr Ala Phe
945                 950                 955                 960

Thr Asp Arg Tyr Asp Leu Gly Tyr Gly Thr Pro Thr Lys Tyr Gly Thr
                965                 970                 975

Ala Asp Gln Leu Arg Asp Ala Ile Lys Ala Leu His Ala Ser Gly Ile
            980                 985                 990

Gln Ala Ile Ala Asp Trp Val Pro  Asp Gln Ile Tyr Asn  Leu Pro Glu
        995                 1000                1005

Gln Glu  Leu Ala Thr Val Thr  Arg Thr Asn Ser Phe  Gly Asp Asp
    1010                1015                1020

Asp Thr  Asp Ser Asp Ile Asp  Asn Ala Leu Tyr Val  Val Gln Ser
    1025                1030                1035

Arg Gly  Gly Gly Gln Tyr Gln  Glu Met Tyr Gly Gly  Ala Phe Leu
    1040                1045                1050

Glu Glu  Leu Gln Ala Leu Tyr  Pro Ser Leu Phe Lys  Val Asn Gln
    1055                1060                1065

Ile Ser  Thr Gly Val Pro Ile  Asp Gly Ser Val Lys  Ile Thr Glu
    1070                1075                1080
```

-continued

```
Trp Ala  Ala Lys Tyr Phe Asn  Gly Ser Asn Ile Gln  Gly Lys Gly
    1085                 1090                 1095

Ala Gly  Tyr Val Leu Lys Asp  Met Gly Ser Asn Lys  Tyr Phe Lys
    1100                 1105                 1110

Val Val  Ser Asn Thr Glu Asp  Gly Asp Tyr Leu Pro  Lys Gln Leu
    1115                 1120                 1125

Thr Asn  Asp Leu Ser Glu Thr  Gly Tyr Lys Gly Glu  Leu Glu Gly
    1130                 1135                 1140

Lys Pro  Ile Pro Asn Pro Leu  Leu Gly Leu Asp Ser  Thr Arg Thr
    1145                 1150                 1155

Gly His  His His His His His
    1160                 1165


<210> SEQ ID NO 9
<211> LENGTH: 1035
<212> TYPE: PRT
<213> ORGANISM: Artificial
<220> FEATURE:
<223> OTHER INFORMATION: Truncated dextrane saccharase

<400> SEQUENCE: 9

Met Gly Ser Asp Lys Ile Ile His Leu Thr Asp Asp Ser Phe Asp Thr
1               5                   10                  15

Asp Val Leu Lys Ala Asp Gly Ala Ile Leu Val Asp Phe Trp Ala His
            20                  25                  30

Trp Cys Gly Pro Cys Lys Met Ile Ala Pro Ile Leu Asp Glu Ile Ala
        35                  40                  45

Asp Glu Tyr Gln Gly Lys Leu Thr Val Ala Lys Leu Asn Ile Asp His
    50                  55                  60

Asn Pro Gly Thr Ala Pro Lys Tyr Gly Ile Arg Gly Ile Pro Thr Leu
65                  70                  75                  80

Leu Leu Phe Lys Asn Gly Glu Val Ala Ala Thr Lys Val Gly Ala Leu
                85                  90                  95

Ser Lys Gly Gln Leu Lys Glu Phe Leu Asp Ala Asn Leu Ala Gly Ser
            100                 105                 110

Gly Ser Gly Asp Asp Asp Asp Lys Leu Ala Leu Met Gly Phe Ser Gly
        115                 120                 125

Val Ile Asp Gly Gln Ile Met Thr Phe Asp Gln Glu Thr Gly Gln Glu
    130                 135                 140

Val Ser Asn Thr Thr Ser Glu Ile Lys Glu Gly Leu Thr Thr Gln Asn
145                 150                 155                 160

Thr Asp Tyr Ser Glu His Asn Ala Ala His Gly Thr Asp Ala Glu Asp
                165                 170                 175

Phe Glu Asn Ile Asp Gly Tyr Leu Thr Ala Ser Ser Trp Tyr Arg Pro
            180                 185                 190

Thr Gly Ile Leu Arg Asn Gly Thr Asp Trp Glu Pro Ser Thr Asp Thr
        195                 200                 205

Asp Phe Arg Pro Ile Leu Ser Val Trp Trp Pro Asp Lys Asn Thr Gln
    210                 215                 220

Val Asn Tyr Leu Asn Tyr Met Ala Asp Leu Gly Phe Ile Ser Asn Ala
225                 230                 235                 240

Asp Ser Phe Glu Thr Gly Asp Ser Gln Ser Leu Leu Asn Glu Ala Ser
                245                 250                 255

Asn Tyr Val Gln Lys Ser Ile Glu Met Lys Ile Ser Ala Gln Gln Ser
            260                 265                 270
```

-continued

Thr Glu Trp Leu Lys Asp Ala Met Ala Ala Phe Ile Val Ala Gln Pro
        275                 280                 285

Gln Trp Asn Glu Thr Ser Glu Asp Met Ser Asn Asp His Leu Gln Asn
    290                 295                 300

Gly Ala Leu Thr Tyr Val Asn Ser Pro Leu Thr Pro Asp Ala Asn Ser
305                 310                 315                 320

Asn Phe Arg Leu Leu Asn Arg Thr Pro Thr Asn Gln Thr Gly Glu Gln
                325                 330                 335

Ala Tyr Asn Leu Asp Asn Ser Lys Gly Gly Phe Glu Leu Leu Leu Ala
            340                 345                 350

Asn Asp Val Asp Asn Ser Asn Pro Val Val Gln Ala Glu Gln Leu Asn
        355                 360                 365

Trp Leu Tyr Tyr Leu Met Asn Phe Gly Thr Ile Thr Ala Asn Asp Ala
    370                 375                 380

Asp Ala Asn Phe Asp Gly Ile Arg Val Asp Ala Val Asp Asn Val Asp
385                 390                 395                 400

Ala Asp Leu Leu Gln Ile Ala Ala Asp Tyr Phe Lys Leu Ala Tyr Gly
                405                 410                 415

Val Asp Gln Asn Asp Ala Thr Ala Asn Gln His Leu Ser Ile Leu Glu
            420                 425                 430

Asp Trp Ser His Asn Asp Pro Leu Tyr Val Thr Asp Gln Gly Ser Asn
        435                 440                 445

Gln Leu Thr Met Asp Asp Tyr Val His Thr Gln Leu Ile Trp Ser Leu
    450                 455                 460

Thr Lys Ser Ser Asp Ile Arg Gly Thr Met Gln Arg Phe Val Asp Tyr
465                 470                 475                 480

Tyr Met Val Asp Arg Ser Asn Asp Ser Thr Glu Asn Glu Ala Ile Pro
                485                 490                 495

Asn Tyr Ser Phe Val Arg Ala His Asp Ser Glu Val Gln Thr Val Ile
            500                 505                 510

Ala Gln Ile Val Ser Asp Leu Tyr Pro Asp Val Glu Asn Ser Leu Ala
        515                 520                 525

Pro Thr Thr Glu Gln Leu Ala Ala Ala Phe Lys Val Tyr Asn Glu Asp
    530                 535                 540

Glu Lys Leu Ala Asp Lys Lys Tyr Thr Gln Tyr Asn Met Ala Ser Ala
545                 550                 555                 560

Tyr Ala Met Leu Leu Thr Asn Lys Asp Thr Val Pro Arg Val Tyr Tyr
                565                 570                 575

Gly Asp Leu Tyr Thr Asp Asp Gly Gln Tyr Met Ala Thr Lys Ser Pro
            580                 585                 590

Tyr Tyr Asp Ala Ile Asn Thr Leu Leu Lys Ala Arg Val Gln Tyr Val
        595                 600                 605

Ala Gly Gly Gln Ser Met Ser Val Asp Ser Asn Asp Val Leu Thr Ser
    610                 615                 620

Val Arg Tyr Gly Lys Asp Ala Met Thr Ala Ser Asp Thr Gly Thr Ser
625                 630                 635                 640

Glu Thr Arg Thr Glu Gly Ile Gly Val Ile Val Ser Asn Asn Ala Glu
                645                 650                 655

Leu Gln Leu Glu Asp Gly His Thr Val Thr Leu His Met Gly Ala Ala
            660                 665                 670

His Lys Asn Gln Ala Tyr Arg Ala Leu Leu Ser Thr Thr Ala Asp Gly
        675                 680                 685

Leu Ala Tyr Tyr Asp Thr Asp Glu Asn Ala Pro Val Ala Tyr Thr Asp

-continued

```
    690                 695                 700

Ala Asn Gly Asp Leu Ile Phe Thr Asn Glu Ser Ile Tyr Gly Val Gln
705                 710                 715                 720

Asn Pro Gln Val Ser Gly Tyr Leu Ala Val Trp Val Pro Val Gly Ala
                725                 730                 735

Gln Gln Asp Gln Asp Ala Arg Thr Ala Ser Asp Thr Thr Thr Asn Thr
            740                 745                 750

Ser Asp Lys Val Phe His Ser Asn Ala Ala Leu Asp Ser Gln Val Ile
        755                 760                 765

Tyr Glu Gly Phe Ser Asn Phe Gln Ala Phe Ala Thr Asp Ser Ser Glu
    770                 775                 780

Tyr Thr Asn Val Val Ile Ala Gln Asn Ala Asp Gln Phe Lys Gln Trp
785                 790                 795                 800

Gly Val Thr Ser Phe Gln Leu Ala Pro Gln Tyr Arg Ser Ser Thr Asp
                805                 810                 815

Thr Ser Phe Leu Asp Ser Ile Ile Gln Asn Gly Tyr Ala Phe Thr Asp
            820                 825                 830

Arg Tyr Asp Leu Gly Tyr Gly Thr Pro Thr Lys Tyr Gly Thr Ala Asp
        835                 840                 845

Gln Leu Arg Asp Ala Ile Lys Ala Leu His Ala Ser Gly Ile Gln Ala
    850                 855                 860

Ile Ala Asp Trp Val Pro Asp Gln Ile Tyr Asn Leu Pro Glu Gln Glu
865                 870                 875                 880

Leu Ala Thr Val Thr Arg Thr Asn Ser Phe Gly Asp Asp Asp Thr Asp
                885                 890                 895

Ser Asp Ile Asp Asn Ala Leu Tyr Val Val Gln Ser Arg Gly Gly Gly
            900                 905                 910

Gln Tyr Gln Glu Met Tyr Gly Gly Ala Phe Leu Glu Glu Leu Gln Ala
        915                 920                 925

Leu Tyr Pro Ser Leu Phe Lys Val Asn Gln Ile Ser Thr Gly Val Pro
    930                 935                 940

Ile Asp Gly Ser Val Lys Ile Thr Glu Trp Ala Ala Lys Tyr Phe Asn
945                 950                 955                 960

Gly Ser Asn Ile Gln Gly Lys Gly Ala Gly Tyr Val Leu Lys Asp Met
                965                 970                 975

Gly Ser Asn Lys Tyr Phe Lys Val Val Ser Asn Thr Glu Asp Gly Asp
            980                 985                 990

Tyr Leu Pro Lys Gln Leu Thr Asn  Asp Leu Ser Glu Thr  Gly Tyr Lys
        995                 1000                1005

Gly Glu  Leu Glu Gly Lys Pro  Ile Pro Asn Pro Leu  Leu Gly Leu
    1010                1015                1020

Asp Ser  Thr Arg Thr Gly His  His His His His His
    1025                1030                1035


<210> SEQ ID NO 10
<211> LENGTH: 1452
<212> TYPE: PRT
<213> ORGANISM: Artificial
<220> FEATURE:
<223> OTHER INFORMATION: Truncated dextrane saccharase

<400> SEQUENCE: 10

Met Gly Ser Asp Lys Ile Ile His Leu Thr Asp Asp Ser Phe Asp Thr
1               5                   10                  15

Asp Val Leu Lys Ala Asp Gly Ala Ile Leu Val Asp Phe Trp Ala His
```

-continued

```
                20                  25                  30

Trp Cys Gly Pro Cys Lys Met Ile Ala Pro Ile Leu Asp Glu Ile Ala
            35                  40                  45

Asp Glu Tyr Gln Gly Lys Leu Thr Val Ala Lys Leu Asn Ile Asp His
    50                  55                  60

Asn Pro Gly Thr Ala Pro Lys Tyr Gly Ile Arg Gly Ile Pro Thr Leu
65                  70                  75                  80

Leu Leu Phe Lys Asn Gly Glu Val Ala Ala Thr Lys Val Gly Ala Leu
                85                  90                  95

Ser Lys Gly Gln Leu Lys Glu Phe Leu Asp Ala Asn Leu Ala Gly Ser
            100                 105                 110

Gly Ser Gly Asp Asp Asp Asp Lys Leu Ala Leu Met Thr Gln Gln Val
        115                 120                 125

Ser Gly Lys Tyr Val Glu Lys Asp Gly Ser Trp Tyr Tyr Tyr Phe Asp
    130                 135                 140

Asp Gly Lys Asn Ala Lys Gly Leu Ser Thr Ile Asp Asn Asn Ile Gln
145                 150                 155                 160

Tyr Phe Tyr Glu Ser Gly Lys Gln Ala Lys Gly Gln Tyr Val Thr Ile
                165                 170                 175

Asp Asn Gln Thr Tyr Tyr Phe Asp Lys Gly Ser Gly Asp Glu Leu Thr
            180                 185                 190

Gly Leu Gln Ser Ile Asp Gly Asn Ile Val Ala Phe Asn Asp Glu Gly
        195                 200                 205

Gln Gln Ile Phe Asn Gln Tyr Tyr Gln Ser Glu Asn Gly Thr Thr Tyr
    210                 215                 220

Tyr Phe Asp Asp Lys Gly His Ala Ala Thr Gly Ile Lys Asn Ile Glu
225                 230                 235                 240

Gly Lys Asn Tyr Tyr Phe Asp Asn Leu Gly Gln Leu Lys Lys Gly Phe
                245                 250                 255

Ser Gly Val Ile Asp Gly Gln Ile Met Thr Phe Asp Gln Glu Thr Gly
            260                 265                 270

Gln Glu Val Ser Asn Thr Thr Ser Glu Ile Lys Glu Gly Leu Thr Thr
        275                 280                 285

Gln Asn Thr Asp Tyr Ser Glu His Asn Ala Ala His Gly Thr Asp Ala
    290                 295                 300

Glu Asp Phe Glu Asn Ile Asp Gly Tyr Leu Thr Ala Ser Ser Trp Tyr
305                 310                 315                 320

Arg Pro Thr Gly Ile Leu Arg Asn Gly Thr Asp Trp Glu Pro Ser Thr
                325                 330                 335

Asp Thr Asp Phe Arg Pro Ile Leu Ser Val Trp Trp Pro Asp Lys Asn
            340                 345                 350

Thr Gln Val Asn Tyr Leu Asn Tyr Met Ala Asp Leu Gly Phe Ile Ser
        355                 360                 365

Asn Ala Asp Ser Phe Glu Thr Gly Asp Ser Gln Ser Leu Leu Asn Glu
    370                 375                 380

Ala Ser Asn Tyr Val Gln Lys Ser Ile Glu Met Lys Ile Ser Ala Gln
385                 390                 395                 400

Gln Ser Thr Glu Trp Leu Lys Asp Ala Met Ala Ala Phe Ile Val Ala
                405                 410                 415

Gln Pro Gln Trp Asn Glu Thr Ser Glu Asp Met Ser Asn Asp His Leu
            420                 425                 430

Gln Asn Gly Ala Leu Thr Tyr Val Asn Ser Pro Leu Thr Pro Asp Ala
        435                 440                 445
```

-continued

```
Asn Ser Asn Phe Arg Leu Leu Asn Arg Thr Pro Thr Asn Gln Thr Gly
    450                 455                 460

Glu Gln Ala Tyr Asn Leu Asp Asn Ser Lys Gly Gly Phe Glu Leu Leu
465                 470                 475                 480

Leu Ala Asn Asp Val Asp Asn Ser Asn Pro Val Val Gln Ala Glu Gln
                485                 490                 495

Leu Asn Trp Leu Tyr Tyr Leu Met Asn Phe Gly Thr Ile Thr Ala Asn
            500                 505                 510

Asp Ala Asp Ala Asn Phe Asp Gly Ile Arg Val Asp Ala Val Asp Asn
        515                 520                 525

Val Asp Ala Asp Leu Leu Gln Ile Ala Ala Asp Tyr Phe Lys Leu Ala
    530                 535                 540

Tyr Gly Val Asp Gln Asn Asp Ala Thr Ala Asn Gln His Leu Ser Ile
545                 550                 555                 560

Leu Glu Asp Trp Ser His Asn Asp Pro Leu Tyr Val Thr Asp Gln Gly
                565                 570                 575

Ser Asn Gln Leu Thr Met Asp Asp Tyr Val His Thr Gln Leu Ile Trp
            580                 585                 590

Ser Leu Thr Lys Ser Ser Asp Ile Arg Gly Thr Met Gln Arg Phe Val
        595                 600                 605

Asp Tyr Tyr Met Val Asp Arg Ser Asn Asp Ser Thr Glu Asn Glu Ala
    610                 615                 620

Ile Pro Asn Tyr Ser Phe Val Arg Ala His Asp Tyr Asp Ala Gln Thr
625                 630                 635                 640

Val Ile Ala Gln Ile Val Ser Asp Leu Tyr Pro Asp Val Glu Asn Ser
                645                 650                 655

Leu Ala Pro Thr Thr Glu Gln Leu Ala Ala Ala Phe Lys Val Tyr Asn
            660                 665                 670

Glu Asp Glu Lys Leu Ala Asp Lys Lys Tyr Thr Gln Tyr Asn Met Ala
        675                 680                 685

Ser Ala Tyr Ala Met Leu Leu Thr Asn Lys Asp Thr Val Pro Arg Val
    690                 695                 700

Tyr Tyr Gly Asp Leu Tyr Thr Asp Asp Gly Gln Tyr Met Ala Thr Lys
705                 710                 715                 720

Ser Pro Tyr Tyr Asp Ala Ile Asn Thr Leu Leu Lys Ala Arg Val Gln
                725                 730                 735

Tyr Val Ala Gly Gly Gln Ser Met Ser Val Asp Ser Asn Asp Val Leu
            740                 745                 750

Thr Ser Val Arg Tyr Gly Lys Asp Ala Met Thr Ala Ser Asp Thr Gly
        755                 760                 765

Thr Ser Glu Thr Arg Thr Glu Gly Ile Gly Val Ile Val Ser Asn Asn
    770                 775                 780

Ala Glu Leu Gln Leu Glu Asp Gly His Thr Val Thr Leu His Met Gly
785                 790                 795                 800

Ala Ala His Lys Asn Gln Ala Tyr Arg Ala Leu Leu Ser Thr Thr Ala
                805                 810                 815

Asp Gly Leu Ala Tyr Tyr Asp Thr Asp Glu Asn Ala Pro Val Ala Tyr
            820                 825                 830

Thr Asp Ala Asn Gly Asp Leu Ile Phe Thr Asn Glu Ser Ile Tyr Gly
        835                 840                 845

Val Gln Asn Pro Gln Val Ser Gly Tyr Leu Ala Val Trp Val Pro Val
    850                 855                 860
```

-continued

```
Gly Ala Gln Gln Asp Gln Asp Ala Arg Thr Ala Ser Asp Thr Thr Thr
865                 870                 875                 880

Asn Thr Ser Asp Lys Val Phe His Ser Asn Ala Ala Leu Asp Ser Gln
                885                 890                 895

Val Ile Tyr Glu Gly Phe Ser Asn Phe Gln Ala Phe Ala Thr Asp Ser
            900                 905                 910

Ser Glu Tyr Thr Asn Val Val Ile Ala Gln Asn Ala Asp Gln Phe Lys
        915                 920                 925

Gln Trp Gly Val Thr Ser Phe Gln Leu Ala Pro Gln Tyr Arg Ser Ser
    930                 935                 940

Thr Asp Thr Ser Phe Leu Asp Ser Ile Ile Gln Asn Gly Tyr Ala Phe
945                 950                 955                 960

Thr Asp Arg Tyr Asp Leu Gly Tyr Gly Thr Pro Thr Lys Tyr Gly Thr
                965                 970                 975

Ala Asp Gln Leu Arg Asp Ala Ile Lys Ala Leu His Ala Ser Gly Ile
            980                 985                 990

Gln Ala Ile Ala Asp Trp Val Pro  Asp Gln Ile Tyr Asn  Leu Pro Glu
        995                 1000                1005

Gln Glu  Leu Ala Thr Val Thr  Arg Thr Asn Ser Phe  Gly Asp Asp
    1010                 1015                 1020

Asp Thr  Asp Ser Asp Ile Asp  Asn Ala Leu Tyr Val  Val Gln Ser
    1025                 1030                 1035

Arg Gly  Gly Gly Gln Tyr Gln  Glu Met Tyr Gly Gly  Ala Phe Leu
    1040                 1045                 1050

Glu Glu  Leu Gln Ala Leu Tyr  Pro Ser Leu Phe Lys  Val Asn Gln
    1055                 1060                 1065

Ile Ser  Thr Gly Val Pro Ile  Asp Gly Ser Val Lys  Ile Thr Glu
    1070                 1075                 1080

Trp Ala  Ala Lys Tyr Phe Asn  Gly Ser Asn Ile Gln  Gly Lys Gly
    1085                 1090                 1095

Ala Gly  Tyr Val Leu Lys Asp  Met Gly Ser Asn Lys  Tyr Phe Lys
    1100                 1105                 1110

Val Val  Ser Asn Thr Glu Asp  Gly Asp Tyr Leu Pro  Lys Gln Leu
    1115                 1120                 1125

Thr Asn  Asp Leu Ser Glu Thr  Gly Phe Thr His Asp  Asp Lys Gly
    1130                 1135                 1140

Ile Ile  Tyr Tyr Thr Leu Ser  Gly Tyr Arg Ala Gln  Asn Ala Phe
    1145                 1150                 1155

Ile Gln  Asp Asp Asp Asn Asn  Tyr Tyr Tyr Phe Asp  Lys Thr Gly
    1160                 1165                 1170

His Leu  Val Thr Gly Leu Gln  Lys Ile Asn Asn His  Thr Tyr Phe
    1175                 1180                 1185

Phe Leu  Pro Asn Gly Ile Glu  Leu Val Lys Ser Phe  Leu Gln Asn
    1190                 1195                 1200

Glu Asp  Gly Thr Ile Val Tyr  Phe Asp Lys Lys Gly  His Gln Val
    1205                 1210                 1215

Phe Asp  Gln Tyr Ile Thr Asp  Gln Asn Gly Asn Ala  Tyr Tyr Phe
    1220                 1225                 1230

Asp Asp  Ala Gly Val Met Leu  Lys Ser Gly Leu Ala  Thr Ile Asp
    1235                 1240                 1245

Gly His  Gln Gln Tyr Phe Asp  Gln Asn Gly Val Gln  Val Lys Asp
    1250                 1255                 1260

Lys Phe  Val Ile Gly Thr Asp  Gly Tyr Lys Tyr Tyr  Phe Glu Pro
```

-continued

```
    1265                1270                1275

Gly Ser  Gly Asn Leu Ala Ile  Leu Arg Tyr Val Gln  Asn Ser Lys
    1280                1285                1290

Asn Gln  Trp Phe Tyr Phe Asp  Gly Asn Gly His Ala  Val Thr Gly
    1295                1300                1305

Phe Gln  Thr Ile Asn Gly Lys  Lys Gln Tyr Phe Tyr  Asn Asp Gly
    1310                1315                1320

His Gln  Ser Lys Gly Glu Phe  Ile Asp Ala Asp Gly  Asp Thr Phe
    1325                1330                1335

Tyr Thr  Ser Ala Thr Asp Gly  Arg Leu Val Thr Gly  Val Gln Lys
    1340                1345                1350

Ile Asn  Gly Ile Thr Tyr Ala  Phe Asp Asn Thr Gly  Asn Leu Ile
    1355                1360                1365

Thr Asn  Gln Tyr Tyr Gln Leu  Ala Asp Gly Lys Tyr  Met Leu Leu
    1370                1375                1380

Asp Asp  Ser Gly Arg Ala Lys  Thr Gly Phe Val Leu  Gln Asp Gly
    1385                1390                1395

Val Leu  Arg Tyr Phe Asp Gln  Asn Gly Glu Gln Val  Lys Asp Ala
    1400                1405                1410

Ile Ile  Val Asp Pro Asp Thr  Asn Leu Ser Tyr Lys  Gly Glu Leu
    1415                1420                1425

Glu Gly  Lys Pro Ile Pro Asn  Pro Leu Leu Gly Leu  Asp Ser Thr
    1430                1435                1440

Arg Thr  Gly His His His His  His His
    1445                1450
```

<210> SEQ ID NO 11
<211> LENGTH: 18
<212> TYPE: DNA
<213> ORGANISM: Artificial
<220> FEATURE:
<223> OTHER INFORMATION: Primer

<400> SEQUENCE: 11
ggcttctctg gtgtgatt 18

<210> SEQ ID NO 12
<211> LENGTH: 18
<212> TYPE: DNA
<213> ORGANISM: Artificial
<220> FEATURE:
<223> OTHER INFORMATION: Primer

<400> SEQUENCE: 12
gatctgtcag aaactggc 18

<210> SEQ ID NO 13
<211> LENGTH: 18
<212> TYPE: DNA
<213> ORGANISM: Artificial
<220> FEATURE:
<223> OTHER INFORMATION: Primer

<400> SEQUENCE: 13
acacaacaag ttagcggc 18

<210> SEQ ID NO 14
<211> LENGTH: 18
<212> TYPE: DNA
<213> ORGANISM: Artificial

-continued

<220> FEATURE:
<223> OTHER INFORMATION: Primer

<400> SEQUENCE: 14
ccagatacta acttgagt 18

<210> SEQ ID NO 15
<211> LENGTH: 18
<212> TYPE: DNA
<213> ORGANISM: Artificial
<220> FEATURE:
<223> OTHER INFORMATION: Primer

<400> SEQUENCE: 15
ttcattgatg cagacggg 18

<210> SEQ ID NO 16
<211> LENGTH: 18
<212> TYPE: DNA
<213> ORGANISM: Artificial
<220> FEATURE:
<223> OTHER INFORMATION: Primer

<400> SEQUENCE: 16
cacgactacg acgcgcaa 18

<210> SEQ ID NO 17
<211> LENGTH: 3897
<212> TYPE: DNA
<213> ORGANISM: Artificial
<220> FEATURE:
<223> OTHER INFORMATION: Truncated dextrane saccharase

<400> SEQUENCE: 17
acacaacaag ttagcggcaa gtacgttgaa aaagacggta gttggtatta ttattttgat 60
gatggcaaaa atgctaaagg tttatcaacg atagacaaca atattcaata tttttacgag 120
agtggtaaac aagccaaagg acagtatgtc acaattgata atcaaacata ttattttgat 180
aagggctcag gtgatgagtt aactggtctg caaagcattg atgggaacat agttgctttt 240
aacgatgaag ggcaacaaat ttttaatcaa tattaccaat ctgaaaatgg tacaacatac 300
tactttgatg ataaaggaca cgctgctacc ggtattaaga atatcgaggg caaaaattat 360
tattttgata atcttgggca actaaaaaaa ggcttctctg gtgtgattga tggtcaaata 420
atgacatttg atcaggaaac agggcaagaa gtttctaaca caacttctga aataaaagaa 480
ggtttgacga ctcaaaacac ggattatagc gaacataatg cagcccacgg tacggatgct 540
gaggactttg aaaatattga cggctattta acagctagtt catggtatcg tccaacaggt 600
attttacgta acggaacaga ctgggaacct tctacagata cagatttcag accaatattg 660
tcagtgtggt ggccagataa gaacacccag gtcaattatt taaattacat ggctgattta 720
gggtttatca gtaatgcgga cagttttgaa actggggata gccaaagctt attaaatgaa 780
gcaagtaact atgttcaaaa atcaattgaa atgaaaatta gtgcgcaaca aagtacagag 840
tggttaaagg atgcaatggc ggccttcatt gtcgcgcaac cacagtggaa tgaaactagt 900
gaagatatga gcaatgacca tttacaaaat ggcgcattaa cttatgtcaa cagtccactg 960
acacctgacg ctaattcaaa ctttagacta cttaatcgga caccaacaaa ccagactggt 1020
gaacaagcgt ataatttaga taattcaaaa ggtggttttg aattgttgtt agccaatgac 1080
gttgataatt caaaccctgt agtacaagca gaacaattga attggttata ttatttaatg 1140

-continued

```
aattttggta cgattacggc caacgacgcg gatgctaatt ttgatggtat tcgtgtagat   1200
gcagtcgaca atgtggatgc tgatttgtta caaattgctg ccgattattt caaactagct   1260
tacggtgttg atcaaaatga tgctactgct aatcagcatc tttcaatttt ggaagattgg   1320
agtcacaatg atcctttgta tgtaacagat caaggaagca atcaattaac catggatgat   1380
tatgtgcaca cacaattaat ctggtctcta acaaaatcat ctgacatacg aggtacaatg   1440
cagcgcttcg tggattatta tatggtggat cgatctaatg atagtacaga aaacgaagcc   1500
attcctaatt acagctttgt acgtgcacac gacagcgaag tgcaaacggt tattgcccaa   1560
attgtttccg atttgtatcc tgatgttgaa aatagtttag caccaacaac agaacaattg   1620
gcagctgctt tcaaagtata caatgaagat gaaaaattag cagacaaaaa gtacacacaa   1680
tataatatgg ctagtgctta tgcgatgttg ctaaccaata aggatactgt tcctcgtgtc   1740
tattatggcg atttatatac agatgatggt caatatatgg caacaaagtc accatactat   1800
gatgcgatta acactttgct aaaggctaga gttcagtatg ttgctggtgg ccaatcgatg   1860
tccgttgata gtaatgacgt gttaacaagt gttcgctatg gtaaagatgc catgacagct   1920
tctgacactg gaacatctga gacgcgtact gaaggtattg gagtcatcgt cagcaataac   1980
gcggagctac aattagagga tgggcatact gtcacattgc atatgggggc agctcataag   2040
aaccaagctt atcgtgcttt gttatcaaca actgcagatg gattagctta ttatgatact   2100
gatgaaaatg cacctgtggc gtacacagat gctaacggcg atttgatttt tacgaatgaa   2160
tcaatttatg gtgtacaaaa tccacaagtt tctggttact tggcagtttg ggttccggta   2220
ggtgcgcaac aagatcaaga tgcacgaacg gcctctgata caacaacaaa cacgagtgat   2280
aaagtgttcc attcaaacgc tgctcttgat tctcaagtca tctacgaagg tttctcaaac   2340
ttccaagcat ttgctacaga cagcagtgaa tatacaaacg tagtcatcgc tcagaatgcg   2400
gaccaattta agcaatgggg tgtgacaagc ttccaattgg caccacaata tcgttcaagt   2460
acagatacaa gtttcttgga ttcaattatt caaaacgggt atgcattcac ggatcgttat   2520
gacttaggtt atggcacacc gacaaaatat ggaactgctg atcagttgcg cgatgctatt   2580
aaagccttac atgctagcgg tattcaagcc attgccgatt gggtgccgga ccaaatttat   2640
aatttgccag agcaagaatt agctactgtc acaagaacaa attcatttgg agatgacgat   2700
acagattctg atattgacaa tgccttatat gttgtacaaa gtcgtggggg tggtcaatat   2760
caagagatgt atggtggtgc cttcttagaa gagttacagg cactctatcc atccctattt   2820
aaagtgaatc aaatctcaac tggcgttcca attgatggca gtgtaaagat tactgagtgg   2880
gcggctaagt acttcaatgg ctctaacatc caaggtaaag gtgctggata cgtattgaaa   2940
gatatgggtt ctaataagta ctttaaggtc gtttcgaaca ctgaggatgg tgactactta   3000
ccaaaacagt taactaatga tctgtcagaa actggcttta cacacgatga taaaggaatc   3060
atctattata cattaagtgg ttatcgtgcc caaaatgcat ttattcaaga tgatgataat   3120
aactattact attttgataa aacaggtcat ttagtaacag gtttgcaaaa gattaataac   3180
catacctact tcttcttacc taatggtatc gaactggtca agagcttctt acaaaacgaa   3240
gatggtacaa ttgtttattt cgataagaaa ggtcatcaag tttttgatca atatataact   3300
gatcaaaatg gaaatgcgta ttactttgat gatgctggtg taatgcttaa atcagggctt   3360
gcaacgattg atggacatca acagtatttt gatcaaaatg gtgtgcaggt taaggataag   3420
tttgtgattg gcactgatgg ttataagtat tactttgaac caggtagtgg taacttagct   3480
atcctacgtt atgtgcaaaa tagtaagaat caatggttct attttgatgg taatggccat   3540
```

-continued

```
gctgtcactg gtttccaaac aattaatggt aaaaaacaat atttctataa tgatggtcat   3600

caaagtaaag gtgaattcat tgatgcagac ggggatactt tctatacgag tgccactgat   3660

ggtcgcctag taactggtgt tcagaagatt aatggtatta cctatgcttt tgataacaca   3720

ggaaatttga tcacaaatca gtattatcaa ttagcagatg gtaaatatat gttgttagat   3780

gatagtggtc gtgcgaaaac agggtttgta ttgcaagatg gtgtactaag atacttcgat   3840

caaaacggtg agcaagtgaa agatgctatc attgtggatc cagatactaa cttgagt      3897
```

```
<210> SEQ ID NO 18
<211> LENGTH: 3633
<212> TYPE: DNA
<213> ORGANISM: Artificial
<220> FEATURE:
<223> OTHER INFORMATION: Truncated dextrane saccharase

<400> SEQUENCE: 18

acacaacaag ttagcggcaa gtacgttgaa aaagacggta gttggtatta ttattttgat     60

gatggcaaaa atgctaaagg tttatcaacg atagacaaca atattcaata tttttacgag    120

agtggtaaac aagccaaagg acagtatgtc acaattgata atcaaacata ttattttgat    180

aagggctcag gtgatgagtt aactggtctg caaagcattg atgggaacat agttgctttt    240

aacgatgaag ggcaacaaat ttttaatcaa tattaccaat ctgaaaatgg tacaacatac    300

tactttgatg ataaaggaca cgctgctacc ggtattaaga atatcgaggg caaaaattat    360

tattttgata atcttgggca actaaaaaaa ggcttctctg gtgtgattga tggtcaaata    420

atgacatttg atcaggaaac agggcaagaa gtttctaaca caacttctga aataaaagaa    480

ggtttgacga ctcaaaacac ggattatagc gaacataatg cagcccacgg tacggatgct    540

gaggactttg aaaatattga cggctattta acagctagtt catggtatcg tccaacaggt    600

attttacgta acggaacaga ctgggaacct tctacagata cagatttcag accaatattg    660

tcagtgtggt ggccagataa gaacacccag gtcaattatt taaattacat ggctgattta    720

gggtttatca gtaatgcgga cagttttgaa actggggata gccaaagctt attaaatgaa    780

gcaagtaact atgttcaaaa atcaattgaa atgaaaatta gtgcgcaaca aagtacagag    840

tggttaaagg atgcaatggc ggccttcatt gtcgcgcaac cacagtggaa tgaaactagt    900

gaagatatga gcaatgacca tttacaaaat ggcgcattaa cttatgtcaa cagtccactg    960

acacctgacg ctaattcaaa ctttagacta cttaatcgga caccaacaaa ccagactggt   1020

gaacaagcgt ataatttaga taattcaaaa ggtggttttg aattgttgtt agccaatgac   1080

gttgataatt caaaccctgt agtacaagca gaacaattga attggttata ttatttaatg   1140

aattttggta cgattacggc caacgacgcg gatgctaatt ttgatggtat tcgtgtagat   1200

gcagtcgaca atgtggatgc tgatttgtta caaattgctg ccgattattt caaactagct   1260

tacggtgttg atcaaaatga tgctactgct aatcagcatc tttcaatttt ggaagattgg   1320

agtcacaatg atcctttgta tgtaacagat caaggaagca atcaattaac catggatgat   1380

tatgtgcaca cacaattaat ctggtctcta acaaaatcat ctgacatacg aggtacaatg   1440

cagcgcttcg tggattatta tatggtggat cgatctaatg atagtacaga aaacgaagcc   1500

attcctaatt acagctttgt acgtgcacac gacagcgaag tgcaaacggt tattgcccaa   1560

attgtttccg atttgtatcc tgatgttgaa aatagtttag caccaacaac agaacaattg   1620

gcagctgctt tcaaagtata caatgaagat gaaaaattag cagacaaaaa gtacacacaa   1680
```

-continued

```
tataatatgg ctagtgctta tgcgatgttg ctaaccaata aggatactgt tcctcgtgtc   1740

tattatggcg atttatatac agatgatggt caatatatgg caacaaagtc accatactat   1800

gatgcgatta acactttgct aaaggctaga gttcagtatg ttgctggtgg ccaatcgatg   1860

tccgttgata gtaatgacgt gttaacaagt gttcgctatg gtaaagatgc catgacagct   1920

tctgacactg gaacatctga gacgcgtact gaaggtattg gagtcatcgt cagcaataac   1980

gcggagctac aattagagga tgggcatact gtcacattgc atatgggggc agctcataag   2040

aaccaagctt atcgtgcttt gttatcaaca actgcagatg gattagctta ttatgatact   2100

gatgaaaatg cacctgtggc gtacacagat gctaacggcg atttgatttt tacgaatgaa   2160

tcaatttatg gtgtacaaaa tccacaagtt tctggttact tggcagtttg ggttccggta   2220

ggtgcgcaac aagatcaaga tgcacgaacg gcctctgata caacaacaaa cacgagtgat   2280

aaagtgttcc attcaaacgc tgctcttgat tctcaagtca tctacgaagg tttctcaaac   2340

ttccaagcat ttgctacaga cagcagtgaa tatacaaacg tagtcatcgc tcagaatgcg   2400

gaccaattta agcaatgggg tgtgacaagc ttccaattgg caccacaata tcgttcaagt   2460

acagatacaa gtttcttgga ttcaattatt caaaacgggt atgcattcac ggatcgttat   2520

gacttaggtt atggcacacc gacaaaatat ggaactgctg atcagttgcg cgatgctatt   2580

aaagccttac atgctagcgg tattcaagcc attgccgatt gggtgccgga ccaaatttat   2640

aatttgccag agcaagaatt agctactgtc acaagaacaa attcatttgg agatgacgat   2700

acagattctg atattgacaa tgccttatat gttgtacaaa gtcgtggggg tggtcaatat   2760

caagagatgt atggtggtgc cttcttagaa gagttacagg cactctatcc atccctattt   2820

aaagtgaatc aaatctcaac tggcgttcca attgatggca gtgtaaagat tactgagtgg   2880

gcggctaagt acttcaatgg ctctaacatc caaggtaaag gtgctggata cgtattgaaa   2940

gatatgggtt ctaataagta ctttaaggtc gtttcgaaca ctgaggatgg tgactactta   3000

ccaaaacagt taactaatga tctgtcagaa actggcttta cacacgatga taaaggaatc   3060

atctattata cattaagtgg ttatcgtgcc caaaatgcat ttattcaaga tgatgataat   3120

aactattact attttgataa aacaggtcat ttagtaacag gtttgcaaaa gattaataac   3180

catacctact tcttcttacc taatggtatc gaactggtca agagcttctt acaaaacgaa   3240

gatggtacaa ttgtttattt cgataagaaa ggtcatcaag tttttgatca atatataact   3300

gatcaaaatg gaaatgcgta ttactttgat gatgctggtg taatgcttaa atcagggctt   3360

gcaacgattg atggacatca acagtatttt gatcaaaatg gtgtgcaggt taaggataag   3420

tttgtgattg gcactgatgg ttataagtat tactttgaac caggtagtgg taacttagct   3480

atcctacgtt atgtgcaaaa tagtaagaat caatggttct attttgatgg taatggccat   3540

gctgtcactg gtttccaaac aattaatggt aaaaaacaat atttctataa tgatggtcat   3600

caaagtaaag gtgaattcat tgatgcagac ggg                                 3633
```

<210> SEQ ID NO 19
<211> LENGTH: 3036
<212> TYPE: DNA
<213> ORGANISM: Artificial
<220> FEATURE:
<223> OTHER INFORMATION: Truncated dextrane saccharase

<400> SEQUENCE: 19

```
acacaacaag ttagcggcaa gtacgttgaa aaagacggta gttggtatta ttattttgat     60

gatggcaaaa atgctaaagg tttatcaacg atagacaaca atattcaata tttttacgag    120
```

-continued

```
agtggtaaac aagccaaagg acagtatgtc acaattgata atcaaacata ttattttgat    180
aagggctcag gtgatgagtt aactggtctg caaagcattg atgggaacat agttgctttt    240
aacgatgaag ggcaacaaat ttttaatcaa tattaccaat ctgaaaatgg tacaacatac    300
tactttgatg ataaaggaca cgctgctacc ggtattaaga atatcgaggg caaaaattat    360
tattttgata atcttgggca actaaaaaaa ggcttctctg gtgtgattga tggtcaaata    420
atgacatttg atcaggaaac agggcaagaa gtttctaaca caacttctga aataaaagaa    480
ggtttgacga ctcaaaacac ggattatagc gaacataatg cagcccacgg tacggatgct    540
gaggactttg aaaatattga cggctattta acagctagtt catggtatcg tccaacaggt    600
attttacgta acggaacaga ctgggaacct tctacagata cagatttcag accaatattg    660
tcagtgtggt ggccagataa gaacacccag gtcaattatt taaattacat ggctgattta    720
gggtttatca gtaatgcgga cagttttgaa actggggata gccaaagctt attaaatgaa    780
gcaagtaact atgttcaaaa atcaattgaa atgaaaatta gtgcgcaaca aagtacagag    840
tggttaaagg atgcaatggc ggccttcatt gtcgcgcaac cacagtggaa tgaaactagt    900
gaagatatga gcaatgacca tttacaaaat ggcgcattaa cttatgtcaa cagtccactg    960
acacctgacg ctaattcaaa ctttagacta cttaatcgga caccaacaaa ccagactggt   1020
gaacaagcgt ataatttaga taattcaaaa ggtggttttg aattgttgtt agccaatgac   1080
gttgataatt caaaccctgt agtacaagca gaacaattga attggttata ttatttaatg   1140
aattttggta cgattacggc caacgacgcg gatgctaatt ttgatggtat tcgtgtagat   1200
gcagtcgaca atgtggatgc tgatttgtta caaattgctg ccgattattt caaactagct   1260
tacggtgttg atcaaaatga tgctactgct aatcagcatc tttcaatttt ggaagattgg   1320
agtcacaatg atcctttgta tgtaacagat caaggaagca atcaattaac catggatgat   1380
tatgtgcaca cacaattaat ctggtctcta acaaaatcat ctgacatacg aggtacaatg   1440
cagcgcttcg tggattatta tatggtggat cgatctaatg atagtacaga aaacgaagcc   1500
attcctaatt acagctttgt acgtgcacac gacagcgaag tgcaaacggt tattgcccaa   1560
attgtttccg atttgtatcc tgatgttgaa aatagtttag caccaacaac agaacaattg   1620
gcagctgctt tcaaagtata caatgaagat gaaaaattag cagacaaaaa gtacacacaa   1680
tataatatgg ctagtgctta tgcgatgttg ctaaccaata aggatactgt tcctcgtgtc   1740
tattatggcg atttatatac agatgatggt caatatatgg caacaaagtc accatactat   1800
gatgcgatta acactttgct aaaggctaga gttcagtatg ttgctggtgg ccaatcgatg   1860
tccgttgata gtaatgacgt gttaacaagt gttcgctatg gtaaagatgc catgacagct   1920
tctgacactg gaacatctga gacgcgtact gaaggtattg gagtcatcgt cagcaataac   1980
gcggagctac aattagagga tgggcatact gtcacattgc atatgggggc agctcataag   2040
aaccaagctt atcgtgcttt gttatcaaca actgcagatg gattagctta ttatgatact   2100
gatgaaaatg cacctgtggc gtacacagat gctaacggcg atttgatttt tacgaatgaa   2160
tcaatttatg gtgtacaaaa tccacaagtt tctggttact tggcagtttg ggttccggta   2220
ggtgcgcaac aagatcaaga tgcacgaacg gcctctgata caacaacaaa cacgagtgat   2280
aaagtgttcc attcaaacgc tgctcttgat tctcaagtca tctacgaagg tttctcaaac   2340
ttccaagcat ttgctacaga cagcagtgaa tatacaaacg tagtcatcgc tcagaatgcg   2400
gaccaattta agcaatgggg tgtgacaagc ttccaattgg caccacaata tcgttcaagt   2460
```

-continued

```
acagatacaa gtttcttgga ttcaattatt caaaacgggt atgcattcac ggatcgttat   2520

gacttaggtt atggcacacc gacaaaatat ggaactgctg atcagttgcg cgatgctatt   2580

aaagccttac atgctagcgg tattcaagcc attgccgatt gggtgccgga ccaaatttat   2640

aatttgccag agcaagaatt agctactgtc acaagaacaa attcatttgg agatgacgat   2700

acagattctg atattgacaa tgccttatat gttgtacaaa gtcgtggggg tggtcaatat   2760

caagagatgt atggtggtgc cttcttagaa gagttacagg cactctatcc atccctattt   2820

aaagtgaatc aaatctcaac tggcgttcca attgatggca gtgtaaagat tactgagtgg   2880

gcggctaagt acttcaatgg ctctaacatc caaggtaaag gtgctggata cgtattgaaa   2940

gatatgggtt ctaataagta ctttaaggtc gtttcgaaca ctgaggatgg tgactactta   3000

ccaaaacagt taactaatga tctgtcagaa actggc                             3036


<210> SEQ ID NO 20
<211> LENGTH: 2646
<212> TYPE: DNA
<213> ORGANISM: Artificial
<220> FEATURE:
<223> OTHER INFORMATION: Truncated dextrane saccharase

<400> SEQUENCE: 20

ggcttctctg gtgtgattga tggtcaaata atgacatttg atcaggaaac agggcaagaa     60

gtttctaaca caacttctga aataaaagaa ggtttgacga ctcaaaacac ggattatagc    120

gaacataatg cagcccacgg tacggatgct gaggactttg aaaatattga cggctattta    180

acagctagtt catggtatcg tccaacaggt attttacgta acggaacaga ctgggaacct    240

tctacagata cagatttcag accaatattg tcagtgtggt ggccagataa gaacacccag    300

gtcaattatt taaattacat ggctgattta gggtttatca gtaatgcgga cagttttgaa    360

actggggata gccaaagctt attaaatgaa gcaagtaact atgttcaaaa atcaattgaa    420

atgaaaatta gtgcgcaaca aagtacagag tggttaaagg atgcaatggc ggccttcatt    480

gtcgcgcaac cacagtggaa tgaaactagt gaagatatga gcaatgacca tttacaaaat    540

ggcgcattaa cttatgtcaa cagtccactg acacctgacg ctaattcaaa ctttagacta    600

cttaatcgga caccaacaaa ccagactggt gaacaagcgt ataatttaga taattcaaaa    660

ggtggttttg aattgttgtt agccaatgac gttgataatt caaaccctgt agtacaagca    720

gaacaattga attggttata ttatttaatg aattttggta cgattacggc caacgacgcg    780

gatgctaatt ttgatggtat tcgtgtagat gcagtcgaca atgtggatgc tgatttgtta    840

caaattgctg ccgattattt caaactagct tacggtgttg atcaaaatga tgctactgct    900

aatcagcatc tttcaatttt ggaagattgg agtcacaatg atcctttgta tgtaacagat    960

caaggaagca atcaattaac catggatgat tatgtgcaca cacaattaat ctggtctcta   1020

acaaaatcat ctgacatacg aggtacaatg cagcgcttcg tggattatta tatggtggat   1080

cgatctaatg atagtacaga aaacgaagcc attcctaatt acagctttgt acgtgcacac   1140

gacagcgaag tgcaaacggt tattgcccaa attgtttccg atttgtatcc tgatgttgaa   1200

aatagtttag caccaacaac agaacaattg gcagctgctt tcaaagtata caatgaagat   1260

gaaaaattag cagacaaaaa gtacacacaa tataatatgg ctagtgctta tgcgatgttg   1320

ctaaccaata aggatactgt tcctcgtgtc tattatggcg atttatatac agatgatggt   1380

caatatatgg caacaaagtc accatactat gatgcgatta acactttgct aaaggctaga   1440

gttcagtatg ttgctggtgg ccaatcgatg tccgttgata gtaatgacgt gttaacaagt   1500
```

-continued gttcgctatg gtaaagatgc catgacagct tctgacactg gaacatctga gacgcgtact 1560
gaaggtattg gagtcatcgt cagcaataac gcggagctac aattagagga tgggcatact 1620
gtcacattgc atatgggggc agctcataag aaccaagctt atcgtgcttt gttatcaaca 1680
actgcagatg gattagctta ttatgatact gatgaaaatg cacctgtggc gtacacagat 1740
gctaacggcg atttgatttt tacgaatgaa tcaatttatg gtgtacaaaa tccacaagtt 1800
tctggttact tggcagtttg ggttccggta ggtgcgcaac aagatcaaga tgcacgaacg 1860
gcctctgata caacaacaaa cacgagtgat aaagtgttcc attcaaacgc tgctcttgat 1920
tctcaagtca tctacgaagg tttctcaaac ttccaagcat ttgctacaga cagcagtgaa 1980
tatacaaacg tagtcatcgc tcagaatgcg gaccaattta agcaatgggg tgtgacaagc 2040
ttccaattgg caccacaata tcgttcaagt acagatacaa gtttcttgga ttcaattatt 2100
caaaacgggt atgcattcac ggatcgttat gacttaggtt atggcacacc gacaaaatat 2160
ggaactgctg atcagttgcg cgatgctatt aaagccttac atgctagcgg tattcaagcc 2220
attgccgatt gggtgccgga ccaaatttat aatttgccag agcaagaatt agctactgtc 2280
acaagaacaa attcatttgg agatgacgat acagattctg atattgacaa tgccttatat 2340
gttgtacaaa gtcgtggggg tggtcaatat caagagatgt atggtggtgc cttcttagaa 2400
gagttacagg cactctatcc atccctattt aaagtgaatc aaatctcaac tggcgttcca 2460
attgatggca gtgtaaagat tactgagtgg gcggctaagt acttcaatgg ctctaacatc 2520
caaggtaaag gtgctggata cgtattgaaa gatatgggtt ctaataagta ctttaaggtc 2580
gtttcgaaca ctgaggatgg tgactactta ccaaaacagt taactaatga tctgtcagaa 2640
actggc 2646

<210> SEQ ID NO 21
<211> LENGTH: 3897
<212> TYPE: DNA
<213> ORGANISM: Artificial
<220> FEATURE:
<223> OTHER INFORMATION: Mutated / truncated

<400> SEQUENCE: 21
acacaacaag ttagcggcaa gtacgttgaa aaagacggta gttggtatta ttattttgat 60
gatggcaaaa atgctaaagg tttatcaacg atagacaaca atattcaata tttttacgag 120
agtggtaaac aagccaaagg acagtatgtc acaattgata atcaaacata ttattttgat 180
aagggctcag gtgatgagtt aactggtctg caaagcattg atgggaacat agttgctttt 240
aacgatgaag ggcaacaaat ttttaatcaa tattaccaat ctgaaaatgg tacaacatac 300
tactttgatg ataaaggaca cgctgctacc ggtattaaga atatcgaggg caaaaattat 360
tattttgata atcttgggca actaaaaaaa ggcttctctg gtgtgattga tggtcaaata 420
atgacatttg atcaggaaac agggcaagaa gtttctaaca caacttctga aataaaagaa 480
ggtttgacga ctcaaaacac ggattatagc gaacataatg cagcccacgg tacggatgct 540
gaggactttg aaaatattga cggctattta acagctagtt catggtatcg tccaacaggt 600
attttacgta acggaacaga ctgggaacct tctacagata cagatttcag accaatattg 660
tcagtgtggt ggccagataa gaacacccag gtcaattatt taaattacat ggctgattta 720
gggtttatca gtaatgcgga cagttttgaa actggggata gccaaagctt attaaatgaa 780
gcaagtaact atgttcaaaa atcaattgaa atgaaaatta gtgcgcaaca aagtacagag 840

-continued

```
tggttaaagg atgcaatggc ggccttcatt gtcgcgcaac cacagtggaa tgaaactagt    900

gaagatatga gcaatgacca tttacaaaat ggcgcattaa cttatgtcaa cagtccactg    960

acacctgacg ctaattcaaa ctttagacta cttaatcgga caccaacaaa ccagactggt   1020

gaacaagcgt ataatttaga taattcaaaa ggtggttttg aattgttgtt agccaatgac   1080

gttgataatt caaaccctgt agtacaagca gaacaattga attggttata ttatttaatg   1140

aattttggta cgattacggc caacgacgcg gatgctaatt ttgatggtat tcgtgtagat   1200

gcagtcgaca atgtggatgc tgatttgtta caaattgctg ccgattattt caaactagct   1260

tacggtgttg atcaaaatga tgctactgct aatcagcatc tttcaatttt ggaagattgg   1320

agtcacaatg atcctttgta tgtaacagat caaggaagca atcaattaac catggatgat   1380

tatgtgcaca cacaattaat ctggtctcta acaaaatcat ctgacatacg aggtacaatg   1440

cagcgcttcg tggattatta tatggtggat cgatctaatg atagtacaga aaacgaagcc   1500

attcctaatt acagctttgt acgagctcac gactacgacg cgcaaacggt tattgcccaa   1560

attgtttccg atttgtatcc tgatgttgaa aatagtttag caccaacaac agaacaattg   1620

gcagctgctt tcaaagtata caatgaagat gaaaaattag cagacaaaaa gtacacacaa   1680

tataatatgg ctagtgctta tgcgatgttg ctaaccaata aggatactgt tcctcgtgtc   1740

tattatggcg atttatatac agatgatggt caatatatgg caacaaagtc accatactat   1800

gatgcgatta acactttgct aaaggctaga gttcagtatg ttgctggtgg ccaatcgatg   1860

tccgttgata gtaatgacgt gttaacaagt gttcgctatg gtaaagatgc catgacagct   1920

tctgacactg gaacatctga gacgcgtact gaaggtattg gagtcatcgt cagcaataac   1980

gcggagctac aattagagga tgggcatact gtcacattgc atatgggggc agctcataag   2040

aaccaagctt atcgtgcttt gttatcaaca actgcagatg gattagctta ttatgatact   2100

gatgaaaatg cacctgtggc gtacacagat gctaacggcg atttgatttt tacgaatgaa   2160

tcaatttatg gtgtacaaaa tccacaagtt tctggttact tggcagtttg ggttccggta   2220

ggtgcgcaac aagatcaaga tgcacgaacg gcctctgata caacaacaaa cacgagtgat   2280

aaagtgttcc attcaaacgc tgctcttgat tctcaagtca tctacgaagg tttctcaaac   2340

ttccaagcat ttgctacaga cagcagtgaa tatacaaacg tagtcatcgc tcagaatgcg   2400

gaccaattta agcaatgggg tgtgacaagc ttccaattgg caccacaata tcgttcaagt   2460

acagatacaa gtttcttgga ttcaattatt caaaacgggt atgcattcac ggatcgttat   2520

gacttaggtt atggcacacc gacaaaatat ggaactgctg atcagttgcg cgatgctatt   2580

aaagccttac atgctagcgg tattcaagcc attgccgatt gggtgccgga ccaaatttat   2640

aatttgccag agcaagaatt agctactgtc acaagaacaa attcatttgg agatgacgat   2700

acagattctg atattgacaa tgccttatat gttgtacaaa gtcgtggggg tggtcaatat   2760

caagagatgt atggtggtgc cttcttagaa gagttacagg cactctatcc atccctattt   2820

aaagtgaatc aaatctcaac tggcgttcca attgatggca gtgtaaagat tactgagtgg   2880

gcggctaagt acttcaatgg ctctaacatc caaggtaaag gtgctggata cgtattgaaa   2940

gatatgggtt ctaataagta ctttaaggtc gtttcgaaca ctgaggatgg tgactactta   3000

ccaaaacagt taactaatga tctgtcagaa actggcttta cacacgatga taaaggaatc   3060

atctattata cattaagtgg ttatcgtgcc caaaatgcat ttattcaaga tgatgataat   3120

aactattact attttgataa aacaggtcat ttagtaacag gtttgcaaaa gattaataac   3180

catacctact tcttcttacc taatggtatc gaactggtca agagcttctt acaaaacgaa   3240
```

-continued

```
gatggtacaa ttgtttattt cgataagaaa ggtcatcaag tttttgatca atatataact   3300

gatcaaaatg gaaatgcgta ttactttgat gatgctggtg taatgcttaa atcagggctt   3360

gcaacgattg atggacatca acagtatttt gatcaaaatg gtgtgcaggt taaggataag   3420

tttgtgattg gcactgatgg ttataagtat tactttgaac caggtagtgg taacttagct   3480

atcctacgtt atgtgcaaaa tagtaagaat caatggttct attttgatgg taatggccat   3540

gctgtcactg gtttccaaac aattaatggt aaaaaacaat atttctataa tgatggtcat   3600

caaagtaaag gtgaattcat tgatgcagac ggggatactt tctatacgag tgccactgat   3660

ggtcgcctag taactggtgt tcagaagatt aatggtatta cctatgcttt tgataacaca   3720

ggaaatttga tcacaaatca gtattatcaa ttagcagatg gtaaatatat gttgttagat   3780

gatagtggtc gtgcgaaaac agggtttgta ttgcaagatg gtgtactaag atacttcgat   3840

caaaacggtg agcaagtgaa agatgctatc attgtggatc cagatactaa cttgagt      3897
```

<210> SEQ ID NO 22
<211> LENGTH: 1299
<212> TYPE: PRT
<213> ORGANISM: Artificial
<220> FEATURE:
<223> OTHER INFORMATION: Truncated dextrane saccharase

<400> SEQUENCE: 22

```
Thr Gln Gln Val Ser Gly Lys Tyr Val Glu Lys Asp Gly Ser Trp Tyr
1               5                   10                  15

Tyr Tyr Phe Asp Asp Gly Lys Asn Ala Lys Gly Leu Ser Thr Ile Asp
            20                  25                  30

Asn Asn Ile Gln Tyr Phe Tyr Glu Ser Gly Lys Gln Ala Lys Gly Gln
        35                  40                  45

Tyr Val Thr Ile Asp Asn Gln Thr Tyr Tyr Phe Asp Lys Gly Ser Gly
    50                  55                  60

Asp Glu Leu Thr Gly Leu Gln Ser Ile Asp Gly Asn Ile Val Ala Phe
65                  70                  75                  80

Asn Asp Glu Gly Gln Gln Ile Phe Asn Gln Tyr Tyr Gln Ser Glu Asn
                85                  90                  95

Gly Thr Thr Tyr Tyr Phe Asp Asp Lys Gly His Ala Ala Thr Gly Ile
            100                 105                 110

Lys Asn Ile Glu Gly Lys Asn Tyr Tyr Phe Asp Asn Leu Gly Gln Leu
        115                 120                 125

Lys Lys Gly Phe Ser Gly Val Ile Asp Gly Gln Ile Met Thr Phe Asp
    130                 135                 140

Gln Glu Thr Gly Gln Glu Val Ser Asn Thr Thr Ser Glu Ile Lys Glu
145                 150                 155                 160

Gly Leu Thr Thr Gln Asn Thr Asp Tyr Ser Glu His Asn Ala Ala His
                165                 170                 175

Gly Thr Asp Ala Glu Asp Phe Glu Asn Ile Asp Gly Tyr Leu Thr Ala
            180                 185                 190

Ser Ser Trp Tyr Arg Pro Thr Gly Ile Leu Arg Asn Gly Thr Asp Trp
        195                 200                 205

Glu Pro Ser Thr Asp Thr Asp Phe Arg Pro Ile Leu Ser Val Trp Trp
    210                 215                 220

Pro Asp Lys Asn Thr Gln Val Asn Tyr Leu Asn Tyr Met Ala Asp Leu
225                 230                 235                 240

Gly Phe Ile Ser Asn Ala Asp Ser Phe Glu Thr Gly Asp Ser Gln Ser
```

-continued

```
                245                 250                 255

Leu Leu Asn Glu Ala Ser Asn Tyr Val Gln Lys Ser Ile Glu Met Lys
            260                 265                 270

Ile Ser Ala Gln Gln Ser Thr Glu Trp Leu Lys Asp Ala Met Ala Ala
        275                 280                 285

Phe Ile Val Ala Gln Pro Gln Trp Asn Glu Thr Ser Glu Asp Met Ser
    290                 295                 300

Asn Asp His Leu Gln Asn Gly Ala Leu Thr Tyr Val Asn Ser Pro Leu
305                 310                 315                 320

Thr Pro Asp Ala Asn Ser Asn Phe Arg Leu Leu Asn Arg Thr Pro Thr
                325                 330                 335

Asn Gln Thr Gly Glu Gln Ala Tyr Asn Leu Asp Asn Ser Lys Gly Gly
            340                 345                 350

Phe Glu Leu Leu Leu Ala Asn Asp Val Asp Asn Ser Asn Pro Val Val
        355                 360                 365

Gln Ala Glu Gln Leu Asn Trp Leu Tyr Tyr Leu Met Asn Phe Gly Thr
    370                 375                 380

Ile Thr Ala Asn Asp Ala Asp Ala Asn Phe Asp Gly Ile Arg Val Asp
385                 390                 395                 400

Ala Val Asp Asn Val Asp Ala Asp Leu Leu Gln Ile Ala Ala Asp Tyr
                405                 410                 415

Phe Lys Leu Ala Tyr Gly Val Asp Gln Asn Asp Ala Thr Ala Asn Gln
            420                 425                 430

His Leu Ser Ile Leu Glu Asp Trp Ser His Asn Asp Pro Leu Tyr Val
        435                 440                 445

Thr Asp Gln Gly Ser Asn Gln Leu Thr Met Asp Asp Tyr Val His Thr
    450                 455                 460

Gln Leu Ile Trp Ser Leu Thr Lys Ser Ser Asp Ile Arg Gly Thr Met
465                 470                 475                 480

Gln Arg Phe Val Asp Tyr Tyr Met Val Asp Arg Ser Asn Asp Ser Thr
                485                 490                 495

Glu Asn Glu Ala Ile Pro Asn Tyr Ser Phe Val Arg Ala His Asp Ser
            500                 505                 510

Glu Val Gln Thr Val Ile Ala Gln Ile Val Ser Asp Leu Tyr Pro Asp
        515                 520                 525

Val Glu Asn Ser Leu Ala Pro Thr Thr Glu Gln Leu Ala Ala Ala Phe
    530                 535                 540

Lys Val Tyr Asn Glu Asp Glu Lys Leu Ala Asp Lys Lys Tyr Thr Gln
545                 550                 555                 560

Tyr Asn Met Ala Ser Ala Tyr Ala Met Leu Leu Thr Asn Lys Asp Thr
                565                 570                 575

Val Pro Arg Val Tyr Tyr Gly Asp Leu Tyr Thr Asp Asp Gly Gln Tyr
            580                 585                 590

Met Ala Thr Lys Ser Pro Tyr Tyr Asp Ala Ile Asn Thr Leu Leu Lys
        595                 600                 605

Ala Arg Val Gln Tyr Val Ala Gly Gly Gln Ser Met Ser Val Asp Ser
    610                 615                 620

Asn Asp Val Leu Thr Ser Val Arg Tyr Gly Lys Asp Ala Met Thr Ala
625                 630                 635                 640

Ser Asp Thr Gly Thr Ser Glu Thr Arg Thr Glu Gly Ile Gly Val Ile
                645                 650                 655

Val Ser Asn Asn Ala Glu Leu Gln Leu Glu Asp Gly His Thr Val Thr
            660                 665                 670
```

-continued

```
Leu His Met Gly Ala Ala His Lys Asn Gln Ala Tyr Arg Ala Leu Leu
        675                 680                 685

Ser Thr Thr Ala Asp Gly Leu Ala Tyr Tyr Asp Thr Asp Glu Asn Ala
    690                 695                 700

Pro Val Ala Tyr Thr Asp Ala Asn Gly Asp Leu Ile Phe Thr Asn Glu
705                 710                 715                 720

Ser Ile Tyr Gly Val Gln Asn Pro Gln Val Ser Gly Tyr Leu Ala Val
                725                 730                 735

Trp Val Pro Val Gly Ala Gln Gln Asp Gln Asp Ala Arg Thr Ala Ser
            740                 745                 750

Asp Thr Thr Thr Asn Thr Ser Asp Lys Val Phe His Ser Asn Ala Ala
        755                 760                 765

Leu Asp Ser Gln Val Ile Tyr Glu Gly Phe Ser Asn Phe Gln Ala Phe
    770                 775                 780

Ala Thr Asp Ser Ser Glu Tyr Thr Asn Val Val Ile Ala Gln Asn Ala
785                 790                 795                 800

Asp Gln Phe Lys Gln Trp Gly Val Thr Ser Phe Gln Leu Ala Pro Gln
                805                 810                 815

Tyr Arg Ser Ser Thr Asp Thr Ser Phe Leu Asp Ser Ile Ile Gln Asn
            820                 825                 830

Gly Tyr Ala Phe Thr Asp Arg Tyr Asp Leu Gly Tyr Gly Thr Pro Thr
        835                 840                 845

Lys Tyr Gly Thr Ala Asp Gln Leu Arg Asp Ala Ile Lys Ala Leu His
    850                 855                 860

Ala Ser Gly Ile Gln Ala Ile Ala Asp Trp Val Pro Asp Gln Ile Tyr
865                 870                 875                 880

Asn Leu Pro Glu Gln Glu Leu Ala Thr Val Thr Arg Thr Asn Ser Phe
                885                 890                 895

Gly Asp Asp Asp Thr Asp Ser Asp Ile Asp Asn Ala Leu Tyr Val Val
            900                 905                 910

Gln Ser Arg Gly Gly Gly Gln Tyr Gln Glu Met Tyr Gly Gly Ala Phe
        915                 920                 925

Leu Glu Glu Leu Gln Ala Leu Tyr Pro Ser Leu Phe Lys Val Asn Gln
    930                 935                 940

Ile Ser Thr Gly Val Pro Ile Asp Gly Ser Val Lys Ile Thr Glu Trp
945                 950                 955                 960

Ala Ala Lys Tyr Phe Asn Gly Ser Asn Ile Gln Gly Lys Gly Ala Gly
                965                 970                 975

Tyr Val Leu Lys Asp Met Gly Ser Asn Lys Tyr Phe Lys Val Val Ser
            980                 985                 990

Asn Thr Glu Asp Gly Asp Tyr Leu  Pro Lys Gln Leu Thr  Asn Asp Leu
        995                 1000                 1005

Ser Glu  Thr Gly Phe Thr His  Asp Asp Lys Gly Ile  Ile Tyr Tyr
    1010                 1015                 1020

Thr Leu  Ser Gly Tyr Arg Ala  Gln Asn Ala Phe Ile  Gln Asp Asp
    1025                 1030                 1035

Asp Asn  Asn Tyr Tyr Tyr Phe  Asp Lys Thr Gly His  Leu Val Thr
    1040                 1045                 1050

Gly Leu  Gln Lys Ile Asn Asn  His Thr Tyr Phe Phe  Leu Pro Asn
    1055                 1060                 1065

Gly Ile  Glu Leu Val Lys Ser  Phe Leu Gln Asn Glu  Asp Gly Thr
    1070                 1075                 1080
```

-continued

```
Ile Val  Tyr Phe Asp Lys Lys  Gly His Gln Val Phe  Asp Gln Tyr
    1085                 1090                 1095

Ile Thr  Asp Gln Asn Gly Asn  Ala Tyr Tyr Phe Asp  Asp Ala Gly
    1100                 1105                 1110

Val Met  Leu Lys Ser Gly Leu  Ala Thr Ile Asp Gly  His Gln Gln
    1115                 1120                 1125

Tyr Phe  Asp Gln Asn Gly Val  Gln Val Lys Asp Lys  Phe Val Ile
    1130                 1135                 1140

Gly Thr  Asp Gly Tyr Lys Tyr  Tyr Phe Glu Pro Gly  Ser Gly Asn
    1145                 1150                 1155

Leu Ala  Ile Leu Arg Tyr Val  Gln Asn Ser Lys Asn  Gln Trp Phe
    1160                 1165                 1170

Tyr Phe  Asp Gly Asn Gly His  Ala Val Thr Gly Phe  Gln Thr Ile
    1175                 1180                 1185

Asn Gly  Lys Lys Gln Tyr Phe  Tyr Asn Asp Gly His  Gln Ser Lys
    1190                 1195                 1200

Gly Glu  Phe Ile Asp Ala Asp  Gly Asp Thr Phe Tyr  Thr Ser Ala
    1205                 1210                 1215

Thr Asp  Gly Arg Leu Val Thr  Gly Val Gln Lys Ile  Asn Gly Ile
    1220                 1225                 1230

Thr Tyr  Ala Phe Asp Asn Thr  Gly Asn Leu Ile Thr  Asn Gln Tyr
    1235                 1240                 1245

Tyr Gln  Leu Ala Asp Gly Lys  Tyr Met Leu Leu Asp  Asp Ser Gly
    1250                 1255                 1260

Arg Ala  Lys Thr Gly Phe Val  Leu Gln Asp Gly Val  Leu Arg Tyr
    1265                 1270                 1275

Phe Asp  Gln Asn Gly Glu Gln  Val Lys Asp Ala Ile  Ile Val Asp
    1280                 1285                 1290

Pro Asp  Thr Asn Leu Ser
    1295


<210> SEQ ID NO 23
<211> LENGTH: 1211
<212> TYPE: PRT
<213> ORGANISM: Artificial
<220> FEATURE:
<223> OTHER INFORMATION: Truncated dextrane saccharase

<400> SEQUENCE: 23

Thr Gln Gln Val Ser Gly Lys Tyr Val Glu Lys Asp Gly Ser Trp Tyr
1               5                   10                  15

Tyr Tyr Phe Asp Asp Gly Lys Asn Ala Lys Gly Leu Ser Thr Ile Asp
            20                  25                  30

Asn Asn Ile Gln Tyr Phe Tyr Glu Ser Gly Lys Gln Ala Lys Gly Gln
        35                  40                  45

Tyr Val Thr Ile Asp Asn Gln Thr Tyr Tyr Phe Asp Lys Gly Ser Gly
    50                  55                  60

Asp Glu Leu Thr Gly Leu Gln Ser Ile Asp Gly Asn Ile Val Ala Phe
65                  70                  75                  80

Asn Asp Glu Gly Gln Gln Ile Phe Asn Gln Tyr Tyr Gln Ser Glu Asn
                85                  90                  95

Gly Thr Thr Tyr Tyr Phe Asp Asp Lys Gly His Ala Ala Thr Gly Ile
            100                 105                 110

Lys Asn Ile Glu Gly Lys Asn Tyr Tyr Phe Asp Asn Leu Gly Gln Leu
        115                 120                 125
```

-continued

```
Lys Lys Gly Phe Ser Gly Val Ile Asp Gly Gln Ile Met Thr Phe Asp
    130                 135                 140

Gln Glu Thr Gly Gln Glu Val Ser Asn Thr Thr Ser Glu Ile Lys Glu
145                 150                 155                 160

Gly Leu Thr Thr Gln Asn Thr Asp Tyr Ser Glu His Asn Ala Ala His
                165                 170                 175

Gly Thr Asp Ala Glu Asp Phe Glu Asn Ile Asp Gly Tyr Leu Thr Ala
            180                 185                 190

Ser Ser Trp Tyr Arg Pro Thr Gly Ile Leu Arg Asn Gly Thr Asp Trp
        195                 200                 205

Glu Pro Ser Thr Asp Thr Asp Phe Arg Pro Ile Leu Ser Val Trp Trp
    210                 215                 220

Pro Asp Lys Asn Thr Gln Val Asn Tyr Leu Asn Tyr Met Ala Asp Leu
225                 230                 235                 240

Gly Phe Ile Ser Asn Ala Asp Ser Phe Glu Thr Gly Asp Ser Gln Ser
                245                 250                 255

Leu Leu Asn Glu Ala Ser Asn Tyr Val Gln Lys Ser Ile Glu Met Lys
            260                 265                 270

Ile Ser Ala Gln Gln Ser Thr Glu Trp Leu Lys Asp Ala Met Ala Ala
        275                 280                 285

Phe Ile Val Ala Gln Pro Gln Trp Asn Glu Thr Ser Glu Asp Met Ser
    290                 295                 300

Asn Asp His Leu Gln Asn Gly Ala Leu Thr Tyr Val Asn Ser Pro Leu
305                 310                 315                 320

Thr Pro Asp Ala Asn Ser Asn Phe Arg Leu Leu Asn Arg Thr Pro Thr
                325                 330                 335

Asn Gln Thr Gly Glu Gln Ala Tyr Asn Leu Asp Asn Ser Lys Gly Gly
            340                 345                 350

Phe Glu Leu Leu Leu Ala Asn Asp Val Asp Asn Ser Asn Pro Val Val
        355                 360                 365

Gln Ala Glu Gln Leu Asn Trp Leu Tyr Tyr Leu Met Asn Phe Gly Thr
    370                 375                 380

Ile Thr Ala Asn Asp Ala Asp Ala Asn Phe Asp Gly Ile Arg Val Asp
385                 390                 395                 400

Ala Val Asp Asn Val Asp Ala Asp Leu Leu Gln Ile Ala Ala Asp Tyr
                405                 410                 415

Phe Lys Leu Ala Tyr Gly Val Asp Gln Asn Asp Ala Thr Ala Asn Gln
            420                 425                 430

His Leu Ser Ile Leu Glu Asp Trp Ser His Asn Asp Pro Leu Tyr Val
        435                 440                 445

Thr Asp Gln Gly Ser Asn Gln Leu Thr Met Asp Asp Tyr Val His Thr
    450                 455                 460

Gln Leu Ile Trp Ser Leu Thr Lys Ser Ser Asp Ile Arg Gly Thr Met
465                 470                 475                 480

Gln Arg Phe Val Asp Tyr Tyr Met Val Asp Arg Ser Asn Asp Ser Thr
                485                 490                 495

Glu Asn Glu Ala Ile Pro Asn Tyr Ser Phe Val Arg Ala His Asp Ser
            500                 505                 510

Glu Val Gln Thr Val Ile Ala Gln Ile Val Ser Asp Leu Tyr Pro Asp
        515                 520                 525

Val Glu Asn Ser Leu Ala Pro Thr Thr Glu Gln Leu Ala Ala Ala Phe
    530                 535                 540

Lys Val Tyr Asn Glu Asp Glu Lys Leu Ala Asp Lys Lys Tyr Thr Gln
```

-continued 545 550 555 560

Tyr Asn Met Ala Ser Ala Tyr Ala Met Leu Leu Thr Asn Lys Asp Thr
565 570 575

Val Pro Arg Val Tyr Tyr Gly Asp Leu Tyr Thr Asp Asp Gly Gln Tyr
580 585 590

Met Ala Thr Lys Ser Pro Tyr Tyr Asp Ala Ile Asn Thr Leu Leu Lys
595 600 605

Ala Arg Val Gln Tyr Val Ala Gly Gly Gln Ser Met Ser Val Asp Ser
610 615 620

Asn Asp Val Leu Thr Ser Val Arg Tyr Gly Lys Asp Ala Met Thr Ala
625 630 635 640

Ser Asp Thr Gly Thr Ser Glu Thr Arg Thr Glu Gly Ile Gly Val Ile
645 650 655

Val Ser Asn Asn Ala Glu Leu Gln Leu Glu Asp Gly His Thr Val Thr
660 665 670

Leu His Met Gly Ala Ala His Lys Asn Gln Ala Tyr Arg Ala Leu Leu
675 680 685

Ser Thr Thr Ala Asp Gly Leu Ala Tyr Tyr Asp Thr Asp Glu Asn Ala
690 695 700

Pro Val Ala Tyr Thr Asp Ala Asn Gly Asp Leu Ile Phe Thr Asn Glu
705 710 715 720

Ser Ile Tyr Gly Val Gln Asn Pro Gln Val Ser Gly Tyr Leu Ala Val
725 730 735

Trp Val Pro Val Gly Ala Gln Gln Asp Gln Asp Ala Arg Thr Ala Ser
740 745 750

Asp Thr Thr Thr Asn Thr Ser Asp Lys Val Phe His Ser Asn Ala Ala
755 760 765

Leu Asp Ser Gln Val Ile Tyr Glu Gly Phe Ser Asn Phe Gln Ala Phe
770 775 780

Ala Thr Asp Ser Ser Glu Tyr Thr Asn Val Val Ile Ala Gln Asn Ala
785 790 795 800

Asp Gln Phe Lys Gln Trp Gly Val Thr Ser Phe Gln Leu Ala Pro Gln
805 810 815

Tyr Arg Ser Ser Thr Asp Thr Ser Phe Leu Asp Ser Ile Ile Gln Asn
820 825 830

Gly Tyr Ala Phe Thr Asp Arg Tyr Asp Leu Gly Tyr Gly Thr Pro Thr
835 840 845

Lys Tyr Gly Thr Ala Asp Gln Leu Arg Asp Ala Ile Lys Ala Leu His
850 855 860

Ala Ser Gly Ile Gln Ala Ile Ala Asp Trp Val Pro Asp Gln Ile Tyr
865 870 875 880

Asn Leu Pro Glu Gln Glu Leu Ala Thr Val Thr Arg Thr Asn Ser Phe
885 890 895

Gly Asp Asp Asp Thr Asp Ser Asp Ile Asp Asn Ala Leu Tyr Val Val
900 905 910

Gln Ser Arg Gly Gly Gly Gln Tyr Gln Glu Met Tyr Gly Gly Ala Phe
915 920 925

Leu Glu Glu Leu Gln Ala Leu Tyr Pro Ser Leu Phe Lys Val Asn Gln
930 935 940

Ile Ser Thr Gly Val Pro Ile Asp Gly Ser Val Lys Ile Thr Glu Trp
945 950 955 960

Ala Ala Lys Tyr Phe Asn Gly Ser Asn Ile Gln Gly Lys Gly Ala Gly
965 970 975

-continued

Tyr Val Leu Lys Asp Met Gly Ser Asn Lys Tyr Phe Lys Val Val Ser
980 985 990

Asn Thr Glu Asp Gly Asp Tyr Leu Pro Lys Gln Leu Thr Asn Asp Leu
995 1000 1005

Ser Glu Thr Gly Phe Thr His Asp Asp Lys Gly Ile Ile Tyr Tyr
1010 1015 1020

Thr Leu Ser Gly Tyr Arg Ala Gln Asn Ala Phe Ile Gln Asp Asp
1025 1030 1035

Asp Asn Asn Tyr Tyr Tyr Phe Asp Lys Thr Gly His Leu Val Thr
1040 1045 1050

Gly Leu Gln Lys Ile Asn Asn His Thr Tyr Phe Phe Leu Pro Asn
1055 1060 1065

Gly Ile Glu Leu Val Lys Ser Phe Leu Gln Asn Glu Asp Gly Thr
1070 1075 1080

Ile Val Tyr Phe Asp Lys Lys Gly His Gln Val Phe Asp Gln Tyr
1085 1090 1095

Ile Thr Asp Gln Asn Gly Asn Ala Tyr Tyr Phe Asp Asp Ala Gly
1100 1105 1110

Val Met Leu Lys Ser Gly Leu Ala Thr Ile Asp Gly His Gln Gln
1115 1120 1125

Tyr Phe Asp Gln Asn Gly Val Gln Val Lys Asp Lys Phe Val Ile
1130 1135 1140

Gly Thr Asp Gly Tyr Lys Tyr Tyr Phe Glu Pro Gly Ser Gly Asn
1145 1150 1155

Leu Ala Ile Leu Arg Tyr Val Gln Asn Ser Lys Asn Gln Trp Phe
1160 1165 1170

Tyr Phe Asp Gly Asn Gly His Ala Val Thr Gly Phe Gln Thr Ile
1175 1180 1185

Asn Gly Lys Lys Gln Tyr Phe Tyr Asn Asp Gly His Gln Ser Lys
1190 1195 1200

Gly Glu Phe Ile Asp Ala Asp Gly
1205 1210

<210> SEQ ID NO 24
<211> LENGTH: 1012
<212> TYPE: PRT
<213> ORGANISM: Artificial
<220> FEATURE:
<223> OTHER INFORMATION: Truncated dextrane saccharase

<400> SEQUENCE: 24

Thr Gln Gln Val Ser Gly Lys Tyr Val Glu Lys Asp Gly Ser Trp Tyr
1 5 10 15

Tyr Tyr Phe Asp Asp Gly Lys Asn Ala Lys Gly Leu Ser Thr Ile Asp
20 25 30

Asn Asn Ile Gln Tyr Phe Tyr Glu Ser Gly Lys Gln Ala Lys Gly Gln
35 40 45

Tyr Val Thr Ile Asp Asn Gln Thr Tyr Tyr Phe Asp Lys Gly Ser Gly
50 55 60

Asp Glu Leu Thr Gly Leu Gln Ser Ile Asp Gly Asn Ile Val Ala Phe
65 70 75 80

Asn Asp Glu Gly Gln Gln Ile Phe Asn Gln Tyr Tyr Gln Ser Glu Asn
85 90 95

Gly Thr Thr Tyr Tyr Phe Asp Asp Lys Gly His Ala Ala Thr Gly Ile
100 105 110

-continued

Lys Asn Ile Glu Gly Lys Asn Tyr Tyr Phe Asp Asn Leu Gly Gln Leu
115 120 125

Lys Lys Gly Phe Ser Gly Val Ile Asp Gly Gln Ile Met Thr Phe Asp
130 135 140

Gln Glu Thr Gly Gln Glu Val Ser Asn Thr Thr Ser Glu Ile Lys Glu
145 150 155 160

Gly Leu Thr Thr Gln Asn Thr Asp Tyr Ser Glu His Asn Ala Ala His
165 170 175

Gly Thr Asp Ala Glu Asp Phe Glu Asn Ile Asp Gly Tyr Leu Thr Ala
180 185 190

Ser Ser Trp Tyr Arg Pro Thr Gly Ile Leu Arg Asn Gly Thr Asp Trp
195 200 205

Glu Pro Ser Thr Asp Thr Asp Phe Arg Pro Ile Leu Ser Val Trp Trp
210 215 220

Pro Asp Lys Asn Thr Gln Val Asn Tyr Leu Asn Tyr Met Ala Asp Leu
225 230 235 240

Gly Phe Ile Ser Asn Ala Asp Ser Phe Glu Thr Gly Asp Ser Gln Ser
245 250 255

Leu Leu Asn Glu Ala Ser Asn Tyr Val Gln Lys Ser Ile Glu Met Lys
260 265 270

Ile Ser Ala Gln Gln Ser Thr Glu Trp Leu Lys Asp Ala Met Ala Ala
275 280 285

Phe Ile Val Ala Gln Pro Gln Trp Asn Glu Thr Ser Glu Asp Met Ser
290 295 300

Asn Asp His Leu Gln Asn Gly Ala Leu Thr Tyr Val Asn Ser Pro Leu
305 310 315 320

Thr Pro Asp Ala Asn Ser Asn Phe Arg Leu Leu Asn Arg Thr Pro Thr
325 330 335

Asn Gln Thr Gly Glu Gln Ala Tyr Asn Leu Asp Asn Ser Lys Gly Gly
340 345 350

Phe Glu Leu Leu Leu Ala Asn Asp Val Asp Asn Ser Asn Pro Val Val
355 360 365

Gln Ala Glu Gln Leu Asn Trp Leu Tyr Tyr Leu Met Asn Phe Gly Thr
370 375 380

Ile Thr Ala Asn Asp Ala Asp Ala Asn Phe Asp Gly Ile Arg Val Asp
385 390 395 400

Ala Val Asp Asn Val Asp Ala Asp Leu Leu Gln Ile Ala Ala Asp Tyr
405 410 415

Phe Lys Leu Ala Tyr Gly Val Asp Gln Asn Asp Ala Thr Ala Asn Gln
420 425 430

His Leu Ser Ile Leu Glu Asp Trp Ser His Asn Asp Pro Leu Tyr Val
435 440 445

Thr Asp Gln Gly Ser Asn Gln Leu Thr Met Asp Asp Tyr Val His Thr
450 455 460

Gln Leu Ile Trp Ser Leu Thr Lys Ser Ser Asp Ile Arg Gly Thr Met
465 470 475 480

Gln Arg Phe Val Asp Tyr Tyr Met Val Asp Arg Ser Asn Asp Ser Thr
485 490 495

Glu Asn Glu Ala Ile Pro Asn Tyr Ser Phe Val Arg Ala His Asp Ser
500 505 510

Glu Val Gln Thr Val Ile Ala Gln Ile Val Ser Asp Leu Tyr Pro Asp
515 520 525

-continued

```
Val Glu Asn Ser Leu Ala Pro Thr Thr Glu Gln Leu Ala Ala Ala Phe
    530                 535                 540

Lys Val Tyr Asn Glu Asp Glu Lys Leu Ala Asp Lys Lys Tyr Thr Gln
545                 550                 555                 560

Tyr Asn Met Ala Ser Ala Tyr Ala Met Leu Leu Thr Asn Lys Asp Thr
                565                 570                 575

Val Pro Arg Val Tyr Tyr Gly Asp Leu Tyr Thr Asp Asp Gly Gln Tyr
            580                 585                 590

Met Ala Thr Lys Ser Pro Tyr Tyr Asp Ala Ile Asn Thr Leu Leu Lys
        595                 600                 605

Ala Arg Val Gln Tyr Val Ala Gly Gly Gln Ser Met Ser Val Asp Ser
    610                 615                 620

Asn Asp Val Leu Thr Ser Val Arg Tyr Gly Lys Asp Ala Met Thr Ala
625                 630                 635                 640

Ser Asp Thr Gly Thr Ser Glu Thr Arg Thr Glu Gly Ile Gly Val Ile
                645                 650                 655

Val Ser Asn Asn Ala Glu Leu Gln Leu Glu Asp Gly His Thr Val Thr
            660                 665                 670

Leu His Met Gly Ala Ala His Lys Asn Gln Ala Tyr Arg Ala Leu Leu
        675                 680                 685

Ser Thr Thr Ala Asp Gly Leu Ala Tyr Tyr Asp Thr Asp Glu Asn Ala
    690                 695                 700

Pro Val Ala Tyr Thr Asp Ala Asn Gly Asp Leu Ile Phe Thr Asn Glu
705                 710                 715                 720

Ser Ile Tyr Gly Val Gln Asn Pro Gln Val Ser Gly Tyr Leu Ala Val
                725                 730                 735

Trp Val Pro Val Gly Ala Gln Gln Asp Gln Asp Ala Arg Thr Ala Ser
            740                 745                 750

Asp Thr Thr Thr Asn Thr Ser Asp Lys Val Phe His Ser Asn Ala Ala
        755                 760                 765

Leu Asp Ser Gln Val Ile Tyr Glu Gly Phe Ser Asn Phe Gln Ala Phe
    770                 775                 780

Ala Thr Asp Ser Ser Glu Tyr Thr Asn Val Val Ile Ala Gln Asn Ala
785                 790                 795                 800

Asp Gln Phe Lys Gln Trp Gly Val Thr Ser Phe Gln Leu Ala Pro Gln
                805                 810                 815

Tyr Arg Ser Ser Thr Asp Thr Ser Phe Leu Asp Ser Ile Ile Gln Asn
            820                 825                 830

Gly Tyr Ala Phe Thr Asp Arg Tyr Asp Leu Gly Tyr Gly Thr Pro Thr
        835                 840                 845

Lys Tyr Gly Thr Ala Asp Gln Leu Arg Asp Ala Ile Lys Ala Leu His
    850                 855                 860

Ala Ser Gly Ile Gln Ala Ile Ala Asp Trp Val Pro Asp Gln Ile Tyr
865                 870                 875                 880

Asn Leu Pro Glu Gln Glu Leu Ala Thr Val Thr Arg Thr Asn Ser Phe
                885                 890                 895

Gly Asp Asp Asp Thr Asp Ser Asp Ile Asp Asn Ala Leu Tyr Val Val
            900                 905                 910

Gln Ser Arg Gly Gly Gly Gln Tyr Gln Glu Met Tyr Gly Gly Ala Phe
        915                 920                 925

Leu Glu Glu Leu Gln Ala Leu Tyr Pro Ser Leu Phe Lys Val Asn Gln
    930                 935                 940

Ile Ser Thr Gly Val Pro Ile Asp Gly Ser Val Lys Ile Thr Glu Trp
```

-continued

```
945                 950                 955                 960

Ala Ala Lys Tyr Phe Asn Gly Ser Asn Ile Gln Gly Lys Gly Ala Gly
                965                 970                 975

Tyr Val Leu Lys Asp Met Gly Ser Asn Lys Tyr Phe Lys Val Val Ser
            980                 985                 990

Asn Thr Glu Asp Gly Asp Tyr Leu  Pro Lys Gln Leu Thr  Asn Asp Leu
        995                 1000                 1005

Ser Glu  Thr Gly
    1010


<210> SEQ ID NO 25
<211> LENGTH: 882
<212> TYPE: PRT
<213> ORGANISM: Artificial
<220> FEATURE:
<223> OTHER INFORMATION: Truncated dextrane saccharase

<400> SEQUENCE: 25

Gly Phe Ser Gly Val Ile Asp Gly Gln Ile Met Thr Phe Asp Gln Glu
1               5                   10                  15

Thr Gly Gln Glu Val Ser Asn Thr Thr Ser Glu Ile Lys Glu Gly Leu
            20                  25                  30

Thr Thr Gln Asn Thr Asp Tyr Ser Glu His Asn Ala Ala His Gly Thr
        35                  40                  45

Asp Ala Glu Asp Phe Glu Asn Ile Asp Gly Tyr Leu Thr Ala Ser Ser
    50                  55                  60

Trp Tyr Arg Pro Thr Gly Ile Leu Arg Asn Gly Thr Asp Trp Glu Pro
65                  70                  75                  80

Ser Thr Asp Thr Asp Phe Arg Pro Ile Leu Ser Val Trp Trp Pro Asp
                85                  90                  95

Lys Asn Thr Gln Val Asn Tyr Leu Asn Tyr Met Ala Asp Leu Gly Phe
            100                 105                 110

Ile Ser Asn Ala Asp Ser Phe Glu Thr Gly Asp Ser Gln Ser Leu Leu
        115                 120                 125

Asn Glu Ala Ser Asn Tyr Val Gln Lys Ser Ile Glu Met Lys Ile Ser
    130                 135                 140

Ala Gln Gln Ser Thr Glu Trp Leu Lys Asp Ala Met Ala Ala Phe Ile
145                 150                 155                 160

Val Ala Gln Pro Gln Trp Asn Glu Thr Ser Glu Asp Met Ser Asn Asp
                165                 170                 175

His Leu Gln Asn Gly Ala Leu Thr Tyr Val Asn Ser Pro Leu Thr Pro
            180                 185                 190

Asp Ala Asn Ser Asn Phe Arg Leu Leu Asn Arg Thr Pro Thr Asn Gln
        195                 200                 205

Thr Gly Glu Gln Ala Tyr Asn Leu Asp Asn Ser Lys Gly Gly Phe Glu
    210                 215                 220

Leu Leu Leu Ala Asn Asp Val Asp Asn Ser Asn Pro Val Val Gln Ala
225                 230                 235                 240

Glu Gln Leu Asn Trp Leu Tyr Tyr Leu Met Asn Phe Gly Thr Ile Thr
                245                 250                 255

Ala Asn Asp Ala Asp Ala Asn Phe Asp Gly Ile Arg Val Asp Ala Val
            260                 265                 270

Asp Asn Val Asp Ala Asp Leu Leu Gln Ile Ala Ala Asp Tyr Phe Lys
        275                 280                 285

Leu Ala Tyr Gly Val Asp Gln Asn Asp Ala Thr Ala Asn Gln His Leu
```

-continued

```
    290                 295                 300

Ser Ile Leu Glu Asp Trp Ser His Asn Asp Pro Leu Tyr Val Thr Asp
305                 310                 315                 320

Gln Gly Ser Asn Gln Leu Thr Met Asp Asp Tyr Val His Thr Gln Leu
                325                 330                 335

Ile Trp Ser Leu Thr Lys Ser Ser Asp Ile Arg Gly Thr Met Gln Arg
            340                 345                 350

Phe Val Asp Tyr Tyr Met Val Asp Arg Ser Asn Asp Ser Thr Glu Asn
        355                 360                 365

Glu Ala Ile Pro Asn Tyr Ser Phe Val Arg Ala His Asp Ser Glu Val
    370                 375                 380

Gln Thr Val Ile Ala Gln Ile Val Ser Asp Leu Tyr Pro Asp Val Glu
385                 390                 395                 400

Asn Ser Leu Ala Pro Thr Thr Glu Gln Leu Ala Ala Ala Phe Lys Val
                405                 410                 415

Tyr Asn Glu Asp Glu Lys Leu Ala Asp Lys Lys Tyr Thr Gln Tyr Asn
            420                 425                 430

Met Ala Ser Ala Tyr Ala Met Leu Leu Thr Asn Lys Asp Thr Val Pro
        435                 440                 445

Arg Val Tyr Tyr Gly Asp Leu Tyr Thr Asp Asp Gly Gln Tyr Met Ala
    450                 455                 460

Thr Lys Ser Pro Tyr Tyr Asp Ala Ile Asn Thr Leu Leu Lys Ala Arg
465                 470                 475                 480

Val Gln Tyr Val Ala Gly Gly Gln Ser Met Ser Val Asp Ser Asn Asp
                485                 490                 495

Val Leu Thr Ser Val Arg Tyr Gly Lys Asp Ala Met Thr Ala Ser Asp
            500                 505                 510

Thr Gly Thr Ser Glu Thr Arg Thr Glu Gly Ile Gly Val Ile Val Ser
        515                 520                 525

Asn Asn Ala Glu Leu Gln Leu Glu Asp Gly His Thr Val Thr Leu His
    530                 535                 540

Met Gly Ala Ala His Lys Asn Gln Ala Tyr Arg Ala Leu Leu Ser Thr
545                 550                 555                 560

Thr Ala Asp Gly Leu Ala Tyr Tyr Asp Thr Asp Glu Asn Ala Pro Val
                565                 570                 575

Ala Tyr Thr Asp Ala Asn Gly Asp Leu Ile Phe Thr Asn Glu Ser Ile
            580                 585                 590

Tyr Gly Val Gln Asn Pro Gln Val Ser Gly Tyr Leu Ala Val Trp Val
        595                 600                 605

Pro Val Gly Ala Gln Gln Asp Gln Asp Ala Arg Thr Ala Ser Asp Thr
    610                 615                 620

Thr Thr Asn Thr Ser Asp Lys Val Phe His Ser Asn Ala Ala Leu Asp
625                 630                 635                 640

Ser Gln Val Ile Tyr Glu Gly Phe Ser Asn Phe Gln Ala Phe Ala Thr
                645                 650                 655

Asp Ser Ser Glu Tyr Thr Asn Val Val Ile Ala Gln Asn Ala Asp Gln
            660                 665                 670

Phe Lys Gln Trp Gly Val Thr Ser Phe Gln Leu Ala Pro Gln Tyr Arg
        675                 680                 685

Ser Ser Thr Asp Thr Ser Phe Leu Asp Ser Ile Ile Gln Asn Gly Tyr
    690                 695                 700

Ala Phe Thr Asp Arg Tyr Asp Leu Gly Tyr Gly Thr Pro Thr Lys Tyr
705                 710                 715                 720
```

-continued

Gly Thr Ala Asp Gln Leu Arg Asp Ala Ile Lys Ala Leu His Ala Ser
725 730 735

Gly Ile Gln Ala Ile Ala Asp Trp Val Pro Asp Gln Ile Tyr Asn Leu
740 745 750

Pro Glu Gln Glu Leu Ala Thr Val Thr Arg Thr Asn Ser Phe Gly Asp
755 760 765

Asp Asp Thr Asp Ser Asp Ile Asp Asn Ala Leu Tyr Val Val Gln Ser
770 775 780

Arg Gly Gly Gly Gln Tyr Gln Glu Met Tyr Gly Gly Ala Phe Leu Glu
785 790 795 800

Glu Leu Gln Ala Leu Tyr Pro Ser Leu Phe Lys Val Asn Gln Ile Ser
805 810 815

Thr Gly Val Pro Ile Asp Gly Ser Val Lys Ile Thr Glu Trp Ala Ala
820 825 830

Lys Tyr Phe Asn Gly Ser Asn Ile Gln Gly Lys Gly Ala Gly Tyr Val
835 840 845

Leu Lys Asp Met Gly Ser Asn Lys Tyr Phe Lys Val Val Ser Asn Thr
850 855 860

Glu Asp Gly Asp Tyr Leu Pro Lys Gln Leu Thr Asn Asp Leu Ser Glu
865 870 875 880

Thr Gly

<210> SEQ ID NO 26
<211> LENGTH: 1299
<212> TYPE: PRT
<213> ORGANISM: Artificial
<220> FEATURE:
<223> OTHER INFORMATION: Mutated / truncated

<400> SEQUENCE: 26

Thr Gln Gln Val Ser Gly Lys Tyr Val Glu Lys Asp Gly Ser Trp Tyr
1 5 10 15

Tyr Tyr Phe Asp Asp Gly Lys Asn Ala Lys Gly Leu Ser Thr Ile Asp
20 25 30

Asn Asn Ile Gln Tyr Phe Tyr Glu Ser Gly Lys Gln Ala Lys Gly Gln
35 40 45

Tyr Val Thr Ile Asp Asn Gln Thr Tyr Tyr Phe Asp Lys Gly Ser Gly
50 55 60

Asp Glu Leu Thr Gly Leu Gln Ser Ile Asp Gly Asn Ile Val Ala Phe
65 70 75 80

Asn Asp Glu Gly Gln Gln Ile Phe Asn Gln Tyr Tyr Gln Ser Glu Asn
85 90 95

Gly Thr Thr Tyr Tyr Phe Asp Asp Lys Gly His Ala Ala Thr Gly Ile
100 105 110

Lys Asn Ile Glu Gly Lys Asn Tyr Tyr Phe Asp Asn Leu Gly Gln Leu
115 120 125

Lys Lys Gly Phe Ser Gly Val Ile Asp Gly Gln Ile Met Thr Phe Asp
130 135 140

Gln Glu Thr Gly Gln Glu Val Ser Asn Thr Thr Ser Glu Ile Lys Glu
145 150 155 160

Gly Leu Thr Thr Gln Asn Thr Asp Tyr Ser Glu His Asn Ala Ala His
165 170 175

Gly Thr Asp Ala Glu Asp Phe Glu Asn Ile Asp Gly Tyr Leu Thr Ala
180 185 190

-continued

```
Ser Ser Trp Tyr Arg Pro Thr Gly Ile Leu Arg Asn Gly Thr Asp Trp
        195                 200                 205

Glu Pro Ser Thr Asp Thr Asp Phe Arg Pro Ile Leu Ser Val Trp Trp
    210                 215                 220

Pro Asp Lys Asn Thr Gln Val Asn Tyr Leu Asn Tyr Met Ala Asp Leu
225                 230                 235                 240

Gly Phe Ile Ser Asn Ala Asp Ser Phe Glu Thr Gly Asp Ser Gln Ser
                245                 250                 255

Leu Leu Asn Glu Ala Ser Asn Tyr Val Gln Lys Ser Ile Glu Met Lys
            260                 265                 270

Ile Ser Ala Gln Gln Ser Thr Glu Trp Leu Lys Asp Ala Met Ala Ala
        275                 280                 285

Phe Ile Val Ala Gln Pro Gln Trp Asn Glu Thr Ser Glu Asp Met Ser
    290                 295                 300

Asn Asp His Leu Gln Asn Gly Ala Leu Thr Tyr Val Asn Ser Pro Leu
305                 310                 315                 320

Thr Pro Asp Ala Asn Ser Asn Phe Arg Leu Leu Asn Arg Thr Pro Thr
                325                 330                 335

Asn Gln Thr Gly Glu Gln Ala Tyr Asn Leu Asp Asn Ser Lys Gly Gly
            340                 345                 350

Phe Glu Leu Leu Leu Ala Asn Asp Val Asp Asn Ser Asn Pro Val Val
        355                 360                 365

Gln Ala Glu Gln Leu Asn Trp Leu Tyr Tyr Leu Met Asn Phe Gly Thr
    370                 375                 380

Ile Thr Ala Asn Asp Ala Asp Ala Asn Phe Asp Gly Ile Arg Val Asp
385                 390                 395                 400

Ala Val Asp Asn Val Asp Ala Asp Leu Leu Gln Ile Ala Ala Asp Tyr
                405                 410                 415

Phe Lys Leu Ala Tyr Gly Val Asp Gln Asn Asp Ala Thr Ala Asn Gln
            420                 425                 430

His Leu Ser Ile Leu Glu Asp Trp Ser His Asn Asp Pro Leu Tyr Val
        435                 440                 445

Thr Asp Gln Gly Ser Asn Gln Leu Thr Met Asp Asp Tyr Val His Thr
    450                 455                 460

Gln Leu Ile Trp Ser Leu Thr Lys Ser Ser Asp Ile Arg Gly Thr Met
465                 470                 475                 480

Gln Arg Phe Val Asp Tyr Tyr Met Val Asp Arg Ser Asn Asp Ser Thr
                485                 490                 495

Glu Asn Glu Ala Ile Pro Asn Tyr Ser Phe Val Arg Ala His Asp Tyr
            500                 505                 510

Asp Ala Gln Thr Val Ile Ala Gln Ile Val Ser Asp Leu Tyr Pro Asp
        515                 520                 525

Val Glu Asn Ser Leu Ala Pro Thr Thr Glu Gln Leu Ala Ala Ala Phe
    530                 535                 540

Lys Val Tyr Asn Glu Asp Glu Lys Leu Ala Asp Lys Lys Tyr Thr Gln
545                 550                 555                 560

Tyr Asn Met Ala Ser Ala Tyr Ala Met Leu Leu Thr Asn Lys Asp Thr
                565                 570                 575

Val Pro Arg Val Tyr Tyr Gly Asp Leu Tyr Thr Asp Asp Gly Gln Tyr
            580                 585                 590

Met Ala Thr Lys Ser Pro Tyr Tyr Asp Ala Ile Asn Thr Leu Leu Lys
        595                 600                 605

Ala Arg Val Gln Tyr Val Ala Gly Gly Gln Ser Met Ser Val Asp Ser
```

-continued

```
    610                 615                 620

Asn Asp Val Leu Thr Ser Val Arg Tyr Gly Lys Asp Ala Met Thr Ala
625                 630                 635                 640

Ser Asp Thr Gly Thr Ser Glu Thr Arg Thr Glu Gly Ile Gly Val Ile
                645                 650                 655

Val Ser Asn Asn Ala Glu Leu Gln Leu Glu Asp Gly His Thr Val Thr
            660                 665                 670

Leu His Met Gly Ala Ala His Lys Asn Gln Ala Tyr Arg Ala Leu Leu
        675                 680                 685

Ser Thr Thr Ala Asp Gly Leu Ala Tyr Tyr Asp Thr Asp Glu Asn Ala
    690                 695                 700

Pro Val Ala Tyr Thr Asp Ala Asn Gly Asp Leu Ile Phe Thr Asn Glu
705                 710                 715                 720

Ser Ile Tyr Gly Val Gln Asn Pro Gln Val Ser Gly Tyr Leu Ala Val
                725                 730                 735

Trp Val Pro Val Gly Ala Gln Gln Asp Gln Asp Ala Arg Thr Ala Ser
            740                 745                 750

Asp Thr Thr Thr Asn Thr Ser Asp Lys Val Phe His Ser Asn Ala Ala
        755                 760                 765

Leu Asp Ser Gln Val Ile Tyr Glu Gly Phe Ser Asn Phe Gln Ala Phe
    770                 775                 780

Ala Thr Asp Ser Ser Glu Tyr Thr Asn Val Val Ile Ala Gln Asn Ala
785                 790                 795                 800

Asp Gln Phe Lys Gln Trp Gly Val Thr Ser Phe Gln Leu Ala Pro Gln
                805                 810                 815

Tyr Arg Ser Ser Thr Asp Thr Ser Phe Leu Asp Ser Ile Ile Gln Asn
            820                 825                 830

Gly Tyr Ala Phe Thr Asp Arg Tyr Asp Leu Gly Tyr Gly Thr Pro Thr
        835                 840                 845

Lys Tyr Gly Thr Ala Asp Gln Leu Arg Asp Ala Ile Lys Ala Leu His
    850                 855                 860

Ala Ser Gly Ile Gln Ala Ile Ala Asp Trp Val Pro Asp Gln Ile Tyr
865                 870                 875                 880

Asn Leu Pro Glu Gln Glu Leu Ala Thr Val Thr Arg Thr Asn Ser Phe
                885                 890                 895

Gly Asp Asp Asp Thr Asp Ser Asp Ile Asp Asn Ala Leu Tyr Val Val
            900                 905                 910

Gln Ser Arg Gly Gly Gly Gln Tyr Gln Glu Met Tyr Gly Gly Ala Phe
        915                 920                 925

Leu Glu Glu Leu Gln Ala Leu Tyr Pro Ser Leu Phe Lys Val Asn Gln
    930                 935                 940

Ile Ser Thr Gly Val Pro Ile Asp Gly Ser Val Lys Ile Thr Glu Trp
945                 950                 955                 960

Ala Ala Lys Tyr Phe Asn Gly Ser Asn Ile Gln Gly Lys Gly Ala Gly
                965                 970                 975

Tyr Val Leu Lys Asp Met Gly Ser Asn Lys Tyr Phe Lys Val Val Ser
            980                 985                 990

Asn Thr Glu Asp Gly Asp Tyr Leu  Pro Lys Gln Leu Thr  Asn Asp Leu
        995                 1000                1005

Ser Glu  Thr Gly Phe Thr His  Asp Asp Lys Gly Ile  Ile Tyr Tyr
    1010                1015                1020

Thr Leu  Ser Gly Tyr Arg Ala  Gln Asn Ala Phe Ile  Gln Asp Asp
    1025                1030                1035
```

-continued

```
Asp Asn  Asn Tyr Tyr Tyr Phe  Asp Lys Thr Gly His  Leu Val Thr
    1040                 1045                 1050

Gly Leu  Gln Lys Ile Asn Asn  His Thr Tyr Phe Phe  Leu Pro Asn
    1055                 1060                 1065

Gly Ile  Glu Leu Val Lys Ser  Phe Leu Gln Asn Glu  Asp Gly Thr
    1070                 1075                 1080

Ile Val  Tyr Phe Asp Lys Lys  Gly His Gln Val Phe  Asp Gln Tyr
    1085                 1090                 1095

Ile Thr  Asp Gln Asn Gly Asn  Ala Tyr Tyr Phe Asp  Asp Ala Gly
    1100                 1105                 1110

Val Met  Leu Lys Ser Gly Leu  Ala Thr Ile Asp Gly  His Gln Gln
    1115                 1120                 1125

Tyr Phe  Asp Gln Asn Gly Val  Gln Val Lys Asp Lys  Phe Val Ile
    1130                 1135                 1140

Gly Thr  Asp Gly Tyr Lys Tyr  Tyr Phe Glu Pro Gly  Ser Gly Asn
    1145                 1150                 1155

Leu Ala  Ile Leu Arg Tyr Val  Gln Asn Ser Lys Asn  Gln Trp Phe
    1160                 1165                 1170

Tyr Phe  Asp Gly Asn Gly His  Ala Val Thr Gly Phe  Gln Thr Ile
    1175                 1180                 1185

Asn Gly  Lys Lys Gln Tyr Phe  Tyr Asn Asp Gly His  Gln Ser Lys
    1190                 1195                 1200

Gly Glu  Phe Ile Asp Ala Asp  Gly Asp Thr Phe Tyr  Thr Ser Ala
    1205                 1210                 1215

Thr Asp  Gly Arg Leu Val Thr  Gly Val Gln Lys Ile  Asn Gly Ile
    1220                 1225                 1230

Thr Tyr  Ala Phe Asp Asn Thr  Gly Asn Leu Ile Thr  Asn Gln Tyr
    1235                 1240                 1245

Tyr Gln  Leu Ala Asp Gly Lys  Tyr Met Leu Leu Asp  Asp Ser Gly
    1250                 1255                 1260

Arg Ala  Lys Thr Gly Phe Val  Leu Gln Asp Gly Val  Leu Arg Tyr
    1265                 1270                 1275

Phe Asp  Gln Asn Gly Glu Gln  Val Lys Asp Ala Ile  Ile Val Asp
    1280                 1285                 1290

Pro Asp  Thr Asn Leu Ser
    1295
```